US009580753B2

(12) United States Patent
Matsumoto et al.

(10) Patent No.: US 9,580,753 B2
(45) Date of Patent: Feb. 28, 2017

(54) METHOD FOR PREDICTING RISK OF PORENCEPHALY OR CEREBRAL HEMORRHAGE

(71) Applicant: Public University Corporation Yokohama City University, Yokohama-shi, Kanagawa (JP)

(72) Inventors: Naomichi Matsumoto, Yokohama (JP); Hirotomo Saitsu, Yokohama (JP)

(73) Assignee: PUBLIC UNIVERSITY CORPORATION YOKOHAMA CITY UNIVERSITY, Yokohama-Shi (JP)

( * ) Notice: Subject to any disclaimer, the term of this patent is extended or adjusted under 35 U.S.C. 154(b) by 279 days.

(21) Appl. No.: 14/357,373

(22) PCT Filed: Oct. 29, 2012

(86) PCT No.: PCT/JP2012/077903
§ 371 (c)(1),
(2) Date: May 9, 2014

(87) PCT Pub. No.: WO2013/069495
PCT Pub. Date: May 16, 2013

(65) Prior Publication Data
US 2014/0315208 A1 Oct. 23, 2014

(30) Foreign Application Priority Data
Nov. 11, 2011 (JP) .................................. 2011-247457

(51) Int. Cl.
*C12Q 1/68* (2006.01)
(52) U.S. Cl.
CPC ..... *C12Q 1/6883* (2013.01); *C12Q 2600/156* (2013.01)
(58) Field of Classification Search
None
See application file for complete search history.

(56) References Cited

PUBLICATIONS

DiLuna et al. (Neurosurgery, vol. 65, No. 2, Aug. 2009, p. 419, abstract #956).*
Yoneda et al. (The American Journal of Human Genetics, 90, 86-90, Jan. 13, 2012).*
Jeanne et al. (The American Journal of Human Genetics, 90, 91-101, Jan. 13, 2012).*
Verbeek et al. (European Journal of Human Genetics (2012) 20, 844-851, published online Feb. 15, 2012).*
Berg et al., "Familial porencephaly", Arch Neurol, vol. 40, No. 9, Sep. 1983, pp. 567-569 (Abstract only provided).
Breedveld et al., "Novel mutations in three families confirm a major role of COL4A1 in hereditary porencephaly", J Med Genet, vol. 43, 2006 (Published online Aug. 17, 2005), pp. 490-495.
Favor et al., "Type IV Procollagen Missense Mutations Associated With Defects of the Eye, Vascular Stability, the Brain, Kidney Function and Embryonic or Postnatal Viability in the Mouse, *Mus musculus*: An Extension of the Col4a1 . . . ", Genetics, vol. 175, Feb. 2007, pp. 725-736.
Gould et al., "Mutations in Col4a1 Cause Perinatal Cerebral Hemorrhage and Porencephaly", Science, vol. 308, May 20, 2005, pp. 1167-1171.
Govaert, "Prenatal Stroke", Semin Fetal Neonatal Med., vol. 14, No. 5, Oct. 2009, pp. 250-266 (Abstract only provided).
Hunter, "Porencephaly", In Human Malformations and related Anomalies, S.RE and H. JG, Eds., Oxford University Press, New York, 2006, pp. 645-654.
International Search Report (Form PCT/ISA/210), dated Nov. 20, 2012, for International Application No. PCT/JP2012/077903.
Jeanne et al., "COL4A2 Mutations Impair COL4A1 and COL4A2 Secretion and Cause Hemorrhagic Stroke", The American Journal of Human Genetics, vol. 90, Jan. 13, 2012, pp. 91-101.
Kuo et al., "COL4A1 and COL4A2 mutations and disease: insights into pathogenic mechanisms and potential therapeutic targets", Human Molecular Genetics, vol. 21, Review Issue 1, 2012 (Advanced Access published Aug. 21, 2012), pp. R97-R110.
Lanfranconi et al., "COL4A1 Mutations as a Monogenic Cause of Cerebral Small Vessel Disease: A Systematic Review", Stroke, vol. 41, 2010 (Published online Jun. 17, 2010), pp. e513-e518, including English translation.
Mancini et al., "Hereditary porencephaly: clinical and MRI findings in two Dutch families", Eur J Paediatr Neurol, vol. 8, No. 1, 2004, pp. 45-54 (Abstract only provided).
Meuwissen et al., "Sporadic COL4A1 mutations with extensive prenatal porencephaly resembling hydranencephaly", Neurology, vol. 76, No. 9, Mar. 1, 2011, pp. 844-846 (Abstract only provided).
Moinuddin et al., "Intracranial hemorrhage progressing to porencephaly as a result of congenitally acquired cytomegalovirus infection—an illustrative report", Prenat Diagn., vol. 23, No. 10, Oct. 2003, pp. 797-800 (Abstract only provided).
Verbeek et al., "COL4A2 mutation associated with familial porencephaly and small-vessel disease" European Journal of Human Genetics, vol. 20, 2012 (Published online: Feb. 15, 2012), pp. 844-851 (20 pages total including Supplemental Data).
Vilain et al., "Neuroimaging fails to identify asymptomatic carriers of familial porencephaly", Am J Med Genet, vol. 112, No. 2, Oct. 1, 2002, pp. 198-202 (Abstract only provided).
Yoneda et al., "De Novo and Inherited Mutations in COL4A2, Encoding the Type IV Collagen α2 Chain Cause Porencephaly", The American Journal of Human Genetics, vol. 90, Jan. 13, 2012, pp. 86-90.
Zhang et al., "Do mutations in COL4A1 or COL4A2 cause thin basement membrane nephropathy (TBMN)?", Pediatr Nephrol, vol. 22, 2007 (Published online Jan. 10, 2007), pp. 645-651.

* cited by examiner

*Primary Examiner* — Juliet Switzer
(74) *Attorney, Agent, or Firm* — Birch, Stewart, Kolasch & Birch, LLP

(57) ABSTRACT

As a result of intensive screening on mutations of the COL4A2 gene in 35 Japanese patients with porencephaly, it was found that the COL4A2 gene is a causative gene for familial and sporadic porencephalies. Since an identical heterozygous mutation of the COL4A2 gene was found in both a porencephaly patient and healthy individuals, this pathogenic mutation is considered to be dominantly inherited with incomplete penetrance. It can be predicted that a living body having a COL4A2 gene mutation has a high risk of occurrence of porencephaly and/or cerebral hemorrhage.

12 Claims, 3 Drawing Sheets

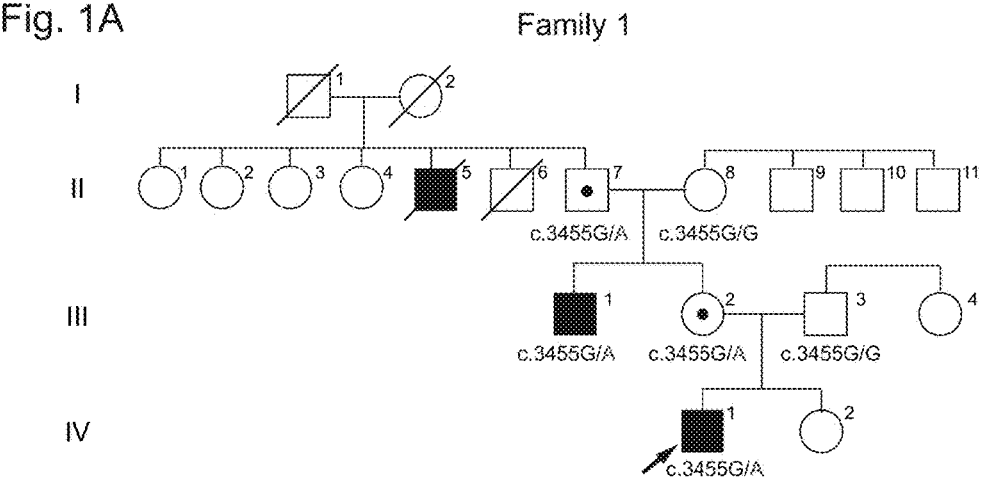
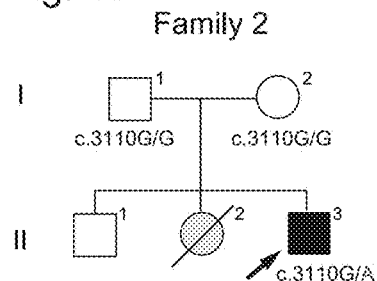
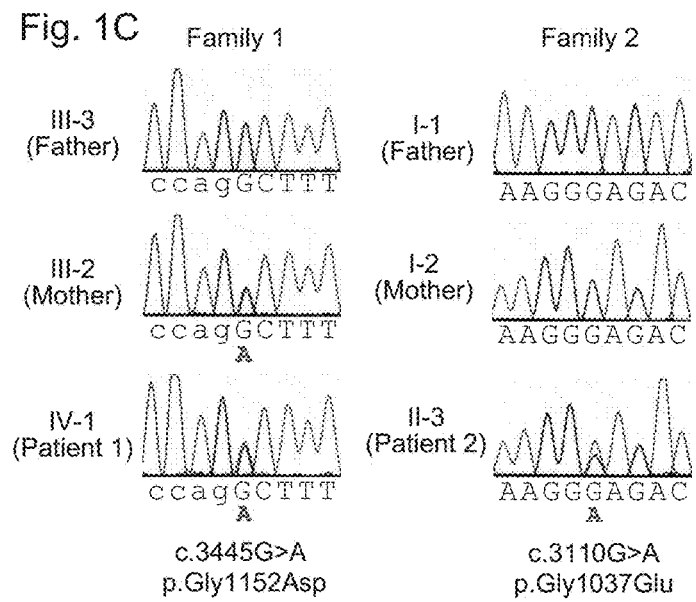
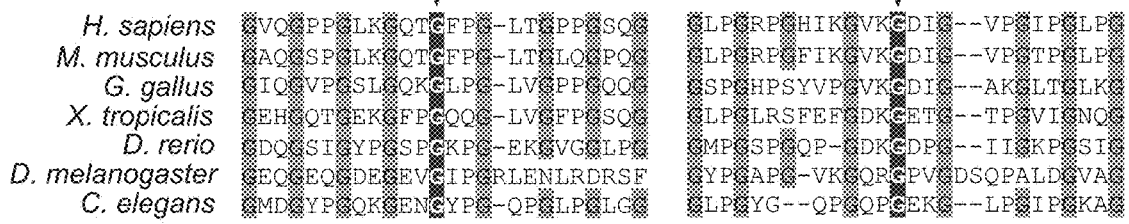

COL4A2: NP_001837.2, 1712aa

MGRDQRAVAGPALRRWLLLGTVTVGFLAQSVLAGVKKFDVPCGGRDCSGGCQCYPEKGGRGQPG
PVGPQGYNGPPGLQGFPGLQGRKGDKGERGAPGVTGPKGDVGARGVSGFPGADGIPGHPGQGGP
RGRPGYDGCNGTQGDSGPQGPPGSEGFTGPPGPQGPKGQKGEPYALPKEERDRYRGEPGEPGLV
GFQGPPGRPGHVGQMGPVGAPGRPGPPGPPGPKGQQGNRGLGFYGVKGEKGDVGQPGPNGIPSD
TLHPIIAPTGVTFHPDQYKGEKGSEGEPGIRGISLKGEEGIMGFPGLRGYPGLSGEKGSPGQKG
SRGLDGYQGPDGPRGPKGEAGDPGPPGLPAYSPHPSLAKGARGDPGFPGAQGEPGSQGEPGDPG
LPGPPGLSIGDGDQRRGLPGEMGPKGFIGDPGIPALYGGPPGPDGKRGPPGPPGLPGPPGPDGF
LFGLKGAKGRAGFPGLPGSPGARGPKGWKGDAGECRCTEGDEAIKGLPGLPGPKGFAGINGEPG
RKGDRGDPGQHGLPGFPGLKGVPGNIGAPGPKGAKGDSRTITTKGERGQPGVPGVPGMKGDDGS
PGRDGLDGFPGLPGPPGDGIKGPPGDPGYPGIPGTKGTPGEMGPPGLGLPGLKGQRGFPGDAGL
PGPPGFLGPPGPAGTPGQIDCDTDVKRAVGGDRQEAIQPGCIGGPKGLPGLPGPPGPTGAKGLR
GIPGFAGADGGPGPRGLPGDAGREGFPGPPGFIGPRGSKGAVGLPGPDGSPGPIGLPGPDGPPG
ERGLPGEVLGAQPGPRGDAGVPGQPGLKGLPGDRGPPGFRGSQGMPGMPGLKGQPGLPGPSGQP
GLYGPPGLHGFPGAPGQEGPLGLPGIPGREGLPGDRGDPGDTGAPGPVGMKGLSGDRGDAGFTG
EQGHPGSPGFKGIDGMPGTPGLKGDRGSPGMDGFQGMPGLKGRPGFPGSKGEAGFFGIPGLKGL
AGEPGFKGSRGDPGPPGPPPVILPGMKDIKGEKGDEGPMGLKGYLGAKGIQGMPGIPGLSGIPG
LPGRPGHIKGVKGDIGVPGIPGLPGFPGVAGPPGITGFPGFIGSRGDKGAPGRAGLYGEIGATG
DFGDIGDTINLPGRPGLKGERGTTGIPGLKGFFGEKGTEGDIGFPGITGVTGVQGPPGLKGQTG
FPGLTGPPGSQGELGRIGLPGGKGDDGWPGAPGLPGFPGLRGIRGLHGLPGTKGFPGSPGSDIH
GDPGFPGPPGERGDPGEANTLPGPVGVPGQKGDQGAPGERGPPGSPGLQGFPGITPPSNISGAP
GDKGAPGIFGLKGYRGPPGPPGSAALPGSKGDTGNPGAPGTPGTKGWAGDSGPQGRPGVFGLPG
EKGPRGEQGFMGNTGPTGAVGDRGPKGPKGDPGFPGAPGTVGAPGIAGIPQKIAVQPGTVGPQG
RRGPPGAPGEMGPQGPPGEPGFRGAPGKAGPQGRGGVSAVPGFRGDEGPIGHQGPIGQEGAPGR
PGSPGLPGMPGRSVSIGYLLVKHSQTDQEPMCPVGMNKLWSGYSLLYFEGQEKAHNQDLGLAGS
CLARFSTMPFLYCNPGDVCYYASRNDKSYWLSTTAPLPMMPVAEDEIKPYISRCSVCEAPAIAI
AVHSQDVSIPHCPAGWRSLWIGYSFLMHTAAGDEGGGQSLVSPGSCLEDFRATPFIECNGGRGT
CHYYANKYSFWLTTIPEQSFQGSPSADTLKAGLIRTHISRCQVCMKNL

Fig.3

```
                        SEQUENCE LISTING

<160> NUMBER OF SEQ ID NOS: 144

<210> SEQ ID NO 1
<211> LENGTH: 5139
<212> TYPE: DNA
<213> ORGANISM: Homo sapiens
<220> FEATURE:
<221> NAME/KEY: CDS
<222> LOCATION: (1)..(5139)

<400> SEQUENCE: 1 atg ggg aga gac cag cgc gcg gtg gcc ggc cct gcc cta cgg cgg tgg      48
Met Gly Arg Asp Gln Arg Ala Val Ala Gly Pro Ala Leu Arg Arg Trp
1               5                   10                  15 ctg ctg ctg ggg aca gtg acc gtg ggg ttc ctc gcc cag agc gtc ttg      96
Leu Leu Leu Gly Thr Val Thr Val Gly Phe Leu Ala Gln Ser Val Leu
            20                  25                  30 gcg ggt gtg aag aag ttt gat gtg ccg tgt gga gga aga gat tgc agt     144
Ala Gly Val Lys Lys Phe Asp Val Pro Cys Gly Gly Arg Asp Cys Ser
        35                  40                  45 ggg ggc tgc cag tgc tac cct gag aaa ggt gga cgt ggt cag cct ggg     192
Gly Gly Cys Gln Cys Tyr Pro Glu Lys Gly Gly Arg Gly Gln Pro Gly
    50                  55                  60 cca gtg ggc ccc cag ggg tac aat ggg cca cca gga tta caa gga ttc     240
Pro Val Gly Pro Gln Gly Tyr Asn Gly Pro Pro Gly Leu Gln Gly Phe
65                  70                  75                  80 ccg gga ctg cag gga cgt aaa gga gac aag ggt gaa agg gga gcc ccc     288
Pro Gly Leu Gln Gly Arg Lys Gly Asp Lys Gly Glu Arg Gly Ala Pro
                85                  90                  95 gga gta acg gga ccc aag ggc gac gtg gga gca aga ggc gtt tct gga     336
Gly Val Thr Gly Pro Lys Gly Asp Val Gly Ala Arg Gly Val Ser Gly
            100                 105                 110 ttc cct ggt gcc gat gga att cct gga cac ccg ggg caa ggt ggg ccc     384
Phe Pro Gly Ala Asp Gly Ile Pro Gly His Pro Gly Gln Gly Gly Pro
        115                 120                 125 agg gga agg ccg ggc tac gat ggc tgc aac gga acc cag gga gac tca     432
Arg Gly Arg Pro Gly Tyr Asp Gly Cys Asn Gly Thr Gln Gly Asp Ser
    130                 135                 140 ggt cca cag ggg ccc ccc ggc tct gag ggg ttc acc ggg cct ccc ggg     480
Gly Pro Gln Gly Pro Pro Gly Ser Glu Gly Phe Thr Gly Pro Pro Gly
145                 150                 155                 160 ccc caa gga cca aaa ggg cag aaa ggt gag cct tat gca ctg cct aaa     528
Pro Gln Gly Pro Lys Gly Gln Lys Gly Glu Pro Tyr Ala Leu Pro Lys
                165                 170                 175
```

-continued

| | | |
|---|---|---|
| gag gag cgc gac aga tat cgg ggt gaa cct gga gag cct gga ttg gtc<br>Glu Glu Arg Asp Arg Tyr Arg Gly Glu Pro Gly Glu Pro Gly Leu Val<br>180 185 190 | | 576 |
| ggt ttc cag gga cct ccc ggc cgc cct ggg cat gtg gga cag atg ggt<br>Gly Phe Gln Gly Pro Pro Gly Arg Pro Gly His Val Gly Gln Met Gly<br>195 200 205 | | 624 |
| cca gtt gga gct cca ggg aga cca gga cca cct gga ccc cct gga cca<br>Pro Val Gly Ala Pro Gly Arg Pro Gly Pro Pro Gly Pro Pro Gly Pro<br>210 215 220 | | 672 |
| aaa gga cag caa ggc aac aga gga ctt ggt ttc tac gga gtt aag ggt<br>Lys Gly Gln Gln Gly Asn Arg Gly Leu Gly Phe Tyr Gly Val Lys Gly<br>225 230 235 240 | | 720 |
| gaa aag ggt gac gta ggg cag ccg gga ccc aac ggg att cca tca gac<br>Glu Lys Gly Asp Val Gly Gln Pro Gly Pro Asn Gly Ile Pro Ser Asp<br>245 250 255 | | 768 |
| acc ctc cac ccc atc atc gcg ccc aca gga gtc acc ttc cac cca gat<br>Thr Leu His Pro Ile Ile Ala Pro Thr Gly Val Thr Phe His Pro Asp<br>260 265 270 | | 816 |
| cag tac aag ggt gaa aaa ggc agt gag ggg gaa cca gga ata aga ggc<br>Gln Tyr Lys Gly Glu Lys Gly Ser Glu Gly Glu Pro Gly Ile Arg Gly<br>275 280 285 | | 864 |
| att tcc ttg aag gga gaa gaa gga atc atg ggc ttt cct gga ctg agg<br>Ile Ser Leu Lys Gly Glu Glu Gly Ile Met Gly Phe Pro Gly Leu Arg<br>290 295 300 | | 912 |
| ggt tac cct ggc ttg agt ggt gaa aaa gga tca cca gga cag aag gga<br>Gly Tyr Pro Gly Leu Ser Gly Glu Lys Gly Ser Pro Gly Gln Lys Gly<br>305 310 315 320 | | 960 |
| agc cga ggc ctg gat ggc tat caa ggg cct gat gga ccc cgg gga ccc<br>Ser Arg Gly Leu Asp Gly Tyr Gln Gly Pro Asp Gly Pro Arg Gly Pro<br>325 330 335 | | 1008 |
| aag gga gaa gcc gga gac cca ggg ccc cct gga cta cct gcc tac tcc<br>Lys Gly Glu Ala Gly Asp Pro Gly Pro Pro Gly Leu Pro Ala Tyr Ser<br>340 345 350 | | 1056 |
| cct cac cct tcc cta gca aaa ggt gcc aga ggt gac ccg gga ttc cca<br>Pro His Pro Ser Leu Ala Lys Gly Ala Arg Gly Asp Pro Gly Phe Pro<br>355 360 365 | | 1104 |
| ggg gcc caa ggg gag cca gga agc cag ggt gag cca gga gac ccg ggc<br>Gly Ala Gln Gly Glu Pro Gly Ser Gln Gly Glu Pro Gly Asp Pro Gly<br>370 375 380 | | 1152 |
| ctc cca ggt ccc cct ggc ctc tcc atc gga gat gga gat cag agg aga<br>Leu Pro Gly Pro Pro Gly Leu Ser Ile Gly Asp Gly Asp Gln Arg Arg<br>385 390 395 400 | | 1200 |
| ggc ctg ccg ggt gag atg gga ccc aag ggc ttc atc gga gac ccc ggc<br>Gly Leu Pro Gly Glu Met Gly Pro Lys Gly Phe Ile Gly Asp Pro Gly<br>405 410 415 | | 1248 |
| atc cct gcg ctc tac ggg ggc cca cct gga cct gat gga aag cga ggg<br>Ile Pro Ala Leu Tyr Gly Gly Pro Pro Gly Pro Asp Gly Lys Arg Gly<br>420 425 430 | | 1296 |
| cct cca gga ccc ccc ggg ctc cct gga cca cct gga cct gat ggc ttc<br>Pro Pro Gly Pro Pro Gly Leu Pro Gly Pro Pro Gly Pro Asp Gly Phe<br>435 440 445 | | 1344 |
| ctg ttt ggg ctg aaa gga gca aaa gga aga gca ggc ttc cct ggg ctt<br>Leu Phe Gly Leu Lys Gly Ala Lys Gly Arg Ala Gly Phe Pro Gly Leu<br>450 455 460 | | 1392 |
| ccc ggc tcc cct gga gcc cgc gga cca aag ggg tgg aaa ggt gac gct<br>Pro Gly Ser Pro Gly Ala Arg Gly Pro Lys Gly Trp Lys Gly Asp Ala<br>465 470 475 480 | | 1440 |
| ggg gaa tgc aga tgt aca gaa ggc gac gaa gct atc aaa ggt ctt ccg<br>Gly Glu Cys Arg Cys Thr Glu Gly Asp Glu Ala Ile Lys Gly Leu Pro<br>485 490 495 | | 1488 |

```
gga ctg cca gga ccc aag ggc ttc gca ggc atc aac ggg gag ccg ggg    1536
Gly Leu Pro Gly Pro Lys Gly Phe Ala Gly Ile Asn Gly Glu Pro Gly
            500                 505                 510 agg aaa ggg gac aga gga gac ccc ggc caa cac ggc ctc cct ggg ttc    1584
Arg Lys Gly Asp Arg Gly Asp Pro Gly Gln His Gly Leu Pro Gly Phe
        515                 520                 525 cca ggg ctc aag gga gtg cct ggc aac att ggt gct ccc gga ccc aaa    1632
Pro Gly Leu Lys Gly Val Pro Gly Asn Ile Gly Ala Pro Gly Pro Lys
    530                 535                 540 gga gca aaa gga gat tcc aga aca atc aca acc aaa ggt gag cgg gga    1680
Gly Ala Lys Gly Asp Ser Arg Thr Ile Thr Thr Lys Gly Glu Arg Gly
545                 550                 555                 560 cag ccc ggc gtc cca ggt gtg ccc ggg atg aaa ggt gac gat ggc agc    1728
Gln Pro Gly Val Pro Gly Val Pro Gly Met Lys Gly Asp Asp Gly Ser
            565                 570                 575 cca ggc cgc gat ggg ctc gat gga ttc ccc ggc ctc cca ggc cct ccc    1776
Pro Gly Arg Asp Gly Leu Asp Gly Phe Pro Gly Leu Pro Gly Pro Pro
        580                 585                 590 ggt gat ggc atc aag ggc cct cca ggg gac cca ggc tat cca gga ata    1824
Gly Asp Gly Ile Lys Gly Pro Pro Gly Asp Pro Gly Tyr Pro Gly Ile
    595                 600                 605 cct gga acg aag ggt act cca gga gaa atg ggc ccc cca gga ctg ggc    1872
Pro Gly Thr Lys Gly Thr Pro Gly Glu Met Gly Pro Pro Gly Leu Gly
610                 615                 620 ctt ccc ggc ctc aaa ggc caa cgt ggt ttc cct gga gac gcc ggc tta    1920
Leu Pro Gly Leu Lys Gly Gln Arg Gly Phe Pro Gly Asp Ala Gly Leu
625                 630                 635                 640 cct gga cca cca ggc ttc ctg ggc cct cct ggc ccc gca ggg acc cca    1968
Pro Gly Pro Pro Gly Phe Leu Gly Pro Pro Gly Pro Ala Gly Thr Pro
            645                 650                 655 gga caa ata gat tgt gac aca gat gtg aaa agg gcc gtt gga ggt gac    2016
Gly Gln Ile Asp Cys Asp Thr Asp Val Lys Arg Ala Val Gly Gly Asp
        660                 665                 670 aga cag gag gcc atc cag cca ggt tgc ata gga ggg ccc aag gga ttg    2064
Arg Gln Glu Ala Ile Gln Pro Gly Cys Ile Gly Gly Pro Lys Gly Leu
    675                 680                 685 cca ggc ctg cca gga ccc cca ggc ccc aca ggt gcc aaa ggc ctc cga    2112
Pro Gly Leu Pro Gly Pro Pro Gly Pro Thr Gly Ala Lys Gly Leu Arg
690                 695                 700 gga atc cca ggc ttc gca gga gct gat gga gga cca ggg ccc agg ggc    2160
Gly Ile Pro Gly Phe Ala Gly Ala Asp Gly Gly Pro Gly Pro Arg Gly
705                 710                 715                 720 ttg cca gga gac gca ggt cgt gaa ggg ttc cca gga ccc cca ggg ttc    2208
Leu Pro Gly Asp Ala Gly Arg Glu Gly Phe Pro Gly Pro Pro Gly Phe
            725                 730                 735 ata gga ccc cga gga tcc aaa ggt gca gtg ggc ctc cct ggc cca gat    2256
Ile Gly Pro Arg Gly Ser Lys Gly Ala Val Gly Leu Pro Gly Pro Asp
        740                 745                 750 gga tcc cca ggt ccc atc ggc ctg cca ggg cca gat ggg ccc cct ggg    2304
Gly Ser Pro Gly Pro Ile Gly Leu Pro Gly Pro Asp Gly Pro Pro Gly
    755                 760                 765 gaa agg ggc ctc cct gga gaa gtc ctg gga gct cag ccc ggg cca cgg    2352
Glu Arg Gly Leu Pro Gly Glu Val Leu Gly Ala Gln Pro Gly Pro Arg
770                 775                 780 gga gat gct ggt gtg cct gga cag cct ggg ctt aaa ggc ctt ccc gga    2400
Gly Asp Ala Gly Val Pro Gly Gln Pro Gly Leu Lys Gly Leu Pro Gly
785                 790                 795                 800 gac aga ggc ccc cct gga ttc aga gga agc caa ggg atg cct ggg atg    2448
Asp Arg Gly Pro Pro Gly Phe Arg Gly Ser Gln Gly Met Pro Gly Met
            805                 810                 815
```

-continued

| | |
|---|---|
| cca ggg ctg aag ggc cag cca ggc ctc cca gga cct tcc ggc cag cca<br>Pro Gly Leu Lys Gly Gln Pro Gly Leu Pro Gly Pro Ser Gly Gln Pro<br>820                        825                        830 | 2496 |
| ggc ctg tat ggg cct cca gga ctg cat gga ttc cca gga gct cct ggc<br>Gly Leu Tyr Gly Pro Pro Gly Leu His Gly Phe Pro Gly Ala Pro Gly<br>835                        840                        845 | 2544 |
| caa gag ggg ccc ttg ggg ctg cca gga atc cca ggc cgt gaa ggt ctg<br>Gln Glu Gly Pro Leu Gly Leu Pro Gly Ile Pro Gly Arg Glu Gly Leu<br>850                        855                        860 | 2592 |
| cct ggt gat aga ggg gac cct ggg gac aca ggc gct cct ggc cct gtg<br>Pro Gly Asp Arg Gly Asp Pro Gly Asp Thr Gly Ala Pro Gly Pro Val<br>865                        870                        875                        880 | 2640 |
| ggc atg aaa ggt ctc tct ggt gac aga gga gat gct ggc ttc aca ggg<br>Gly Met Lys Gly Leu Ser Gly Asp Arg Gly Asp Ala Gly Phe Thr Gly<br>885                        890                        895 | 2688 |
| gag caa ggc cat cca gga agc cct gga ttt aaa gga att gat gga atg<br>Glu Gln Gly His Pro Gly Ser Pro Gly Phe Lys Gly Ile Asp Gly Met<br>900                        905                        910 | 2736 |
| cct ggg acc ccc ggg cta aaa gga gat aga ggc tca cct ggg atg gat<br>Pro Gly Thr Pro Gly Leu Lys Gly Asp Arg Gly Ser Pro Gly Met Asp<br>915                        920                        925 | 2784 |
| ggt ttc caa ggc atg cct gga ctc aaa ggg aga ccc ggg ttt cca ggg<br>Gly Phe Gln Gly Met Pro Gly Leu Lys Gly Arg Pro Gly Phe Pro Gly<br>930                        935                        940 | 2832 |
| agc aaa ggc gag gct gga ttt ttc gga ata ccc ggt ctg aag ggt ctg<br>Ser Lys Gly Glu Ala Gly Phe Phe Gly Ile Pro Gly Leu Lys Gly Leu<br>945                        950                        955                        960 | 2880 |
| gct ggt gag cca ggt ttt aaa ggc agc cga ggg gac cct ggg ccc cca<br>Ala Gly Glu Pro Gly Phe Lys Gly Ser Arg Gly Asp Pro Gly Pro Pro<br>965                        970                        975 | 2928 |
| gga cca cct cct gtc atc ctg cca gga atg aaa gac att aaa gga gag<br>Gly Pro Pro Pro Val Ile Leu Pro Gly Met Lys Asp Ile Lys Gly Glu<br>980                        985                        990 | 2976 |
| aaa gga gat gaa ggg cct atg ggg ctg aaa gga tac ctg ggc gca aaa<br>Lys Gly Asp Glu Gly Pro Met Gly Leu Lys Gly Tyr Leu Gly Ala Lys<br>995                        1000                      1005 | 3024 |
| ggt atc caa gga atg cca ggc atc cca ggg ctg tca gga atc cct<br>Gly Ile Gln Gly Met Pro Gly Ile Pro Gly Leu Ser Gly Ile Pro<br>1010                      1015                      1020 | 3069 |
| ggg ctg cct ggg agg ccc ggc cac atc aaa gga gtc aag gga gac<br>Gly Leu Pro Gly Arg Pro Gly His Ile Lys Gly Val Lys Gly Asp<br>1025                      1030                      1035 | 3114 |
| atc gga gtc ccc ggc atc ccc ggt ttg cca gga ttc cct ggg gtg<br>Ile Gly Val Pro Gly Ile Pro Gly Leu Pro Gly Phe Pro Gly Val<br>1040                      1045                      1050 | 3159 |
| gct ggc ccc cct gga att acg gga ttc cca gga ttc ata gga agc<br>Ala Gly Pro Pro Gly Ile Thr Gly Phe Pro Gly Phe Ile Gly Ser<br>1055                      1060                      1065 | 3204 |
| cgg ggt gac aaa ggt gcc cca ggg aga gca ggc ctg tat ggc gag<br>Arg Gly Asp Lys Gly Ala Pro Gly Arg Ala Gly Leu Tyr Gly Glu<br>1070                      1075                      1080 | 3249 |
| att ggc gcg act ggt gat ttc ggt gac atc ggg gac act ata aat<br>Ile Gly Ala Thr Gly Asp Phe Gly Asp Ile Gly Asp Thr Ile Asn<br>1085                      1090                      1095 | 3294 |
| tta cca gga aga cca ggc ctg aag ggg gag cgg ggc acc act gga<br>Leu Pro Gly Arg Pro Gly Leu Lys Gly Glu Arg Gly Thr Thr Gly<br>1100                      1105                      1110 | 3339 |
| ata cca ggt ctg aag gga ttc ttt gga gag aag gga aca gaa ggt<br>Ile Pro Gly Leu Lys Gly Phe Phe Gly Glu Lys Gly Thr Glu Gly<br>1115                      1120                      1125 | 3384 |

```
gac atc ggc ttc cct ggg ata aca ggc gtg act gga gtc caa ggc    3429
Asp Ile Gly Phe Pro Gly Ile Thr Gly Val Thr Gly Val Gln Gly
    1130            1135                1140 cct cct gga ctt aaa gga caa aca ggc ttt cca ggg ctg act ggg    3474
Pro Pro Gly Leu Lys Gly Gln Thr Gly Phe Pro Gly Leu Thr Gly
    1145            1150                1155 cct cca ggg tcg cag gga gag ctg ggg cgg att gga ctg cct ggt    3519
Pro Pro Gly Ser Gln Gly Glu Leu Gly Arg Ile Gly Leu Pro Gly
    1160            1165                1170 ggc aaa gga gat gat ggc tgg ccg gga gct ccg ggc tta cca ggt    3564
Gly Lys Gly Asp Asp Gly Trp Pro Gly Ala Pro Gly Leu Pro Gly
    1175            1180                1185 ttt ccg gga ctc cgt ggg atc cgc ggc tta cac ggc ttg cca ggc    3609
Phe Pro Gly Leu Arg Gly Ile Arg Gly Leu His Gly Leu Pro Gly
    1190            1195                1200 acc aag ggc ttt cca gga tcc cca ggt tct gac atc cac gga gac    3654
Thr Lys Gly Phe Pro Gly Ser Pro Gly Ser Asp Ile His Gly Asp
    1205            1210                1215 cca ggc ttc cca ggc cct cct ggg gaa aga ggt gac cca gga gag    3699
Pro Gly Phe Pro Gly Pro Pro Gly Glu Arg Gly Asp Pro Gly Glu
    1220            1225                1230 gcc aac acc ctt cca ggc cct gtg gga gtc cca gga cag aaa gga    3744
Ala Asn Thr Leu Pro Gly Pro Val Gly Val Pro Gly Gln Lys Gly
    1235            1240                1245 gac caa gga gct cca ggg gaa cga ggc cca cct ggg agc cca gga    3789
Asp Gln Gly Ala Pro Gly Glu Arg Gly Pro Pro Gly Ser Pro Gly
    1250            1255                1260 ctt cag ggg ttc cca ggc atc aca ccc cct tcc aac atc tct ggg    3834
Leu Gln Gly Phe Pro Gly Ile Thr Pro Pro Ser Asn Ile Ser Gly
    1265            1270                1275 gca cct ggt gac aaa ggg gcg cca ggg ata ttt ggc ctg aaa ggt    3879
Ala Pro Gly Asp Lys Gly Ala Pro Gly Ile Phe Gly Leu Lys Gly
    1280            1285                1290 tat cgg ggc cca cca ggg cca cca ggt tct gct gct ctt cct gga    3924
Tyr Arg Gly Pro Pro Gly Pro Pro Gly Ser Ala Ala Leu Pro Gly
    1295            1300                1305 agc aaa ggt gac aca ggg aac cca gga gct cca gga acc cca ggg    3969
Ser Lys Gly Asp Thr Gly Asn Pro Gly Ala Pro Gly Thr Pro Gly
    1310            1315                1320 acc aaa gga tgg gcc ggg gac tcc ggg ccc cag ggc agg cct ggt    4014
Thr Lys Gly Trp Ala Gly Asp Ser Gly Pro Gln Gly Arg Pro Gly
    1325            1330                1335 gtg ttt ggt ctc cca gga gaa aaa ggg ccc agg ggt gaa caa ggc    4059
Val Phe Gly Leu Pro Gly Glu Lys Gly Pro Arg Gly Glu Gln Gly
    1340            1345                1350 ttc atg ggg aac act gga ccc acc ggg gcg gtg ggc gac aga ggc    4104
Phe Met Gly Asn Thr Gly Pro Thr Gly Ala Val Gly Asp Arg Gly
    1355            1360                1365 ccc aag gga ccc aag gga gac cca gga ttc cct ggt gcc ccc ggg    4149
Pro Lys Gly Pro Lys Gly Asp Pro Gly Phe Pro Gly Ala Pro Gly
    1370            1375                1380 act gtg gga gcc ccc ggg att gca gga atc ccc cag aag att gcc    4194
Thr Val Gly Ala Pro Gly Ile Ala Gly Ile Pro Gln Lys Ile Ala
    1385            1390                1395 gtc caa cca ggg aca gtg ggt ccc cag ggg agg cga ggc ccc cct    4239
Val Gln Pro Gly Thr Val Gly Pro Gln Gly Arg Arg Gly Pro Pro
    1400            1405                1410 ggg gca ccg ggg gag atg ggg ccc cag ggc ccc ccc gga gaa cca    4284
Gly Ala Pro Gly Glu Met Gly Pro Gln Gly Pro Pro Gly Glu Pro
```

|  |  |  |  |  |  |  |  |  |  |  |  |
|---|---|---|---|---|---|---|---|---|---|---|---|
| | | 1415 | | | 1420 | | | 1425 | | | |
| ggt | ttt | cgt | ggg | gct | cca | ggg | aaa | gct | ggg | ccc | caa | gga | aga | ggt | 4329 |
| Gly | Phe | Arg | Gly | Ala | Pro | Gly | Lys | Ala | Gly | Pro | Gln | Gly | Arg | Gly | |
| | | 1430 | | | 1435 | | | 1440 | | | | | | | |
| ggt | gtg | tct | gct | gtt | ccc | ggc | ttc | cgg | gga | gat | gaa | gga | ccc | ata | 4374 |
| Gly | Val | Ser | Ala | Val | Pro | Gly | Phe | Arg | Gly | Asp | Glu | Gly | Pro | Ile | |
| | | 1445 | | | 1450 | | | 1455 | | | | | | | |
| ggc | cac | cag | ggg | ccg | att | ggc | caa | gaa | ggt | gca | cca | ggc | cgt | cca | 4419 |
| Gly | His | Gln | Gly | Pro | Ile | Gly | Gln | Glu | Gly | Ala | Pro | Gly | Arg | Pro | |
| | | 1460 | | | 1465 | | | 1470 | | | | | | | |
| ggg | agc | ccg | ggc | ctg | ccg | ggt | atg | cca | ggc | cgc | agc | gtc | agc | atc | 4464 |
| Gly | Ser | Pro | Gly | Leu | Pro | Gly | Met | Pro | Gly | Arg | Ser | Val | Ser | Ile | |
| | | 1475 | | | 1480 | | | 1485 | | | | | | | |
| ggc | tac | ctc | ctg | gtg | aag | cac | agc | cag | acg | gac | cag | gag | ccc | atg | 4509 |
| Gly | Tyr | Leu | Leu | Val | Lys | His | Ser | Gln | Thr | Asp | Gln | Glu | Pro | Met | |
| | | 1490 | | | 1495 | | | 1500 | | | | | | | |
| tgc | cca | gtg | ggc | atg | aac | aaa | ctc | tgg | agt | gga | tac | agc | ctg | ctg | 4554 |
| Cys | Pro | Val | Gly | Met | Asn | Lys | Leu | Trp | Ser | Gly | Tyr | Ser | Leu | Leu | |
| | | 1505 | | | 1510 | | | 1515 | | | | | | | |
| tac | ttc | gag | ggc | cag | gag | aag | gcg | cac | aac | cag | gac | ctg | ggg | ctg | 4599 |
| Tyr | Phe | Glu | Gly | Gln | Glu | Lys | Ala | His | Asn | Gln | Asp | Leu | Gly | Leu | |
| | | 1520 | | | 1525 | | | 1530 | | | | | | | |
| gcg | ggc | tcc | tgc | ctg | gcg | cgg | ttc | agc | acc | atg | ccc | ttc | ctg | tac | 4644 |
| Ala | Gly | Ser | Cys | Leu | Ala | Arg | Phe | Ser | Thr | Met | Pro | Phe | Leu | Tyr | |
| | | 1535 | | | 1540 | | | 1545 | | | | | | | |
| tgc | aac | cct | ggt | gat | gtc | tgc | tac | tat | gcc | agc | cgg | aac | gac | aag | 4689 |
| Cys | Asn | Pro | Gly | Asp | Val | Cys | Tyr | Tyr | Ala | Ser | Arg | Asn | Asp | Lys | |
| | | 1550 | | | 1555 | | | 1560 | | | | | | | |
| tcc | tac | tgg | ctc | tct | acc | act | gcg | ccg | ctg | ccc | atg | atg | ccc | gtg | 4734 |
| Ser | Tyr | Trp | Leu | Ser | Thr | Thr | Ala | Pro | Leu | Pro | Met | Met | Pro | Val | |
| | | 1565 | | | 1570 | | | 1575 | | | | | | | |
| gcc | gag | gac | gag | atc | aag | ccc | tac | atc | agc | cgc | tgt | tct | gtg | tgt | 4779 |
| Ala | Glu | Asp | Glu | Ile | Lys | Pro | Tyr | Ile | Ser | Arg | Cys | Ser | Val | Cys | |
| | | 1580 | | | 1585 | | | 1590 | | | | | | | |
| gag | gcc | ccg | gcc | atc | gcc | atc | gcg | gtc | cac | agt | cag | gat | gtc | tcc | 4824 |
| Glu | Ala | Pro | Ala | Ile | Ala | Ile | Ala | Val | His | Ser | Gln | Asp | Val | Ser | |
| | | 1595 | | | 1600 | | | 1605 | | | | | | | |
| atc | cca | cac | tgc | cca | gct | ggg | tgg | cgg | agt | ttg | tgg | atc | gga | tat | 4869 |
| Ile | Pro | His | Cys | Pro | Ala | Gly | Trp | Arg | Ser | Leu | Trp | Ile | Gly | Tyr | |
| | | 1610 | | | 1615 | | | 1620 | | | | | | | |
| tcc | ttc | ctc | atg | cac | acg | gcg | gcg | gga | gac | gaa | ggc | ggt | ggc | caa | 4914 |
| Ser | Phe | Leu | Met | His | Thr | Ala | Ala | Gly | Asp | Glu | Gly | Gly | Gly | Gln | |
| | | 1625 | | | 1630 | | | 1635 | | | | | | | |
| tca | ctg | gtg | tca | ccg | ggc | agc | tgt | cta | gag | gac | ttc | cgc | gcc | aca | 4959 |
| Ser | Leu | Val | Ser | Pro | Gly | Ser | Cys | Leu | Glu | Asp | Phe | Arg | Ala | Thr | |
| | | 1640 | | | 1645 | | | 1650 | | | | | | | |
| cca | ttc | atc | gaa | tgc | aat | gga | ggc | cgc | ggc | acc | tgc | cac | tac | tac | 5004 |
| Pro | Phe | Ile | Glu | Cys | Asn | Gly | Gly | Arg | Gly | Thr | Cys | His | Tyr | Tyr | |
| | | 1655 | | | 1660 | | | 1665 | | | | | | | |
| gcc | aac | aag | tac | agc | ttc | tgg | ctg | acc | acc | att | ccc | gag | cag | agc | 5049 |
| Ala | Asn | Lys | Tyr | Ser | Phe | Trp | Leu | Thr | Thr | Ile | Pro | Glu | Gln | Ser | |
| | | 1670 | | | 1675 | | | 1680 | | | | | | | |
| ttc | cag | ggc | tcg | ccc | tcc | gcc | gac | acg | ctc | aag | gcc | ggc | ctc | atc | 5094 |
| Phe | Gln | Gly | Ser | Pro | Ser | Ala | Asp | Thr | Leu | Lys | Ala | Gly | Leu | Ile | |
| | | 1685 | | | 1690 | | | 1695 | | | | | | | |
| cgc | aca | cac | atc | agc | cgc | tgc | cag | gtg | tgc | atg | aag | aac | ctg | tga | 5139 |
| Arg | Thr | His | Ile | Ser | Arg | Cys | Gln | Val | Cys | Met | Lys | Asn | Leu | | |
| | | 1700 | | | 1705 | | | 1710 | | | | | | | |

```
<210> SEQ ID NO 2
<211> LENGTH: 1712
<212> TYPE: PRT
<213> ORGANISM: Homo sapiens

<400> SEQUENCE: 2

Met Gly Arg Asp Gln Arg Ala Val Ala Gly Pro Ala Leu Arg Arg Trp
1               5                   10                  15

Leu Leu Leu Gly Thr Val Thr Val Gly Phe Leu Ala Gln Ser Val Leu
            20                  25                  30

Ala Gly Val Lys Lys Phe Asp Val Pro Cys Gly Gly Arg Asp Cys Ser
        35                  40                  45

Gly Gly Cys Gln Cys Tyr Pro Glu Lys Gly Gly Arg Gly Gln Pro Gly
    50                  55                  60

Pro Val Gly Pro Gln Gly Tyr Asn Gly Pro Gly Leu Gln Gly Phe
65                  70                  75                  80

Pro Gly Leu Gln Gly Arg Lys Gly Asp Lys Gly Glu Arg Gly Ala Pro
                85                  90                  95

Gly Val Thr Gly Pro Lys Gly Asp Val Gly Ala Arg Gly Val Ser Gly
            100                 105                 110

Phe Pro Gly Ala Asp Gly Ile Pro Gly His Pro Gly Gln Gly Gly Pro
        115                 120                 125

Arg Gly Arg Pro Gly Tyr Asp Gly Cys Asn Gly Thr Gln Gly Asp Ser
    130                 135                 140

Gly Pro Gln Gly Pro Pro Gly Ser Glu Gly Phe Thr Gly Pro Pro Gly
145                 150                 155                 160

Pro Gln Gly Pro Lys Gly Gln Lys Gly Glu Pro Tyr Ala Leu Pro Lys
                165                 170                 175

Glu Glu Arg Asp Arg Tyr Arg Gly Glu Pro Gly Glu Pro Gly Leu Val
            180                 185                 190

Gly Phe Gln Gly Pro Pro Gly Arg Pro Gly His Val Gly Gln Met Gly
        195                 200                 205

Pro Val Gly Ala Pro Gly Arg Pro Gly Pro Pro Gly Pro Pro Gly Pro
    210                 215                 220

Lys Gly Gln Gln Gly Asn Arg Gly Leu Gly Phe Tyr Gly Val Lys Gly
225                 230                 235                 240

Glu Lys Gly Asp Val Gly Gln Pro Gly Pro Asn Gly Ile Pro Ser Asp
                245                 250                 255

Thr Leu His Pro Ile Ile Ala Pro Thr Gly Val Thr Phe His Pro Asp
            260                 265                 270

Gln Tyr Lys Gly Glu Lys Gly Ser Glu Gly Glu Pro Gly Ile Arg Gly
        275                 280                 285

Ile Ser Leu Lys Gly Glu Glu Gly Ile Met Gly Phe Pro Gly Leu Arg
    290                 295                 300

Gly Tyr Pro Gly Leu Ser Gly Glu Lys Gly Ser Pro Gly Gln Lys Gly
305                 310                 315                 320

Ser Arg Gly Leu Asp Gly Tyr Gln Gly Pro Asp Gly Pro Arg Gly Pro
                325                 330                 335

Lys Gly Glu Ala Gly Asp Pro Gly Pro Pro Gly Leu Pro Ala Tyr Ser
            340                 345                 350

Pro His Pro Ser Leu Ala Lys Gly Ala Arg Gly Asp Pro Gly Phe Pro
        355                 360                 365

Gly Ala Gln Gly Glu Pro Gly Ser Gln Gly Glu Pro Gly Asp Pro Gly
370                 375                 380
```

```
Leu Pro Gly Pro Pro Gly Leu Ser Ile Gly Asp Gly Asp Gln Arg Arg
385                 390                 395                 400

Gly Leu Pro Gly Glu Met Gly Pro Lys Gly Phe Ile Gly Asp Pro Gly
            405                 410                 415

Ile Pro Ala Leu Tyr Gly Gly Pro Pro Gly Pro Asp Gly Lys Arg Gly
                420                 425                 430

Pro Pro Gly Pro Pro Gly Leu Pro Gly Pro Pro Gly Pro Asp Gly Phe
            435                 440                 445

Leu Phe Gly Leu Lys Gly Ala Lys Gly Arg Ala Gly Phe Pro Gly Leu
        450                 455                 460

Pro Gly Ser Pro Gly Ala Arg Gly Pro Lys Gly Trp Lys Gly Asp Ala
465                 470                 475                 480

Gly Glu Cys Arg Cys Thr Glu Gly Asp Glu Ala Ile Lys Gly Leu Pro
                485                 490                 495

Gly Leu Pro Gly Pro Lys Gly Phe Ala Gly Ile Asn Gly Glu Pro Gly
            500                 505                 510

Arg Lys Gly Asp Arg Gly Asp Pro Gly Gln His Gly Leu Pro Gly Phe
        515                 520                 525

Pro Gly Leu Lys Gly Val Pro Gly Asn Ile Gly Ala Pro Gly Pro Lys
530                 535                 540

Gly Ala Lys Gly Asp Ser Arg Thr Ile Thr Thr Lys Gly Glu Arg Gly
545                 550                 555                 560

Gln Pro Gly Val Pro Gly Val Pro Gly Met Lys Gly Asp Asp Gly Ser
                565                 570                 575

Pro Gly Arg Asp Gly Leu Asp Gly Phe Pro Gly Leu Pro Gly Pro Pro
            580                 585                 590

Gly Asp Gly Ile Lys Gly Pro Pro Gly Asp Pro Gly Tyr Pro Gly Ile
        595                 600                 605

Pro Gly Thr Lys Gly Thr Pro Gly Glu Met Gly Pro Pro Gly Leu Gly
610                 615                 620

Leu Pro Gly Leu Lys Gly Gln Arg Gly Phe Pro Gly Asp Ala Gly Leu
625                 630                 635                 640

Pro Gly Pro Pro Gly Phe Leu Gly Pro Pro Gly Pro Ala Gly Thr Pro
                645                 650                 655

Gly Gln Ile Asp Cys Asp Thr Asp Val Lys Arg Ala Val Gly Gly Asp
            660                 665                 670

Arg Gln Glu Ala Ile Gln Pro Gly Cys Ile Gly Gly Pro Lys Gly Leu
        675                 680                 685

Pro Gly Leu Pro Gly Pro Pro Gly Pro Thr Gly Ala Lys Gly Leu Arg
690                 695                 700

Gly Ile Pro Gly Phe Ala Gly Ala Asp Gly Gly Pro Gly Pro Arg Gly
705                 710                 715                 720

Leu Pro Gly Asp Ala Gly Arg Glu Gly Phe Pro Gly Pro Pro Gly Phe
                725                 730                 735

Ile Gly Pro Arg Gly Ser Lys Gly Ala Val Gly Leu Pro Gly Pro Asp
            740                 745                 750

Gly Ser Pro Gly Pro Ile Gly Leu Pro Gly Pro Asp Gly Pro Pro Gly
        755                 760                 765

Glu Arg Gly Leu Pro Gly Glu Val Leu Gly Ala Gln Pro Gly Pro Arg
770                 775                 780

Gly Asp Ala Gly Val Pro Gly Gln Pro Gly Leu Lys Gly Leu Pro Gly
785                 790                 795                 800

Asp Arg Gly Pro Pro Gly Phe Arg Gly Ser Gln Gly Met Pro Gly Met
```

```
                     805                 810                 815
Pro Gly Leu Lys Gly Gln Pro Gly Leu Pro Gly Pro Ser Gly Gln Pro
                 820                 825                 830

Gly Leu Tyr Gly Pro Pro Gly Leu His Gly Phe Pro Gly Ala Pro Gly
                 835                 840                 845

Gln Glu Gly Pro Leu Gly Leu Pro Gly Ile Pro Gly Arg Glu Gly Leu
            850                 855                 860

Pro Gly Asp Arg Gly Asp Pro Gly Asp Thr Gly Ala Pro Gly Pro Val
865                 870                 875                 880

Gly Met Lys Gly Leu Ser Gly Asp Arg Gly Asp Ala Gly Phe Thr Gly
                885                 890                 895

Glu Gln Gly His Pro Gly Ser Pro Gly Phe Lys Gly Ile Asp Gly Met
                900                 905                 910

Pro Gly Thr Pro Gly Leu Lys Gly Asp Arg Gly Ser Pro Gly Met Asp
            915                 920                 925

Gly Phe Gln Gly Met Pro Gly Leu Lys Gly Arg Pro Gly Phe Pro Gly
        930                 935                 940

Ser Lys Gly Glu Ala Gly Phe Phe Gly Ile Pro Gly Leu Lys Gly Leu
945                 950                 955                 960

Ala Gly Glu Pro Gly Phe Lys Gly Ser Arg Gly Asp Pro Gly Pro Pro
                965                 970                 975

Gly Pro Pro Val Ile Leu Pro Gly Met Lys Asp Ile Lys Gly Glu
            980                 985                 990

Lys Gly Asp Glu Gly Pro Met Gly Leu Lys Gly Tyr Leu Gly Ala Lys
            995                 1000                1005

Gly Ile Gln Gly Met Pro Gly Ile Pro Gly Leu Ser Gly Ile Pro
    1010                1015                1020

Gly Leu Pro Gly Arg Pro Gly His Ile Lys Gly Val Lys Gly Asp
    1025                1030                1035

Ile Gly Val Pro Gly Ile Pro Gly Leu Pro Gly Phe Pro Gly Val
    1040                1045                1050

Ala Gly Pro Pro Gly Ile Thr Gly Phe Pro Gly Phe Ile Gly Ser
    1055                1060                1065

Arg Gly Asp Lys Gly Ala Pro Gly Arg Ala Gly Leu Tyr Gly Glu
    1070                1075                1080

Ile Gly Ala Thr Gly Asp Phe Gly Asp Ile Gly Asp Thr Ile Asn
    1085                1090                1095

Leu Pro Gly Arg Pro Gly Leu Lys Gly Glu Arg Gly Thr Thr Gly
    1100                1105                1110

Ile Pro Gly Leu Lys Gly Phe Phe Gly Glu Lys Gly Thr Glu Gly
    1115                1120                1125

Asp Ile Gly Phe Pro Gly Ile Thr Gly Val Thr Gly Val Gln Gly
    1130                1135                1140

Pro Pro Gly Leu Lys Gly Gln Thr Gly Phe Pro Gly Leu Thr Gly
    1145                1150                1155

Pro Pro Gly Ser Gln Gly Glu Leu Gly Arg Ile Gly Leu Pro Gly
    1160                1165                1170

Gly Lys Gly Asp Asp Gly Trp Pro Gly Ala Pro Gly Leu Pro Gly
    1175                1180                1185

Phe Pro Gly Leu Arg Gly Ile Arg Gly Leu His Gly Leu Pro Gly
    1190                1195                1200

Thr Lys Gly Phe Pro Gly Ser Pro Gly Ser Asp Ile His Gly Asp
    1205                1210                1215
```

-continued

```
Pro Gly Phe Pro Gly Pro Pro Gly Glu Arg Gly Asp Pro Gly Glu
1220            1225               1230

Ala Asn Thr Leu Pro Gly Pro Val Gly Val Pro Gly Gln Lys Gly
1235            1240               1245

Asp Gln Gly Ala Pro Gly Glu Arg Gly Pro Pro Gly Ser Pro Gly
1250            1255               1260

Leu Gln Gly Phe Pro Gly Ile Thr Pro Pro Ser Asn Ile Ser Gly
1265            1270               1275

Ala Pro Gly Asp Lys Gly Ala Pro Gly Ile Phe Gly Leu Lys Gly
1280            1285               1290

Tyr Arg Gly Pro Pro Gly Pro Pro Gly Ser Ala Ala Leu Pro Gly
1295            1300               1305

Ser Lys Gly Asp Thr Gly Asn Pro Gly Ala Pro Gly Thr Pro Gly
1310            1315               1320

Thr Lys Gly Trp Ala Gly Asp Ser Gly Pro Gln Gly Arg Pro Gly
1325            1330               1335

Val Phe Gly Leu Pro Gly Glu Lys Gly Pro Arg Gly Glu Gln Gly
1340            1345               1350

Phe Met Gly Asn Thr Gly Pro Thr Gly Ala Val Gly Asp Arg Gly
1355            1360               1365

Pro Lys Gly Pro Lys Gly Asp Pro Gly Phe Pro Gly Ala Pro Gly
1370            1375               1380

Thr Val Gly Ala Pro Gly Ile Ala Gly Ile Pro Gln Lys Ile Ala
1385            1390               1395

Val Gln Pro Gly Thr Val Gly Pro Gln Gly Arg Arg Gly Pro Pro
1400            1405               1410

Gly Ala Pro Gly Glu Met Gly Pro Gln Gly Pro Pro Gly Glu Pro
1415            1420               1425

Gly Phe Arg Gly Ala Pro Gly Lys Ala Gly Pro Gln Gly Arg Gly
1430            1435               1440

Gly Val Ser Ala Val Pro Gly Phe Arg Gly Asp Glu Gly Pro Ile
1445            1450               1455

Gly His Gln Gly Pro Ile Gly Gln Glu Gly Ala Pro Gly Arg Pro
1460            1465               1470

Gly Ser Pro Gly Leu Pro Gly Met Pro Gly Arg Ser Val Ser Ile
1475            1480               1485

Gly Tyr Leu Leu Val Lys His Ser Gln Thr Asp Gln Glu Pro Met
1490            1495               1500

Cys Pro Val Gly Met Asn Lys Leu Trp Ser Gly Tyr Ser Leu Leu
1505            1510               1515

Tyr Phe Glu Gly Gln Glu Lys Ala His Asn Gln Asp Leu Gly Leu
1520            1525               1530

Ala Gly Ser Cys Leu Ala Arg Phe Ser Thr Met Pro Phe Leu Tyr
1535            1540               1545

Cys Asn Pro Gly Asp Val Cys Tyr Tyr Ala Ser Arg Asn Asp Lys
1550            1555               1560

Ser Tyr Trp Leu Ser Thr Thr Ala Pro Leu Pro Met Met Pro Val
1565            1570               1575

Ala Glu Asp Glu Ile Lys Pro Tyr Ile Ser Arg Cys Ser Val Cys
1580            1585               1590

Glu Ala Pro Ala Ile Ala Ile Ala Val His Ser Gln Asp Val Ser
1595            1600               1605
```

| Ile | Pro | His | Cys | Pro | Ala | Gly | Trp | Arg | Ser | Leu | Trp | Ile | Gly | Tyr |
|---|---|---|---|---|---|---|---|---|---|---|---|---|---|---|
| 1610 | | | | 1615 | | | | | 1620 | | | | | |

| Ser | Phe | Leu | Met | His | Thr | Ala | Ala | Gly | Asp | Glu | Gly | Gly | Gly | Gln |
|---|---|---|---|---|---|---|---|---|---|---|---|---|---|---|
| 1625 | | | | | 1630 | | | | | 1635 | | | | |

| Ser | Leu | Val | Ser | Pro | Gly | Ser | Cys | Leu | Glu | Asp | Phe | Arg | Ala | Thr |
|---|---|---|---|---|---|---|---|---|---|---|---|---|---|---|
| 1640 | | | | | 1645 | | | | | 1650 | | | | |

| Pro | Phe | Ile | Glu | Cys | Asn | Gly | Arg | Gly | Thr | Cys | His | Tyr | Tyr |
|---|---|---|---|---|---|---|---|---|---|---|---|---|---|
| 1655 | | | | | 1660 | | | | | 1665 | | | | |

| Ala | Asn | Lys | Tyr | Ser | Phe | Trp | Leu | Thr | Thr | Ile | Pro | Glu | Gln | Ser |
|---|---|---|---|---|---|---|---|---|---|---|---|---|---|---|
| 1670 | | | | | 1675 | | | | | 1680 | | | | |

| Phe | Gln | Gly | Ser | Pro | Ser | Ala | Asp | Thr | Leu | Lys | Ala | Gly | Leu | Ile |
|---|---|---|---|---|---|---|---|---|---|---|---|---|---|---|
| 1685 | | | | | 1690 | | | | | 1695 | | | | |

| Arg | Thr | His | Ile | Ser | Arg | Cys | Gln | Val | Cys | Met | Lys | Asn | Leu |
|---|---|---|---|---|---|---|---|---|---|---|---|---|---|
| 1700 | | | | | 1705 | | | | | 1710 | | | | |

<210> SEQ ID NO 3
<211> LENGTH: 6264
<212> TYPE: DNA
<213> ORGANISM: Homo sapiens

<400> SEQUENCE: 3

```
gagtgtggct gcagtgcgcc gggacaccag ggctccgcgc tccgcactca agaggctccc      60
gcgtcccaac ccctcgcgcc cgcgcgttcg cggatccagg ccgaggaccg aaaggggccg     120
cccgagcccc cggggccggc gcccagagag cccagcaagg ccggccgccc tgccggtgtg     180
ccgccggcgg gtgcttctgg aagggccaat gcgttcgggc agcagcccct gaagccgagc     240
ccgaggctaa gtgggactga ccggggccca gagtggacga accgccagca tggggagaga     300
ccagcgcgcg gtggccggcc ctgccctacg gcggtggctg ctgctgggga cagtgaccgt     360
ggggttcctc gcccagagcg tcttggcggg tgtgaagaag tttgatgtgc cgtgtggagg     420
aagagattgc agtgggggct gccagtgcta ccctgagaaa ggtggacgtg gtcagcctgg     480
gccagtgggc ccccaggggt acaatgggcc accaggatta caaggattcc cgggactgca     540
gggacgtaaa ggagacaagg gtgaaagggg agccccgga gtaacgggac ccaagggcga     600
cgtgggagca agaggcgttt ctggattccc tggtgccgat ggaattcctg acacccgggg     660
gcaaggtggg cccaggggaa ggccgggcta cgatggctgc aacggaaccc agggagactc     720
aggtccacag gggcccccg ctctgaggg gttcaccggg cctcccggc ccaaggacc      780
aaaagggcag aaaggtgagc cttatgcact gcctaaagag gagcgcgaca gatatcgggg     840
tgaacctgga gagcctggat tggtcggttt ccagggacct cccggccgcc ctgggcatgt     900
gggacagatg ggtccagttg agctccagg agaccagga ccacctggac cccctggacc      960
aaaaggacag caaggcaaca gaggacttgg tttctacgga gttaagggtg aaaagggtga    1020
cgtagggcag ccgggaccca acgggattcc atcagacacc ctccacccca tcatcgcgcc    1080
cacaggagtc accttccacc cagatcagta caagggtgaa aaaggcagtg aggggaacc     1140
aggaataaga ggcatttcct tgaagggaga agaaggaatc atgggctttc ctggactgag    1200
gggttaccct ggcttgagtg gtgaaaaagg atcaccagga cagaagggaa gccgaggcct    1260
ggatggctat caagggcctg atggaccccg gggacccaag ggagaagccg agacccagg     1320
gccccctgga ctacctgcct actcccctca cccttcccta gcaaaaggtg ccagaggtga    1380
cccgggattc ccaggggccc aaggggagcc aggaagccag ggtgagccag agacccggg     1440
cctcccaggt ccccctggcc tctccatcgg agatggagat cagaggagag gcctgccggg    1500
```

```
tgagatggga cccaagggct tcatcggaga ccccggcatc cctgcgctct acggggcccc      1560
acctggacct gatggaaagc gagggcctcc aggaccccccc gggctccctg gaccacctgg     1620
acctgatggc ttcctgtttg ggctgaaagg agcaaaagga agagcaggct tccctgggct     1680
tcccggctcc cctggagccc gcggaccaaa ggggtggaaa ggtgacgctg gggaatgcag     1740
atgtacagaa ggcgacgaag ctatcaaagg tcttccggga ctgccaggac ccaagggctt     1800
cgcaggcatc aacggggagc cggggaggaa aggggacaga ggagacccccg ccaacacgg    1860 cctccctggg ttcccagggc tcaagggagt gcctggcaac attggtgctc ccggacccaa     1920
aggagcaaaa ggagattcca gaacaatcac aaccaaaggt gagcggggac agcccggcgt     1980
cccaggtgtg cccgggatga aggtgacga tggcagccca ggccgcgatg ggctcgatgg      2040
attccccggc ctcccaggcc ctccggtga tggcatcaag ggccctccag ggacccagg       2100 ctatccagga atacctggaa cgaagggtac tccaggagaa atgggccccc caggactggg     2160
ccttcccggc ctcaaaggcc aacgtggttt ccctggagac gccggcttac ctggaccacc     2220
aggcttcctg ggccctcctg gccccgcagg accccagga caaatagatt gtgacacaga     2280
tgtgaaaagg gccgttggag gtgacagaca ggaggccatc cagccaggtt gcataggagg     2340
gcccaaggga ttgccaggcc tgccaggacc cccaggcccc acaggtgcca aaggcctccg     2400
aggaatccca ggcttcgcag gagctgatgg aggaccaggg cccaggggct gccaggaga      2460 cgcaggtcgt gaagggttcc caggacccccc agggttcata ggaccccgag gatccaaagg     2520
tgcagtgggc ctccctggcc cagatggatc cccaggtccc atcggcctgc agggccaga     2580 tgggccccct ggggaagggg gcctccctgg agaagtcctg ggagctcagc ccgggccacg     2640
gggagatgct ggtgtgcctg gacagcctgg gcttaaaggc cttcccggag acagaggccc     2700
ccctggattc agaggaagcc aagggatgcc tgggatgcca gggctgaagg gccagccagg     2760
cctcccagga ccttccggcc agccaggcct gtatgggcct ccaggactgc atggattccc     2820
aggagctcct ggccaagagg ggcccttggg gctgccagga atcccaggcc gtgaaggtct     2880
gcctggtgat agagggacc ctggggacac aggcgctcct ggccctgtgg gcatgaaagg       2940
tctctctggt gacagaggag atgctggctt cacaggggag caaggccatc caggaagccc     3000
tggatttaaa ggaattgatg gaatgcctgg gaccccgggg ctaaaaggag atagaggctc     3060
acctgggatg gatggttttcc aaggcatgcc tggactcaaa gggagacccg gtttccagg     3120 gagcaaaggc gaggctggat ttttcggaat accggtctg aagggtctgg ctggtgagcc      3180
aggttttaaa ggcagccgag gggaccctgg gccccagga ccacctcctg tcatcctgcc      3240
aggaatgaaa gacattaaag gagagaaagg agatgaaggg cctatggggc tgaaaggata     3300
cctgggcgca aaaggtatcc aaggaatgcc aggcatccca gggctgtcag gaatccctgg     3360
gctgcctggg aggcccggcc acatcaaagg agtcaaggga gacatcggag tccccggcat     3420 ccccggttg ccaggattcc ctggggtggc tggccccccct ggaattacgg gattcccagg      3480
attcatagga agccggggtg acaaaggtgc cccaggagga gcaggcctgt atggcgagat     3540
tggcgcgact ggtgatttcg gtgacatcgg ggacactata aatttaccag gaagaccagg     3600
cctgaagggg gagcggggca ccactggaat accaggtctg aagggattct ttggagagaa     3660
gggaacagaa ggtgacatcg gcttccctgg gataacaggc gtgactggag tccaaggccc     3720
tcctggactt aaaggacaaa caggctttcc agggctgact gggcctccag gtcgcaggg      3780 agagctgggg cggattggac tgcctggtgg caaaggagat gatggctggc cgggagctcc     3840
gggcttacca ggttttccgg gactccgtgg gatccgcggc ttacacggct tgccaggcac     3900
```

```
caagggcttt ccaggatccc caggttctga catccacgga gacccaggct tcccaggccc    3960
tcctggggaa agaggtgacc caggagaggc aacacccctt ccaggccctg tgggagtccc    4020
aggacagaaa ggagaccaag gagctccagg ggaacgaggc ccacctggga gcccaggact    4080
tcaggggttc ccaggcatca cacccccttc aacatctct ggggcacctg gtgacaaagg     4140
ggcgccaggg atatttggcc tgaaaggtta tcggggccca ccagggccac caggttctgc    4200
tgctcttcct ggaagcaaag gtgacacagg gaacccagga gctccaggaa ccccagggac    4260
caaaggatgg gccggggact ccgggcccca gggcaggcct ggtgtgtttg gtctcccagg    4320
agaaaaaggg cccaggggtg aacaaggctt catggggaac actggaccca ccggggcggt    4380
gggcgacaga ggccccaagg gacccaaggg agacccagga ttccctggtg cccccgggac    4440
tgtgggagcc cccgggattg caggaatccc ccagaagatt gccgtccaac cagggacagt    4500
gggtccccag gggaggcgag gccccctgg ggcaccgggg gagatggggc cccagggccc    4560
ccccggagaa ccaggttttc gtggggctcc agggaaagct gggcccaag gaagaggtgg    4620
tgtgtctgct gttcccggct tccggggaga tgaaggaccc ataggccacc aggggccgat    4680
tggccaagaa ggtgcaccag gccgtccagg gagcccgggc ctgccgggta tgccaggccg    4740
cagcgtcagc atcggctacc tcctggtgaa gcacagccag acggaccagg agcccatgtg    4800
cccagtgggg atgaacaaac tctggagtgg atacagcctg ctgtacttcg agggccagga    4860
gaaggcgcac aaccaggacc tggggctggc gggctcctgc ctggcgcggt tcagcaccat    4920
gcccttcctg tactgcaacc ctggtgatgt ctgctactat gccagccgga acgacaagtc    4980
ctactggctc tctaccactg cgccgctgcc catgatgccc gtggccgagg acgagatcaa    5040
gccctacatc agccgctgtt ctgtgtgtga ggccccggcc atcgccatcg cggtccacag    5100
tcaggatgtc tccatcccac actgcccagc tgggtggcgg agtttgtgga tcggatattc    5160
cttcctcatg cacacggcgg cgggagacga aggcggtggc caatcactgg tgtcaccggg    5220
cagctgtcta gaggacttcc gcgccacacc attcatcgaa tgcaatggag gccgcggcac    5280
ctgccactac tacgccaaca gtacagcttc tggctgacc accattcccg agcagagctt    5340
ccagggctcg ccctccgccg acacgctcaa ggccggcctc atccgcacac acatcagccg    5400
ctgccaggtg tgcatgaaga acctgtgagc cggcgcgtgc caggaagggc cattttggtg    5460
cttattctta acttattacc tcaggtgcca acccaaaaat tggttttatt tttttcttaa    5520
aaaaaaaaa gtctaccaaa ggaatttgca tccagcagca gcacttagac ctgccagcca    5580
ctgtcaccga gcgggtgcaa gcactcgggg tccctggagg gcaagccctg cccacagaaa    5640
gccaggagca gccctggccc ccatcagccc tgctagacgc accgcctgaa ggcacagcta    5700
accacttcgc acacacccat gtaaccactg cactttccaa tgccacagac aactcacatt    5760
gttcaactcc cttctcgggg tgggacagac gagacaacag cacacaggca gccagccgtg    5820
gccagaggct cgaggggctc agggcctcag gcacccgtcc ccacgcgagg gccccgtggg    5880
tgggcctggc cctgctttct acgccaatgt tatgccagct ccatgttctc ccaaataccg    5940
ttgatgtgaa ttattttaaa ggcaaaaccg tgctctttat tttaaaaaac actgataatc    6000
acactgcggt aggtcattct tttgccacat ccctatagac cactgggttt ggcaaaactc    6060
aggcagaagt ggagacctt ctagacatca ttgtcagcct tgctacttga aggtacaccc    6120
catagggtcg gaggtgctgt ccccactgcc ccacgttgtc cctgagattt aaccctcca    6180
ctgctggggg tgagctgtac tcttctgact gcccctcct gtgtaacgac tacaaaataa    6240
```

```
aacttggttc tgaatatttt taaa                                      6264
```

<210> SEQ ID NO 4
<211> LENGTH: 1240
<212> TYPE: DNA
<213> ORGANISM: Homo sapiens

<400> SEQUENCE: 4

```
ttgttggcgc tgcccctcc cccccggcgg tgcgcgggcg gcgcctcaaa ggggaggacc    60
ctgcggcgcg ggtaagaggc ggcgggagcg cgcggcccgg gagtgtggct gcagtgcgcc  120
gggacaccag ggctccgcgc tccgcactca agaggctccc gcgtcccaac ccctcgcgcc  180
cgcgcgttcg cggatccagg ccgaggaccg aaaggggccg cccgagcccc cggggccggc  240
gcccagagag cccagcaagg ccggccgccc tgccggtgtg ccgccggcgg gtgcttctgg  300
aagggccaat gcgttcgggc agcagcccct gaagccgagc ccgaggtgag agcgaccccc  360
gagcggcgcc cagaccctgg cccgagagca ccgacttgga gcgccttgtg caggctaggg  420
ctgcacgctc tcctgcttgg gagtagaaag ggggaggtg ggagagcgaa gaccgagctc  480
ctcggccaag gagcacccac aggggcctaa cgggaggctc tccttctttc cgggtcgtgg  540
gggggacggc cctccggtca cccctgcatg cgggccgcgc accgcgctgt ccccgcgtct  600
cgcggaccga gaccggcggt gaggatgggc tgcctccctc atcctgcgct aaactcgctt  660
tgtctgtcgc ctctaggcta agtgggactg accggggccc agagtggacg aaccgccagc  720
atggggagag accagcgcgc ggtggccggc cctgccctac ggcggtaagc gactttctgc  780
ctggtccccg tgggtcacgc gcgcatggac ccttcggtgt aactctcggg gactgacaag  840
ccgggcccgc acgttcacgt ctctcttcct ccctttccca tgcaggtggc tgctgctggg  900
gacagtgacc gtggggttcc tcgcccagag cgtcttggcg gtaagtcctg gctcccgcgc  960
ttggacttgc gcgcccgaga gtggttggga cgtttgagtg gccttggaga aggcagctcg 1020
tccgtgcgct cccgagtgtg tgtgtgcgtg tggatgttcg ccaggctgcc caccaaggtt 1080
ctgagaaagc ttgctcttcc ctcatcatgc tttccaccTT tccttcccct tgggttccca 1140
gcgtcaatcc tgtgttttgc aagcgtcggc ctttcacggg aactgggaac ttaaaatgta 1200
gcctgaggca ccgttttcgt tgctttgggc aaagctgcag                      1240
```

<210> SEQ ID NO 5
<211> LENGTH: 681
<212> TYPE: DNA
<213> ORGANISM: Homo sapiens

<400> SEQUENCE: 5

```
ttgtaaccag catacaggtt ggttccaacc tgtacatcct ggtgcaggat gtcgatggtg    60
ggggatttca ggggtgggag agacaggggt atattggaaa tctctggacc ttacactcga  120
ttttgctgtg caccaaaaac tgctctaaaa attagtctat ttttttaaaa aagccttatt  180
gaatgttttg aatgaatcgt ttctagagtt ggaaggattc tcaacagatg atattttaat  240
acatgttgta gttggcaatg tttaggtaac ttttctttgc cttgtgtttt attgttgcag  300
ggtgtgaaga gtttgatgt gccgtgtgga ggaagagatt gcagtggggg ctgccagtgc  360
taccctgaga aggtggacg tgtaagtcac agcattgcaa taaataatat tatcttcctc  420
atacagtcat gcctcgctta caacgggggt accttctggg acacgtgtgg ctgggcagtt  480
tcatcattgc ttgaacatac tggagagtac tcacacaaac ctagatggcc gggcctacta  540
cacacccggc tgtgtgataa agcctgttgc tactaggcta caaacctgta cgtaggcagt  600
```

```
tgcgacacag tactatttgt atatctaaat acagaaaagg tacagtaaaa agaaagtaaa    660
aagatgtaaa atgggactcc t                                             681

<210> SEQ ID NO 6
<211> LENGTH: 864
<212> TYPE: DNA
<213> ORGANISM: Homo sapiens

<400> SEQUENCE: 6
cttaaaaaga acccaaataa gttaattctt tcatcccaac ccagtattat catttcacaa    60
tgacatgact ttagtaattt aggataattt ttttctcaca ttccatattt tctcttctta   120
aactctatga cttcttttgt tagctatcat ggcagtagat gatagtttac atataatgtt   180
ccctgtagat tatagctctt taaaaacaaa aaaaaaaatg tagttttgaa agtaaccgta   240
actgatcatg agtatgtatt gtgattaatc gtggaaattg aacctttgtt gttcccacag   300
ggtcagcctg ggccagtggg ccccaggggt acaatgggc caccaggatt acaaggattc    360
ccgggactgc agggacgtaa aggagacaag ggtgaaaggg gagccccgg agtaacggga    420 cccaagggcg acgtggtacg caccgctggt gtattcccct ggcctcatga gggtggcggg   480
tatctcagcc ttggttaatt gcatttgctt tcttcatagg gagcaagagg cgtttctgga   540
ttccctggtg ccgatggaat tcctgtaagt tttatggaag actggaattt taaaacattg   600
cgtgcatcct aggcaataca ttttgtgact taaagaaaca ttttgaatga gacctccttt   660
tttgtttatg acataaaaca cgtggggact atacgtgcgt attctccccg cggaattcag   720
tcagacagtg aacaaattgt ttgctttgta aacgtcctta tagacttggc ttcagaattg   780
agacgatttt gctaaactgc acattgtttg gtaataaaaa gctagagtgc tgtccagata   840
ctcgccctaa agagccagtc ttgt                                          864

<210> SEQ ID NO 7
<211> LENGTH: 717
<212> TYPE: DNA
<213> ORGANISM: Homo sapiens

<400> SEQUENCE: 7
gtccctgctg atagacagtc actcaactag taagacagaa gaaaccccga cagtgtactt    60
cttacccaag cccaggtgaa gcagaacttt gcttcgaaat cttttccctg cttagaacga   120
taccttatgc cttcacttat ttaatctttc attcattcat tgttcacttt ttgaggtgtc   180
ttttccttgg attcatgccg ggaacatggc ttatgagaat ataagactgt tttatctcac   240
agttacatga caactagaag cctgctggtt ggctgattct ctcactgctc tctttcccag   300
ggacacccgg ggcaaggtgg gcccagggga aggccgggct acgatggctg caacggaacc   360
cagggagact caggtccaca ggggcccccc ggctctgagg ggttcaccgg gcctcccgtg   420
agtatcccca cagcgcctgt gctccaggga cgggcagacc cctgctaagc cctgccttta   480
taacctgggg gagcctcccg ctcactgtgg ccagaacgga agcataactg tatgttgacg   540
cccaagacat gacgtttctg gattcaagta acttcatttt tcgtattctt taaatgttag   600
atagaaaatc attgttgtgg ttgatgttgt tcactctcag tctcccaagt gtcacttcat   660
tttctcccaa attctcatgc gtaatagtgg aatcgtaaac gcaaattaaa aagctga     717

<210> SEQ ID NO 8
<211> LENGTH: 1323
<212> TYPE: DNA
```

<213> ORGANISM: Homo sapiens

<400> SEQUENCE: 8

```
cattggcata ctagagggtt ggttgacaga gcattcattt gggttttgaa aataatttaa      60
atcctaaagt atttctgttt taactctagg aaagatatga ttgggtcaat aggaaattaa     120
aggtcttacc cttgttgctg aatatagggt tggtgttcag ataacccccc atcagccata     180
agaacaatta gaccttgccc acaaaagtca atgttcagtc atccacatta ccatagctgc     240
accgaatgtt aatggactct ttttgttgtt ttttcttttt acaatatatc tgctaattag     300
gggccccaag gaccaaaagg gcagaaaggt gagccttatg cactgcctaa agaggagcgc     360
gacagatatc gggtacgttt gcaagagatg ggaggggtaa tgaagggacc cagtgtaaat     420
tctcaactaa caaagttaat tgccaagtga actttgcatg taagaatgaa tgtactgaag     480
gcatgcctag aatggcggca taatctaaaa gtcatcttac ttccgatcag gatgttttca     540
atcttatttt taattgtgtg tttatctctt tcccatattc acaatactcc aagccaaatt     600
agtacttgta gttaatatta gtaaatatta atattactaa aatatattct gactaaataa     660
caatattagt aaaaattaat attagtaaat taacattact aggtcctgat agggctgatc     720
tgtttgatat gcttatttcc aactctgcaa taaaaggtaa gtaaatcaa agatggttaa     780
aagctatcac tcttaaaatt atttcttctc cattagggtg aacctggaga gcctggattg     840
gtcggtttcc aggtaagttt attttttattg gacgatattc caaacaaaag tttaagagct     900
tcagaactcc aagtaccagt ttacctctct taaaaacatt ctcccgctgc ctatccatag     960
ggacctcccg gccgccctgg gcatgtggga cagatgggtc cagttggagc tccagggaga    1020
ccagtaagta cctggacaca ggtgcccact ctgggaccat cgtccggtca tcccttccag    1080
atgccacttc ttcaatggtt gactccagat gagagcttta agaacaacta tgatgcttat    1140
aggcgtagca gagaacatca agacaaaacg gaccattcct tgcacacttt gctgctgtta    1200
aggttgaaga ataagggctt aaaattatgg tcaccagctc tctgccagtt atgtcaaatt    1260
ttgacttggt tccggcaggg tgcccttcca tccccacccc atacctaccc agtgacagac    1320
agc                                                                  1323
```

<210> SEQ ID NO 9
<211> LENGTH: 636
<212> TYPE: DNA
<213> ORGANISM: Homo sapiens

<400> SEQUENCE: 9

```
cttgcaaagg gatcagaaca aacacagaga ggacatgggt gaagtcaaaa gcccaaacac      60
acaaaagcaa agcagaaaca gctgtccgta gacagccggc agattctgag aactggagct     120
gacccgagtc cctctccccc agcatgtcat ctctgccaag ccaaatgcat cagaaacctc     180
catgcatcct acactgtgtc ctaaatatac agtcaatggc tttcccagag ctttccacca     240
gatgttatct gggtcctggg gtaaagaaaa ccatttacac atttctttgt atttgtacag     300
ggaccacctg gaccccctgg accaaaagga cagcaagtaa gttggttttg ggggtgagg     360
atgagggaag ggggtactta ggtgtttgtg ggtttgtttg ttttttacca taaaacttct     420
tggttggcaa ctatttattg tttatattat gatgaaaaca gttttggagg tttttaagac     480
ttaatgttaa actccaagga tagatccatg gtgcctctgg acattaaaaa agtaaacagg     540
tggaatgatt tgttgtttgc aaattaatta ccacatgcct gttggtatat gaaaaccaca     600
ctgaggaaca tttgattgaa acgaagatta gaacaa                              636
```

<210> SEQ ID NO 10
<211> LENGTH: 642
<212> TYPE: DNA
<213> ORGANISM: Homo sapiens

<400> SEQUENCE: 10

```
ccagaaccca gggacatgct cttagactac agtctgcaga gaccatatac tcacgatcga      60
gggccagcac cacctggggt ccaatctcag ctcccactca ttcactctga ggccttggtc     120
aactgacatg acaaactgtc aattagtttc tacaatgcaa agcaagaata ttatgcaaat     180
atagttgctc agtaaagttg ccgataaata ggccttgggt ttcttttttct aagaaaaata    240
attttatttc tctctgatta ttggcttttt aaaacttaca gaattatttt atcttttcag     300
ggcaacagag gacttggttt ctacggagtt aagggtgaaa aggtaaagga agcctggtca     360
attccagcag aggcatgcag catttctcag ccaggaaata aatcatttta attactaagt     420
tctgtgctgt aaaacttttta ccttgagttg atctgcagac agaccatttg catagggaaa     480
taatcattgc aaagtgctag gttgtcacct acataccagt gataattctg catcaacaag     540
acggtaaaca tagaccatct aggctagccg agactctgac acagagacat aagctcagct     600
catcttcaga aggtggaggt gaggacatgt cactgagtgc at                        642
```

<210> SEQ ID NO 11
<211> LENGTH: 699
<212> TYPE: DNA
<213> ORGANISM: Homo sapiens

<400> SEQUENCE: 11

```
cccatatata gaaattcatt gtaaggaaac aaccccacag aaacaaatgc agtccagaat      60
tgtaaacaac ctacatggct tttatgcata aattctaaat gattgctaat gaaaggagga    120
tataaaaaac ttacattagg attactctat tttgtggtta ttatactgta aataggtata    180
catatggtaa gtaatatgca acattaaaa ctgcagtatt ttggccaggt tgtatttgta      240
ttcgagtttt gtagtttcct ttcgatttaa agacaactgc ttttgcttaa caatatgcag    300
ggtgacgtag ggcagccggg acccaacggg attccatcag acaccctcca ccccatcatc    360
gcgcccacag gagtcacctt ccacccagat cagtacaagg taaagagcaa aattgactct    420
tttcatagtt gaaataaaaa aaggagagta aaagtacatt tcttcaattg tattcaacca    480
cattccaagt agaaaaagcc tcaccaccaa cttggcacat tacccatgaa aacataaccg    540
ggtcctccca gaatgttttc aactcttcca gacggttact agattcacag tgcgatcccg    600
tcgtcagtcc atcatctcaa ttctgatgaa tctgaagcaa caagagaatt catttaaaaa    660
aaaacttata tctatcctta cattcagtgt aggtggagg                           699
```

<210> SEQ ID NO 12
<211> LENGTH: 1267
<212> TYPE: DNA
<213> ORGANISM: Homo sapiens

<400> SEQUENCE: 12

```
acatctgcct ggaacggtgt gggggataaa ggaaaacaga gagaaggaaa gacagacttt      60
cacttgtacc aagaggaata caggaattaa tttatcttgt gaaaatctag aagaaatgac    120
acctcttttc tcttgaattt tgaagctgca aaatttaaga gtcatgtgtt gtaatcaatt    180
tatgatgatt gtgtgaggat tgattcagta ctttcagctc atgtcatgaa ccctgattga    240
```

| | |
|---|---:|
| tttttacccca ttaccatcct caaattaata agcgtttctt attttttcata ttcttcacag | 300 |
| ggtgaaaaag gcagtgaggg ggaaccagga ataagagtaa gtcgagtaat gagcatgccc | 360 |
| cctcccctgt ggctcctggg ctgtcggcgc tctgccaggc atgacggggt gcaccatgcg | 420 |
| ctcggggccc gcacaccgcc agtctctcat cccttgtcc atagcagaac agtattagca | 480 |
| tgcatttta cactgtattt taagaagtca gttctagaat ttcttcctct tggcatcata | 540 |
| aacactggct aatcatcttc tgaggtttgg gaagggagca tggagatggc ggaggggcgt | 600 |
| ggcttccact caggcgccac cgggttctgc cctccgtccc ctctgtcact gcctgtcctc | 660 |
| agagctccag ctctccctcg cggtcgctta ccacgtgaca tgacacatgc agtcctggat | 720 |
| gggtgacagc ccgggaaggc tggcgggtct cctaggaccg tgccctgcac tgcgcctgag | 780 |
| ttgagcatcg ccaggcggtc tggacaccat cggggctgag aacacagagt cctggagcag | 840 |
| aggatgacac gtgggccctg ttggctggag gggccgcccc tgggttgctc cttacgcccc | 900 |
| ctctgctctc tcctagggca tttccttgaa gggagaagaa ggaatcatgg gctttcctgg | 960 |
| actgagggta aaccacgcct tttataactg cagttgtcgg tttggtttgg ttttttttcag | 1020 |
| taggcttttcc ttttagagc tgtttcagat tcacagcaaa atttagcaga aagtatagag | 1080 |
| atttcccgtt attactcccc accccccccc acacacacac acagcagccc cccagcacga | 1140 |
| acatctagca ctggggctg cgctggctac aatccgtgaa ccatcttgac acaccgtctt | 1200 |
| cacccagcag caggtgtgca gacgcggccc tccccgtgga ggaggcgcga gtaccgcaca | 1260 |
| aaacctt | 1267 |

<210> SEQ ID NO 13
<211> LENGTH: 645
<212> TYPE: DNA
<213> ORGANISM: Homo sapiens

<400> SEQUENCE: 13

| | |
|---|---:|
| cgtcttccac agggaagcag ctttgagatt aggatggatt ctgctttctt cgagcctttt | 60 |
| tatcatagtc attatttccc atccccacct ccccacaact ttgtaaaggg gaaagaattg | 120 |
| tattaatagt tggtattgaa tttggcaatt tgttgctatt cttcaaaatc tggacctgag | 180 |
| acttgttcaa tctgtccatc ggcattttgc tgtgatcaca gccaggtgcc gtagtcaagc | 240 |
| cctctggaaa tgtctactgc atattctgag ctgtttgctt ctgttttttg ttcattccag | 300 |
| ggttaccctg gcttgagtgg tgaaaaagga tcaccaggac agaaggtaag ttggatgcat | 360 |
| gaactgcagt ctgctctggg cccacgacat cccacagagg ttaaataaat aggccttggc | 420 |
| atctcaggaa agaaaattgt ctccagaaaa aaacattgaa aatggttctt gtatttgcag | 480 |
| tcacaaagat aatcctgcct cacaatactt gaaccgggtc attaccttgg ctctcattt | 540 |
| tgcaaactat cttttgcttc ctccctttca aagtgtccgt cactcgaccc caccagccat | 600 |
| ggtttctata tcgtccaacc tcacacccct cctccatgtc cttgt | 645 |

<210> SEQ ID NO 14
<211> LENGTH: 654
<212> TYPE: DNA
<213> ORGANISM: Homo sapiens

<400> SEQUENCE: 14

| | |
|---|---:|
| acaaccacaa aatgatacta aaaacataga aaggaagaag ggactattgt gaattaagtg | 60 |
| agaattcaga ggcatagcat ccaagtgtta tatttggact tttttggctc ctggttctag | 120 |
| caaagcaacc ttaaaaagac attttgaga cccaagtcag ggaaaattga gcacagactg | 180 |

```
ggttaataca tgactttaat aaactgttgt tcattttgtg agatataata atgccattgc    240
agtccctttt tggagttata catcagagac aaaaattaaa agcaaatatc tttcttgcag    300
ggaagccgag gcctggatgg ctatcaaggg cctgatggac cccggggacc caaggtgagc    360
ccgtttctca tgtctttgcc acttatggtg tctcgcccac cctggctggc cttactcccc    420
tcttgatggt gtcctgtgga ggcatcccct gccctaaaaa gtacaagatc cccaaataca    480
cggcctctga cactgacag acgaggtgga tggtgaccta cgagccacgt gtgctccctg     540
ccagggagaa gggtgccacc tgccactcag ggccacgtag gggtgcgctc aggcacagag    600
gaagccagca gccctgggga aggcaggcct tgtagtaaca agagggtgcg gtgc          654
```

<210> SEQ ID NO 15
<211> LENGTH: 667
<212> TYPE: DNA
<213> ORGANISM: Homo sapiens

<400> SEQUENCE: 15

```
atgtaatagt ctgaactaca gaaagcacag tctcctggca ttcgacaagg atttcaaaat     60
gagatgagcc cctgcctgtc ttgttctctt tgggcacctg tggctggtgg ctgggatgcc    120
aggctctgcc accctagcat ggggatgctg ccccaggcac tgtctgtggt tccactggtt    180
gaaatagctg ctctgccagc ctgacggtcc acgctcgggt ttcttctttg gaaatatgtg    240
tactgtcaaa aactccaaaa ggctattctc acatcctgtt tttctctttt ctttctctag    300
ggagaagccg gagacccagg gcccctggga ctacctgcct actcccctca cccttcccta    360
gcaaaaggtg tgtgaacaat ttcacctgca tagttcagca tcgcatacac attctctcct    420
gttagggaca cagagctatg aactttcaag acagatattc taagcaaccc taaaacttaa    480
agtataataa taataaaaaa aataaaaaat aaaccacgaa atttagaaca taacttcatg    540
tacaatttcc ctcatgctta aatgtgtcac agggagacct tcatgttgcc tgtgcctgag    600
acagtcctca ccacctacac gtgagaaatc ccctccgttg gggaattctt tcacttctgc    660
ttaactt                                                              667
```

<210> SEQ ID NO 16
<211> LENGTH: 1376
<212> TYPE: DNA
<213> ORGANISM: Homo sapiens

<400> SEQUENCE: 16

```
aagtgaggcc tcctcgctcc caggccacca gcagaattgg caaccacatt agttccttct     60
ttattcgagc tttggactca cctacttcct cacccggttt tcactaatcc tgttcccctg    120
ctggagaatg agcccttaa aaagagagac caccccatgt attaatcatc ttaactcctc     180
atcaggccgc atacagcata tggagcattt ggtaaatatg tagtcaatga aaaagtgaac    240
gccagctgcg atccgtagac cacggtcttg ttccttactgt gggacttgtt tcccttccag    300
gtgccagagg tgacccggga ttcccagggg cccaagggga gccaggaagc cagggtgagc    360
caggagaccc gggcctccca ggtccccctg gcctctccat cggagatgga ggtaatgtgg    420
cttcataata tcaacaccgg agacccaaag cacctgcact caggtcctag cacacacaag    480
ggagacttcg ttgacgacgt agctatgtcg ttgttacttt tccccactga ctagtcttag    540
cagctctaag gagcccgcca cacatgcttt ggacaccttc acagaaccct cgcacatatg    600
acagtaactc cccaactagg ttagatggtg ccacgatggg taactggcat gcttccacct    660
```

```
gtgggttggg aagagaacgg agaatcatca ggtgttgttg cccagtgttg atcacaacta    720
tcaagccatt atttgagggg caaggagagg ggtgttttta atgttgaaaa aggataatga    780
actataccaa tggcttctac ccatcggagt tattgacggg gccatgaagc ccgctagtgc    840
cccagtgggc ccctctggac acgaacacaa aggcagcggt gtggtatggg agactcacgc    900
tgcaggtgaa tgctgtttgg tttcagatca gaggagaggc ctgccgggtg agatgggacc    960
caagggcttc atcggagacc ccggcatccc tgcgctctac gggggcccac ctggacctga   1020
tggaaagcga gggcctccag gacccccgg gctccctgga ccacctggac ctgatggtga   1080
gtggagggaa acaaaaggga gggtgtagcc taatgttcag atgaagcccg gtcccagccg   1140
gatgttattt gggattctct gctaaatgac tctgggaacg aatccagtag gccagtgatt   1200
agggtgcagt ggatccaggt agattagggt gtagtgggtg ctctctgggg tccacgcagg   1260
agctggggat ggaagctgaa gccctgtaag cctgtgagta tcacagcccc gtggatgcca   1320
cacagtgagg tttagttgct gcagcttcgg tgaaatccat ccttcagcga aacatc       1376
```

<210> SEQ ID NO 17
<211> LENGTH: 693
<212> TYPE: DNA
<213> ORGANISM: Homo sapiens

<400> SEQUENCE: 17

```
cccaggcgtc cgtggggctg atgccctgcg tctgcgtggg accccaggcg tccgtggggc     60
tgatgccgtg catctgcgtg ggaccccagg cgtcgtgggg ctgatgccgt gcgtctgcgt    120
gggaccccag gcgtccgtgg ggctgatgcc ctgcgtctgc gtgggacccc aggcgtccgt    180
ggggctgatg ccctgcgtct gcgtgggacc ccaggcgtcc gtggggctga tgccctgcgt    240
ctgcgtggga ccccaggcgt ccgtgggget catgccctgc atctgtggtt gtctctctag    300
gcttcctgtt tgggctgaaa ggagcaaaag gaagagcagg cttccctggg cttcccggct    360
cccctggagc ccgcggacca aaggggtgga aaggtaagaa catctgggag ggacgggatg    420
aggacagcct ggccttttcca agtccctcac cttacagaag gtgaaatcca tccccccactc   480 acgtgtttgg acatgaaaat gagcctgcat gtctctccca gcctcctgtc cccttggcgg    540
tggcactgag agggaggcgc atggagccag tggtgctgtc tgagcactcg gcccccaggc    600
tcaccgtccc tgctctccat ctgccatcct cgtcactgac cttcctagca gcagtgagcc    660
tgatgctgag tcctgtgctg ggttaaaagg gaa                                 693
```

<210> SEQ ID NO 18
<211> LENGTH: 764
<212> TYPE: DNA
<213> ORGANISM: Homo sapiens

<400> SEQUENCE: 18

```
tccttcacac tccccgcaac tcaacctatg cctctgaatg tggtcccagt ttttaagtat     60
ctttagtaaa catcagagtc aaattctgaa ccccatgaga ctatgagtga acacttgagt    120
cacttagtct gagcctcagt tttcccatct aagaaatggg ggtcatagtg cccatcagaa    180
caggcagtgt cctaaaagca ccaagtgtgc cacccagctc tccccgctgc ctgataccc    240 tctccccgcc acgctaagag gaatgcggaa caaggaggcc ctcctctccc tcctctgcag    300
gtgacgctgg ggaatgcaga tgtacagaag gcgacgaagc tatcaaaggt cttccgggac    360
tgccaggacc caagggcttc gcaggcatca acggggagcc ggggaggaaa ggggacagag    420
gagaccccgg ccaacacggc ctccctgggt tcccagggct caaggtgagg agcaatttca    480
```

```
tcatgaagct ggcaagacac tctgaggcct ccccaggtgt cccgttcttg ccttttatct    540
cctaagttta cacagcttca gaccggcaac actcatggac ccaaggcatg gctaaaccat    600
tctaaaaacc cacataccc aaggcggact ttctacatgt ccactggtga gactgagaag     660
gggcgctgct gtgggaaccg cagccgacag ctcttgaaag agttcaatag ggggtcacca    720
cgtgacccag aaatgccact cctggtgtat ccccaagaga cttg                    764
```

<210> SEQ ID NO 19
<211> LENGTH: 871
<212> TYPE: DNA
<213> ORGANISM: Homo sapiens

<400> SEQUENCE: 19

```
agtgaatcac cgcgcccggc cacattgtaa ttatttaaaa ttaaagaaaa ggtaccatcc     60
agttcctcag tcccaccatc cgcagttcca gtgctccaca gccactgtgg ccagtggccc    120
cacactggac agctggatgg gggcgtatcc agcatcgcag aaagtgctcc ttgggtggcg    180
ctcggtttgg tgacgggtga ctgcctgcca gctgtgtgag atgaaaaagc ttgccagcca    240
tcttctcaga tgccctcaca gtacaaagaa ggaagatatt tttttgtctg ttttccacag    300
ggagtgcctg gcaacattgg tgctcccgga cccaaggag caaaaggaga ttccagaaca     360
atcacaacca aggtgagtt cctctctggc cacgcggccc ctggggcact gagccttcct    420
gtgggcacct gcctgggcag cttcacatgc aaatccttt ctaggtgagc ggggacagcc     480
cggcgtccca ggtgtgcccg ggatgaaagg tgacgatggc agcccaggcc gcgatgggct    540
cgatggattc cccggcctcc caggccctcc cgtgagtagc cacaaactgc ggcagctccg    600
tcctctcttc ttcatccttc aggttctcca aacaccccag aagcaaacag tattgacatg    660
agcactaaac caacctgtgc ataggacagg ctgctcattc tgctcattct atttctaatg    720
agcagaaatc agacttttta ggaaacggtg aattaagtta gaagccaagc tccaaatgaa    780
catttaaaag tcaacaatca aagaaatatt cctcctggtg taacagacta agaaccctcc    840
cccgccaaaa aaagtagact attctaaaat g                                  871
```

<210> SEQ ID NO 20
<211> LENGTH: 1258
<212> TYPE: DNA
<213> ORGANISM: Homo sapiens

<400> SEQUENCE: 20

```
ttctggagat gaaggcccag gctgatgcag gggagctggc gggtgggaag agagaaatgc     60
tcaagcatgt acatgtgcct tccagaaccg gcttccgtgg cattgcttag actgctacac    120
agtctgtcac tggctcctgt gacctggctg accatggcac taggttcctg ttcatctctg    180
ttgtctttct gttctggatc catagctcag aattccggga aatgggaaag gaaacaggga    240
agtcgaggcg atctttaaca ttagtatata ttttaagaaa taaactgaat tttcacacag    300
ggtgatggca tcaagggccc tccaggggac ccaggctatc caggaatacc tggaacgaag    360
ggtactccag gagaaatggg cccccaggga ctgggccttc ccggcctcaa aggccaacgt    420
ggtttccctg gagacgccgg cttacctgga ccaccaggct cctgggccc tcctggcccc    480 gcagggaccc caggacaaat aggtatgaag gaatcctccc ttttaccttt cacagtcctg    540
agacattcca cgctttcctt tgtcagtgta gacgttccc agtagagtca gatgaggatg     600
ctgttttgcc tcatctgttc tcgcacgtac aagggatgac ccaactgtga ggtttctgag    660
```

```
cccccaccag cctcccctca gcagctgaaa catgcagcct ctcctgtagg actacagtga    720
cagaggcctt gcccggaagt tcagagatgg cttccccgtt ccctgcccat ttcaaagcct    780
tcctgccccc accagcaaca tatacgacac accttcacac acgtgcacgc cccagacgag    840
ccagtaactc ttatctgttt caaaattgcc tcactctgtc cttatgtctt cccccagat    900 tgtgacacag atgtgaaaag ggccgttgga ggtgacagac aggaggccat ccagccaggt    960
actctgggaa gtgcaggtgg ctttaggaca ctagagaact ctcatttggt ctgctggtta    1020
agctcttgca gtatgcgtgg gataagaaat attaataata tgtgcaagcc acgtttgatt    1080
tccatggcac aacatagtgg cctggtgagc actatacatt gcatgaatga caacctggta    1140
gagacggaga gacatttaac caaacccctc ttgtcagaaa tccttttttca ctggaaagca    1200 ccagtgcatt ccaactcagc tccacaggca cgtgtgctgc caggagggtc caggcaga    1258
```

<210> SEQ ID NO 21
<211> LENGTH: 657
<212> TYPE: DNA
<213> ORGANISM: Homo sapiens

<400> SEQUENCE: 21

```
ggtttgcacc caggctactg ccctgcagga gggaatcaat tgtttgccag cacagtgcca    60 gttttttattt gactagactg gcttagtttg cattttatac gaatattttg atttcattac   120
acaatgaaat taaactttta tttacatcag aaccaagatg aattaaatca ttaagttact   180
ctgatcccag aatggtagcc ggtttgcaca gctcgtgctt tgcccttggg gatccccaa    240 ggccgtggga ctcagtgttt aggattgctt gggctcatct tttctccttt ctgtcccag    300 gttgcatagg agggcccaag ggattgccag gcctgccagg accccaggc cccacaggta    360 atgcacggag ggaacctgga gtgcacccag ccttcctccc acatcttcac actgctgtgt    420
ctcccccgcc catctttcct ctggtcctgc atcccccacc ccagacatgg tcgtgtccag    480
catctcagca caaactggtc ttgcgcctac agggagccca ctgtcatttg ccactataga    540
aaaaggagtc tggtagctga cacttagttg gggccaggct agaagagaaa attcagccat    600
ggctgcaggg gaacgccccc aggggcagag atggaagcct cgtgtttagg actggaa      657
```

<210> SEQ ID NO 22
<211> LENGTH: 708
<212> TYPE: DNA
<213> ORGANISM: Homo sapiens

<400> SEQUENCE: 22

```
tagaatggta gggccaaaat ttatagccaa gcatctgacc ccacctccaa agccctcatt    60
tagagcactg tagaatctaa atattggata ttatcattct tatggttcca gtccgtaaac   120
aggattttaa acactgaaaa tcattctgta agcctggagg tgctgtttca ggctgatatt   180 cccccccagcc tcatcatttc ccggtttcat gagatccaca ttaagtcaga tgccaagcat   240
gaccatgccc atttatcctc gtggagcctg atgtggtttg tggtttatttt ggttatttag   300 gtgccaaagg cctccgagga atcccaggct tcgcaggagc tgatggagga ccagggccca   360
ggggcttgcc aggagacgca ggtcgtgaag ggttcccagg accccaggt gagttgagat    420 cagacccca ttcagcccct gggttccagc gggaacctgt gtgtgattca taagcatcca    480
gctctattat cttccacttt gtagaagctg ttttaacaaa tacttgacaa cttttgcatt    540
tgtccttggg agattagaaa ttcttgattt ttcataactg atattgtact gggttttttgc   600 agaagctatc tacagatctt gcaggaaaaa ggagacaggt gtttcggaat ggctgtcctc   660
```

```
cgcaacacct gtctcccagg tatgtcctca gtgttaataa tgattaat         708
```

<210> SEQ ID NO 23
<211> LENGTH: 822
<212> TYPE: DNA
<213> ORGANISM: Homo sapiens

<400> SEQUENCE: 23

```
gggaacccat gaattatgca atcgaggtc caaggaggcg ttgttggctt gtccaccttc    60
actcagtttt agggctgggg ggccgaatgg cggggcaagc agaagaaaca taaccaacag   120
aacgacatgg cgaaggttgt aggttccaaa aagggcgaca gggacaaggg ctcgagctga   180
ggaatgcctt ctgaggaccc catagccaaa tttttgctgt ttccagcctc ttttttgactc  240
ttctcttaga acgtcaccat gctaacttgt ggtttgggc ccacccatgt ttccttttag    300
ggttcatagg accccgagga tccaaaggtg cagtgggcct ccctggccca gatggatccc   360
caggtcccat cggcctgcca gggccagatg ggcccctgg ggaaaggggc ctccctggag    420
aagtcctggg agctcagccc gggccacggg gagatgctgg tgtgcctgga cagcctgggc   480
ttaaaggcct tcccggagac agaggcccc ctggattcag aggtgagtgc ccatcgggg     540
agccgggggc cccatcccag atgcacagtg gcctccaagg gcgaccccaa tccttccgg    600
gggatttggt aggaagcagc ggtgccctat agtgctagcc atgcgtacct tctcccatgg   660
ccttccagca ctcctttaga atgtgtctgt cacaacactg tgactaccca cggtagccag   720
tgcgatctgg ccatctgaga actttgacag gtgtggattc actgatgtaa tctgttgtca   780
agttgcatat gcctggctgt gacaggggcc gtgacaggct ca                      822
```

<210> SEQ ID NO 24
<211> LENGTH: 762
<212> TYPE: DNA
<213> ORGANISM: Homo sapiens

<400> SEQUENCE: 24

```
tcaagtgaag aaaactaggt taaaactata cttatagtgc catgtcaact ctgcaaatgt    60
ctagttattt ataggaatag acaagggcag gaaggaaatt cccagtggta gtcattaccg   120
ctgggtgatg gtgtgcctta cctgattta tcctttatac ttctttgtgt tttcctgatt    180
ctctagagtc cagaaaagca tgaattgctc tttttacaga atgagtgtgt ggagggagat   240
gctgtctgtg atgaacagtc cagagttggc ccccacagct cttgtctctg attcctgcag   300
gaagccaagg gatgcctggg atgccagggc tgaaggggca gccaggcctc ccaggacctt   360
ccggccagcc aggcctgtat gggcctccag gactgcatgg attcccagga gctcctggcc   420
aagaggggcc cttggggctg ccaggaatcc caggccgtga aggtaagacc ccagccctcc   480
cataaacgag tggggtcctc actggtcctg ccaagagaat gagcactgtc ttcttgtgga   540
gctctcaaag tctgttccat ggaaccccctt aagaggtgca ggggttccca aaccagaaca   600
tgtatttcac ctaataagga gacacaaaca gcctgagaca tcggctcatc ctctgtacct   660
gttgtatata ttaaggatct agggaaggtc tcatcgggaa aaagaaaaa gaaagaaatt    720
ccccctacaa aagttcagaa tcactgctct gatgtggaga gg                     762
```

<210> SEQ ID NO 25
<211> LENGTH: 771
<212> TYPE: DNA
<213> ORGANISM: Homo sapiens

<400> SEQUENCE: 25

```
ccccactcac atcagcatcc acacagcttt gtcccttggc ttctgaagac tgcagtggga      60
aagccatgct ggctggcacc ccgccagcac agcctcaacc tccagataca gacctctcca     120
gaaaggccag ccccagggtc ccgctccggc cacactttgg aaactcaccc caacatggtg     180
gttttccact ttccttctaa ggagcttttc ttactgaaca ctcaatgccg taaaagcaga     240
agagaaattt cccctgtgtg tgtttgtcca ccctgtttga tttgctcctc ttcctgacag     300
gtctgcctgg tgatagaggg gaccctgggg acacaggcgc tcctggccct gtgggcatga     360
aaggtctctc tggtgacaga ggagatgctg gcttcacagg ggagcaaggc catccaggaa     420
gccctggatt taaaggaatt gatggaatgc ctgggacccc cgggctaaaa ggtaattgtg     480
tgactgtgac cagggatccc ttggcgggga ggttgggtct aatcaactct gacctgagac     540
agctctgctg ggcgcctctg tgggccgtgg ggctggcctc acacttctgc agattggagg     600
ccttgggact ctcctgacct aggagacagc agcctcagga cagctggtta atgctgctta     660
gacgcgggtg ggaccaatgt gcctcacaaa gccagtttat gaatttacca agacaaactg     720
ctcctgcctg ggaaacatcg tcttattgta aatatcacca tctgcacagg g              771
```

<210> SEQ ID NO 26
<211> LENGTH: 744
<212> TYPE: DNA
<213> ORGANISM: Homo sapiens

<400> SEQUENCE: 26

```
tgggccagtg aacctgcatc atcttcagat ttccctccta gccttcctgc ctgatctttg      60
tgtgtttcct tgttgccaat gtccggtctg aagacaggct gattctggaa tgctgtctgt     120
taacagcaga ggtcaacaga gagaagttgc ttagaagatg gtgtccccgg aaatccctat     180
tttaggttca gaatcttctc acttgagtta cattgccgaa atgttacgga gacgtgagac     240
tgaaatgtcc catgcatttt attcatgtct aacccagcac ttttctcttt tcctctgaag     300
gagatagagg ctcacctggg atggatggtt tccaaggcat gcctggactc aaagggagac     360
ccgggtttcc agggagcaaa ggcgaggctg gattttttcgg aatacccggt ctgaagggtc     420
tggctggtga gccaggtttt aaaggtatgt ccctctctta acatcctcct tacctggtca     480
tggtggcatc ctccttaccc tttcttggtg gcataacatt gcccagaatg aatttttgaa     540
aacccatgca tccaggaacc ctaaagctag acaaaacaaa caaaatgagc taacaaaaac     600
tcaaaggctt tatccctgcc tcaacacact gaccatgtga taagggaata atcctaacca     660
aaggaaactc ttgagaacca aaatgatggc atcgctaaga accaaatatg tcatgaaaca     720
tattccacca tgattatacc gtgg                                             744
```

<210> SEQ ID NO 27
<211> LENGTH: 723
<212> TYPE: DNA
<213> ORGANISM: Homo sapiens

<400> SEQUENCE: 27

```
tcctatggga gtcacactgg ctttgaccgc tccctctgca tctgctggca ggcacgtccc      60
cctactgtgg tgctgtgtgc tcagtgacac cagccccagg cccaggaccc tggagccacc     120
cccaactcca actactccga tggacacagg agaggcttct ccggcgcccct tggtctctct     180
ccaaggcttc cctgcttggg ggagacgtgc agccctatgg ctcagggacc aggccttcac     240
ctgtgttctc ctgcgtggtc tggagccccc agaaaatgac agcactctat tcccttccag     300
```

```
gcagccgagg ggaccctggg cccccaggac cacctcctgt catcctgcca ggaatgaaag      360
acattaaagg agagaaagga gatgaagggc tatggggct gaaaggatac ctgggcgcaa      420
aaggtgaggc ttctgacctg cagccagggg cccctagtcc ctgccgcccc agcccgcacc      480
agctcgtgcc cttctccgtc cccagagacg cccgtgccct ccacctggct tcttcgtgc      540 ttttcatctc tgggcgccct gtgtgtccat agctggcgca gggttgttct ctgatgcctg      600
agtaacctcg gtttcccatc ttaagatttg cagcactggc cgggcgcggt ggctcacgcc      660
tgtaatccca gcactttggg aggccgaggc gggtggatca aaggtgagg agatcaagac      720 cat                                                                    723

<210> SEQ ID NO 28
<211> LENGTH: 782
<212> TYPE: DNA
<213> ORGANISM: Homo sapiens

<400> SEQUENCE: 28
ctactaaaaa tacaaaaaaa ttagccggca tggtggtggg cgcctgtagt cccaactact      60
taggaggctg aggcaggaga atggcgtgaa ccggggaggc agagcttgta gtgagccgag      120
attgcgccac tgcactccag cctgggcgac agagcgagac tccgtctcaa aaaaaaaaa      180 aaaaaaaaa aagattcaca gcacgtagga cagcaaaatg catccaggct gcaaaattga      240
aaactggagg gcgggtgctg cgtcctcacc agagtgttac acaccagggt cttcctgcag      300
gtatccaagg aatgccaggc atcccagggc tgtcaggaat ccctgggctg cctgggaggc      360
ccggccacat caaaggagtc aagggagaca tcggagtccc cggcatcccc ggtttgccag      420
gattccctgg ggtggctggc cccctggaa ttacgggatt cccaggattc ataggaagcc      480
gggtgagtgg gcgtctttta ctccccttgt tctgtgagct cctctcccct ttgcttgtga      540
atggacatgc tttggtctgg aatttgctag ggtgagagtg tcagtggcag ttcagggca      600 gcctcaggct tggtggggtc cacacagccc tggaaggagc tgctgcactt ggacaccatg      660
cagatgtgat gtgagtccaa ccggctgccg tggcccttct gtgggcttgt gctgggtgaa      720
gcatgttgtc tgcattttt atggtggcct tgagagaaca aaacttgaat tttcagggat      780
ca                                                                     782

<210> SEQ ID NO 29
<211> LENGTH: 941
<212> TYPE: DNA
<213> ORGANISM: Homo sapiens

<400> SEQUENCE: 29
aggatgactt gagcccagga aatcaaggca acattgagct atgattgtgc ttctgcactc      60
cagccagggt gacagactgc gatcctgtct caaagaaata aataaataaa taacaaaaa      120 gaacagctaa gcaaaccgcc tatgatacac actaaaaaac acgagttttc cacaaaatga      180
caagatcaca aaccttgagt attgtcgtta gcatactgga tagttaaata agtgagctaa      240
cttcagagtt acaactgact tcgctaacag ccttctaaga tggttcatgt ctgtctttag      300
ggtgacaaag gtgccccagg gagagcaggc ctgtatggcg agattggcgc gactggtgat      360
ttcggtgagt gttgcccgtc cagtgaaaac agggagtcca caattcagag ctctctgagc      420
atgtgagcca atttcagacc tgcaagtgct gttaggtatt ttaaaacaaa ttattccttgt      480 taggaatata acaaaataga agttgcaaaa ctcacaaagt cccagtggaa agtcctgttc      540
```

| | | | | |
|---|---|---|---|---|
| ttagccgtct | tttttgcatg | taacaggtga | catcgggac | actataaatt | taccaggaag | 600 |
| accaggcctg | aagggggagc | ggggcaccac | tggaatacca | ggtacgcaag | ttatttttcct | 660 |
| tgtcttcatc | ttcaacaaca | gccctgagcc | tttgtctagg | agcccgactt | gccaaacaga | 720 |
| tcaaattcag | taacaaccag | aaagcacttg | atagtgaatg | aggtcttcaa | gtccaatgtg | 780 |
| caagaaagac | cgtcgttttt | aattaagtta | aatctgaaga | taaaatcagg | aagtctttct | 840 |
| ctctctctgt | ctctctcttt | gatactgaaa | aaagccagaa | tggaccctcg | gtggatgaga | 900 |
| atcactgcag | tccataaagt | gtaactgatg | aaaagccagc | t | 941 |

<210> SEQ ID NO 30
<211> LENGTH: 708
<212> TYPE: DNA
<213> ORGANISM: Homo sapiens

<400> SEQUENCE: 30

| | | | | | | |
|---|---|---|---|---|---|---|
| agctgtggtc | ccacaatgga | agggtggggc | cagctgtacc | catcatccct | gggggtgtcc | 60 |
| tgttttccct | aagacagtga | ggggtgcatg | ggtacatggg | tgctgccttg | gaagctggct | 120 |
| agtgcaggct | cagagggagg | aagtaggtta | aaaatcagct | aaggaaggag | cacggttgga | 180 |
| tgcctctctc | cattcctgaa | ggagcagcag | tgtggttctg | cacatcctag | agccggggtt | 240 |
| ccagggaacc | cacaggggcg | cggtgtctgt | ttgttccaag | cagcatgtct | gtggttgcag | 300 |
| gtctgaaggg | attctttgga | gagaagggaa | cagaaggtga | catcggcttc | cctgggataa | 360 |
| caggcgtgac | tggagtccaa | ggccctcctg | gacttaaagg | acaaacaggt | aaaatctccc | 420 |
| gcagccacac | agccttcctc | aggcaggccc | tccggagacc | ccagaacaaa | ggcggtcaac | 480 |
| attgtcaatt | cctccaatc | acacccaacc | ctggaagctc | actcgtgcct | gctgccagct | 540 |
| taggagcttt | cctcagtgct | gatggcatgg | agagaaacaa | ccacctgggc | tggggggaga | 600 |
| cctgagaatt | ggagagaagc | atggggtga | atgagaagtg | cctcttcggt | tgagcctctg | 660 |
| tctctcatat | agaagccgac | ggtttgtaag | ggatcccttt | gcttgcat | | 708 |

<210> SEQ ID NO 31
<211> LENGTH: 708
<212> TYPE: DNA
<213> ORGANISM: Homo sapiens

<400> SEQUENCE: 31

| | | | | | | |
|---|---|---|---|---|---|---|
| ctctccaggc | actgcctcag | ggtcctctcc | agacgtctat | ttggataata | gggcgacaat | 60 |
| taaaactaca | cgctattttc | tctctggcaa | ggctgagcaa | atcctattga | atttgtatgt | 120 |
| ggggtctaag | accacctgca | tccccagctt | gagggacagt | tctaatctct | cctccaactg | 180 |
| gcactgcggc | ccttccggcc | ctcggcccct | cccagagcgg | ctgcccctcc | tgccaggacc | 240 |
| tcaccacaca | gcgcccaagg | tgtcctgtgt | gctcagactt | aatgctgtgt | tcaccccag | 300 |
| gctttccagg | gctgactggg | cctccagggt | cgcagggaga | gctggggcgg | attggactgc | 360 |
| ctggtggcaa | aggagatgat | ggctggccgg | gagctccggg | cttaccaggt | aaggtcacgt | 420 |
| aaaacacgtg | gtcacccaga | cccagagtcg | tgggctgtgc | aggaggcacc | gctgagcagg | 480 |
| ccagcctctc | tcagggcgac | ttctaaggcc | catacgagag | caaaggcagg | tctgctgtgg | 540 |
| cttacggtgg | tctgcaccaa | catagcagca | cagggtatac | tggcgcccca | ggcaactggg | 600 |
| aatcaagcca | gatgcacaaa | tctgcccagg | gcttcacctc | ccagaaggat | gaatgaaagc | 660 |
| ctcccagaga | ggcttcaggg | tccacttgtc | atcgccacac | agggacgc | | 708 |

<210> SEQ ID NO 32
<211> LENGTH: 672
<212> TYPE: DNA
<213> ORGANISM: Homo sapiens

<400> SEQUENCE: 32

```
ttagcaggat tgtatgggtg acagtatcag gtgacagttt cagagccaac aaaacacatc      60
tgagttatct tgagggtttc tcccacccag aaccccctgt gctgtcccac acatgaaata     120
acaatgagtg acaccccac aggtgaaata acgatgagtg acaccccat gggtgaaata       180
acgatgagtg acaccccat gggtgaaata acgatgagtg acaccccgc aggtgaaata       240
aataacgatg agtgacaccc cgcaggtga aataaataac gatgagtgac accccgcag       300
gttttccggg actccgtggg atccgcggct tacacggctt gccaggcacc aagggctttc     360
caggatcccc aggtactctg tgccgtccca gccccgagtc ccacgcagag gtgtcgaggg     420
tggggactct gtgctgagtc tgccctccag acttcaggga atggagggtc tcagagagca    480
gggtgggctt cctgaagtgc tatgcgatcg gccgtgaggg gcgggtccgg gccctgtggt     540
cctgtacgct gctaagatgt gatccctaag aatcggtttc tcaaggcagt tgctgggttg    600
aatggactca tcaggctttt agacggagag agaaatagag tccttgcttt ttcagcagca    660
ccgttgggag gg                                                         672
```

<210> SEQ ID NO 33
<211> LENGTH: 726
<212> TYPE: DNA
<213> ORGANISM: Homo sapiens

<400> SEQUENCE: 33

```
gcctagaggc ccgggagggg tcccagctcc ttgacccact gtttctgtga atttgaaccc     60
tctgatgggc ctcgatcctc ttatccatag agccaagggc ttccactgtg atctctgtaa    120
gatcccttcc aaatctcagc tcctgtgacc tggaggccat atattgcaat gcaagctgaa    180
atcaccatgg ctgcctctgt ttctttgctt ttgaggcacc ccaagctgtt ctttcactta    240
ggaaagtcaa ctgtatggtt ggaaacaccg acatcagctg ctgttataac tcttccacag    300
gttctgacat ccacggagac ccaggcttcc caggccctcc tggggaaaga ggtgacccag    360
gagaggccaa caccttcca ggccctgtgg gagtcccagg acagaaagga gaccaaggag      420
ctccaggtga ggccacacat tccaagccaa cattgccgtc ccagtaacca gaacccaccc    480
agaggtgggg ccatggagtg tctatggggt gggagaggct gtgcagaagt gcaggaaaga    540
gctggttttt ctggggagga ctacctgttg caggacctct cagctagtct tagtttgtta    600
ggcaatttat tttatcccat cagtgttagt gaggcactga ccacccatcc cgtggagtaa    660
ctgataagct ccctggccta gagacccat cagatcctct gtgcgcctgg ggcactggca     720
caggcc                                                                726
```

<210> SEQ ID NO 34
<211> LENGTH: 717
<212> TYPE: DNA
<213> ORGANISM: Homo sapiens

<400> SEQUENCE: 34

```
agcatgatcg ggcagcgcct tggggaagtc gagcacaggc agacaggatc ccagtggagg      60
gctcctcaca ggagaaaggc tggggtgggg gaggggttca catagcccct gccccccaa     120
ccccgccctg agggcctccc cagccccacc atgagatgtt ccttggcctg agggcacctc    180
```

```
ccatcactgt ctcgctcgct aggctctggt ccaccacagg tgatggtgtg gagggaaaat    240
agtagatttg aaaagttggg tgctaacgct gaaaataatt tcttctgttt tcatcctaag    300
gggaacgagg cccacctggg agcccaggac ttcagggggtt ccctggtatc acacccccctt   360 ccaacatctc tggggcacct ggtgacaaag gggcgccagg gatatttggc ctgaaaggta    420
agcaggactt atacatctgt gcttcgacat ctctaggggc aggagctggc aatggcccgc    480
ttaatgtagg gggagaacag acgttcattt ccacgctgtg cccagactcc ggtcaaagag    540
gcaggagcca tgatggctcc tcctgtgtca tttccatcac ctgcacgacc tggtccctgg    600
gaagctgaga cacaggccat gtcatttact tgctgtaata gcagatattc aaactgcagg    660
gggctcagaa atgtgcagta tgaacggctt tcttcttcct cactgtattg tgtttag      717

<210> SEQ ID NO 35
<211> LENGTH: 1744
<212> TYPE: DNA
<213> ORGANISM: Homo sapiens

<400> SEQUENCE: 35
acacggggag tgcgtgtata acggggacag atttcagttt aggatgagaa agttctggag    60
ctggtcggcg gtgaaggtga atatattgaa tgccactgag cagtgcacct aaaaatgatt    120
aaaatggtaa cttttatgtt ctacgtattt tacgacaatt ttttaaaaac atagacaaag    180
tcattccatg ccacagactt gccagagact gtcgcctgaa tgggtgacgg tgcacctgac    240
tgcccccagg ggccttgggg ccctgtttaa accctccttt cttgtcccta atgccaacag    300
gttatcgggg cccaccaggg ccaccaggtt ctgctgctct tcctggaagc aaaggtgaca    360
cagggaaccc aggagctcca ggaaccccag ggaccaaagg atgggccggg gactccgggc    420
cccagggcag gcctggtgtg tttggtctcc caggagaaaa aggtaacagt gcccatggcc    480
atgggccagc agccctggcc acagtgagag gagcccccctc ccacagact ttcgtgtccc    540 taacgtcttg tttgtgttgc agggcccagg ggtgaacaag gcttcatggg gaacactgga    600
cccactgggg cggtgggcga cagaggcccc aagggaccca agggagaccc aggattccct    660
ggtaagtgac cgtctggtat cttcagagct agtggctcag cccagcctct ccaggcttgg    720
ggacatcctg gaggtcaaac ggccaggatc ctctctggca tgggtcacat gttgtaaaga    780
gcagggagga aaccaaggct gtgcctcgga tgttgtcaca ggaccttggg gaatggagag    840
cttaatattc aaacggcagg cgctgagtca cggctcaggc ccgttagtgt ctggctcatc    900
tctagaaagc acagttgtct gggaagctcc aaaagaagcc tccctggtga aaacgcagt    960 agcactcgga gcaagagagt ggaacgacct tgtgtgttta ctggggcctc tctgtttccc   1020
ttccaggtgc ccccgggact gtgggagccc cggggattgc aggaatcccc cagaagattg   1080
ccgtccaacc agggacagtg ggtccccagg ggaggcgagg cccccctggg gcaccgggg   1140 agatggggcc ccagggcccc cccggagaac caggtagagt gctgagctgg ggcctggagc   1200
ccctcggggc tgcccgggca aggccagggc ctgctggcat tgcgtcctct tgtgttctct   1260
ttgtggatcg ccggccgtgc caggcgtggt cagtttccag ccataacgct tctttggtgg   1320
cttgcaggtt tccgtggggc tccagggaaa gctgggcccc aaggaagagg tggtgtgtct   1380
gctgttcccg gcttccgggg agatgaagga cccataggcc accaggggcc gattggccaa   1440
gaaggtgagt gacagtgggg aaggaccttc ccaggtccta gtgctctgga tctgactcac   1500
agactgtggt ctgcaggaag gggacacacg agagcccaga aaagccagaa atgaggcgct   1560
gccccaccct cctgctccta atctgggcgt agcagctaca ctcctatgcc cagcagaaca   1620
```

```
cctggccccg agtcctggga cagcctccct ccttttcctg ggacacctgc ggtgctgtgg    1680
agtgggcggc agggatcagt agacttcaag ggtcaggatt agacaaggag ccaaaagaaa    1740
ccga                                                                 1744

<210> SEQ ID NO 36
<211> LENGTH: 792
<212> TYPE: DNA
<213> ORGANISM: Homo sapiens

<400> SEQUENCE: 36
cggctgtcaa gggggctgct ctctctctct ttctcaggct gcaggtgcac taggccgtcc      60
actctctctc tctctcaggc tgcaggtgca ccaggccgtc cactcactct ctctctcggg     120
ctgcaggtac accaggccgt ccactctctc tctctctctc tctctcgggc tgcaggtgca     180
ccaggccgtc cactctctct ctctctctca ggctgtaggt gcaccaggcc gtccactctc     240
tctctttctc gggctgcagg tgcaccaggc cgtccactct ctctctttct cgggctgcag     300
gtgcaccagg ccgtccaggg agcccgggcc tgccgggtat gccaggccgc agcgtcagca     360
tcggctacct cctggtgaag cacagccaga cggaccagga gcccatgtgc ccagtgggca     420
tgaacaaact ctggagtgga tacagcctgc tgtacttcga gggccaggag aaggcgcaca     480
accaggacct gggtaggtac ctcccacccg gcccccgttg cctgctcagg ctggccccgg     540
aagtggccaa gatcaaaggg ccacagcgag actcccaaac cctccacggc tggtaagttc     600
ccctgacgga agggtccatc tacattcctc gagtgcagaa agattaaaac ggcctttgaa     660
gcagaagcct tacaaagccc ttaaacctca ggaccttaac acagggacct gccttttaac     720
ctggtattga cttccgcagg ctcccatgtg accgtctgac ccccgaccc ctctccagtg     780 gagaccacca at                                                        792

<210> SEQ ID NO 37
<211> LENGTH: 887
<212> TYPE: DNA
<213> ORGANISM: Homo sapiens

<400> SEQUENCE: 37
ggtaaggctc acccaaaatg ctattccatg aagacgccac tccctggtga tccaacttgg      60
cccagtatgt gtgagaactt gtagaagaac agagctgttc caaaatgcca gtggagtctg     120
atcaaaaaga gaaaagaaa gaaattggga agccttagcc tggccctcca gtaggtggct     180
aaactccacc aggtgccctg gggcgagtcc gtgacacaca gctcctggg cctggctggg     240 gctggcaggt gcgtcttcta gccacactgc actgtgatct catgaccct ccttccacag     300 ggctggcggg ctcctgcctg gcgcggttca gcaccatgcc cttcctgtac tgcaaccctg     360
gtgatgtctg ctactatgcc agccggaacg acaagtccta ctggctctct accactgcgc     420
cgctgcccat gatgccgtg gccgaggacg agatcaagcc ctacatcagc cgctgttctg     480
tgtgtgaggc cccggccatc gccatcgcgg tccacagtca ggatgtctcc atcccacact     540
gcccagctgg gtggcggagt ttgtggatcg gatattcctt cctcatggta tgtggtattt     600
gcccagttcc cctccccaac cacaccctgc tgggacaca gcaagaacag ctgcctttgt     660
gagaagaatc agacacggca gtccagggtg tgcactgcac aagggtagtt ggcccaggaa     720
gcgagcgaga gctggaacac agcttacact tggctaactg agccacatgc tgggcacagg     780
gcttcctcca cccagaaagg gctcattaat ttgccaccag gcctttgtaa ggagtgtaac     840
```

```
caggacgaac ttgcctgtta tccgtcttac taggtacaac accaaca              887
```

```
<210> SEQ ID NO 38
<211> LENGTH: 1263
<212> TYPE: DNA
<213> ORGANISM: Homo sapiens

<400> SEQUENCE: 38
gctatgccct gacccgtgc cacctgcagg ctgtgattcc taaccctgtc ctgcccccct    60
ctctgtgcag cacacggcgg cgggagacga aggcggtggc caatcactgg tgtcaccggg   120
cagctgtcta gaggacttcc gcgccacacc attcatcgaa tgcaatggag ccgcggcac    180 ctgccactac tacgccaaca agtacagctt ctggctgacc accattcccg agcagagctt   240
ccagggctcg ccctccgccg acacgctcaa ggccggcctc atccgcacac acatcagccg   300
ctgccaggtg tgcatgaaga acctgtgagc cggcgcgtgc caggaagggc cattttggtg   360
cttattctta acttattacc tcaggtgcca acccaaaaat tggttttatt ttttcttaa    420 aaaaaaaaaa gtctaccaaa ggaatttgca tccagcagca gcacttagac ctgccagcca   480
ctgtcaccga gcgggtgcaa gcactcgggg tccctggagg gcaagccctg cccacagaaa   540
gccaggagca gccctggccc ccatcagccc tgctagacgc accgcctgaa ggcacagcta   600
accacttcgc acacacccat gtaaccactg cactttccaa tgccacagac aactcacatt   660
gttcaactcc cttctcgggg tgggacagac gagacaacag cacacaggca gccagccgtg   720
gccagaggct cgaggggctc agggcctcag gcacccgtcc ccacacgagg gccccgtggg   780
tgggcctggc cctgctttct acgccaatgt tatgccagct ccatgttctc ccaaataccg   840
ttgatgtgaa ttatttaaa ggcaaaaccg tgctctttat tttaaaaaac actgataatc    900
acactgcggt aggtcattct tttgccacat ccctatagac cactgggttt ggcaaaactc   960
aggcagaagt ggagaccttt ctagacatca ttgtcagcct tgctacttga aggtacaccc  1020
catagggtcg gaggtgctgt ccccactgcc ccacgttgtc cctgagattt aacccctcca  1080
ctgctggggg tgagctgtac tcttctgact gccccctcct gtgtaacgac tacaaaataa  1140
aacttggttc tgaatatttt taaaccccga gttgttgacc gccttaatct cgtgtccata  1200
gagcaaaacg tctgctcaga tggatgcgag gcacagcgtc cgcccacgct gctgttttta  1260
atc                                                              1263

<210> SEQ ID NO 39
<211> LENGTH: 21
<212> TYPE: DNA
<213> ORGANISM: Artificial Sequence
<220> FEATURE:
<223> OTHER INFORMATION: primer ex2-F

<400> SEQUENCE: 39
atgggctgcc tccctcatcc t                                            21

<210> SEQ ID NO 40
<211> LENGTH: 25
<212> TYPE: DNA
<213> ORGANISM: Artificial Sequence
<220> FEATURE:
<223> OTHER INFORMATION: primer ex2-R

<400> SEQUENCE: 40
gagagttaca ccgaagggtc catgc                                        25
```

-continued

```
<210> SEQ ID NO 41
<211> LENGTH: 25
<212> TYPE: DNA
<213> ORGANISM: Artificial Sequence
<220> FEATURE:
<223> OTHER INFORMATION: primer ex3-F

<400> SEQUENCE: 41
gcatggaccc ttcggtgtaa ctctc                                              25

<210> SEQ ID NO 42
<211> LENGTH: 25
<212> TYPE: DNA
<213> ORGANISM: Artificial Sequence
<220> FEATURE:
<223> OTHER INFORMATION: primer ex3-R

<400> SEQUENCE: 42
ccactcaaac gtcccaacca ctctc                                              25

<210> SEQ ID NO 43
<211> LENGTH: 22
<212> TYPE: DNA
<213> ORGANISM: Artificial Sequence
<220> FEATURE:
<223> OTHER INFORMATION: primer ex4-F

<400> SEQUENCE: 43
ttggaaggat tctcaacaga tg                                                 22

<210> SEQ ID NO 44
<211> LENGTH: 20
<212> TYPE: DNA
<213> ORGANISM: Artificial Sequence
<220> FEATURE:
<223> OTHER INFORMATION: primer ex4-R

<400> SEQUENCE: 44
agcgaggcat gactgtatga                                                    20

<210> SEQ ID NO 45
<211> LENGTH: 20
<212> TYPE: DNA
<213> ORGANISM: Artificial Sequence
<220> FEATURE:
<223> OTHER INFORMATION: primer ex5&6-F

<400> SEQUENCE: 45
tcgtggaaat tgaacctttg                                                    20

<210> SEQ ID NO 46
<211> LENGTH: 20
<212> TYPE: DNA
<213> ORGANISM: Artificial Sequence
<220> FEATURE:
<223> OTHER INFORMATION: primer ex5&6-R

<400> SEQUENCE: 46
cctaggatgc acgcaatgtt                                                    20

<210> SEQ ID NO 47
<211> LENGTH: 25
<212> TYPE: DNA
<213> ORGANISM: Artificial Sequence
<220> FEATURE:
<223> OTHER INFORMATION: primer ex7-F
```

<400> SEQUENCE: 47
gccgggaaca tggcttatga gaata                                   25

<210> SEQ ID NO 48
<211> LENGTH: 25
<212> TYPE: DNA
<213> ORGANISM: Artificial Sequence
<220> FEATURE:
<223> OTHER INFORMATION: primer ex7-R

<400> SEQUENCE: 48
gttatgcttc cgttctggcc acagt                                   25

<210> SEQ ID NO 49
<211> LENGTH: 20
<212> TYPE: DNA
<213> ORGANISM: Artificial Sequence
<220> FEATURE:
<223> OTHER INFORMATION: primer ex8-F

<400> SEQUENCE: 49
ctgcaccgaa tgttaatgga                                         20

<210> SEQ ID NO 50
<211> LENGTH: 20
<212> TYPE: DNA
<213> ORGANISM: Artificial Sequence
<220> FEATURE:
<223> OTHER INFORMATION: primer ex8-R

<400> SEQUENCE: 50
gattatgccg ccattctagg                                         20

<210> SEQ ID NO 51
<211> LENGTH: 21
<212> TYPE: DNA
<213> ORGANISM: Artificial Sequence
<220> FEATURE:
<223> OTHER INFORMATION: primer ex9&10-F

<400> SEQUENCE: 51
gggctgatct gtttgatatg c                                       21

<210> SEQ ID NO 52
<211> LENGTH: 19
<212> TYPE: DNA
<213> ORGANISM: Artificial Sequence
<220> FEATURE:
<223> OTHER INFORMATION: primer ex9&10-R

<400> SEQUENCE: 52
ccagagtggg cacctgtgt                                          19

<210> SEQ ID NO 53
<211> LENGTH: 20
<212> TYPE: DNA
<213> ORGANISM: Artificial Sequence
<220> FEATURE:
<223> OTHER INFORMATION: primer ex11-F

<400> SEQUENCE: 53
cagaaacctc catgcatcct                                         20

<210> SEQ ID NO 54
<211> LENGTH: 21

```
<212> TYPE: DNA
<213> ORGANISM: Artificial Sequence
<220> FEATURE:
<223> OTHER INFORMATION: primer ex11-R

<400> SEQUENCE: 54
caaacaaacc cacaaacacc t                                          21

<210> SEQ ID NO 55
<211> LENGTH: 20
<212> TYPE: DNA
<213> ORGANISM: Artificial Sequence
<220> FEATURE:
<223> OTHER INFORMATION: primer ex12-F

<400> SEQUENCE: 55
ttgccgataa ataggccttg                                            20

<210> SEQ ID NO 56
<211> LENGTH: 20
<212> TYPE: DNA
<213> ORGANISM: Artificial Sequence
<220> FEATURE:
<223> OTHER INFORMATION: primer ex12-R

<400> SEQUENCE: 56
tttcctggct gagaaatgct                                            20

<210> SEQ ID NO 57
<211> LENGTH: 26
<212> TYPE: DNA
<213> ORGANISM: Artificial Sequence
<220> FEATURE:
<223> OTHER INFORMATION: primer ex13-F

<400> SEQUENCE: 57
tttcctttcg atttaaagac aactgc                                     26

<210> SEQ ID NO 58
<211> LENGTH: 27
<212> TYPE: DNA
<213> ORGANISM: Artificial Sequence
<220> FEATURE:
<223> OTHER INFORMATION: primer ex13-R

<400> SEQUENCE: 58
tggaatgtgg ttgaatacaa ttgaaga                                    27

<210> SEQ ID NO 59
<211> LENGTH: 21
<212> TYPE: DNA
<213> ORGANISM: Artificial Sequence
<220> FEATURE:
<223> OTHER INFORMATION: primer ex14-F

<400> SEQUENCE: 59
catgtcatga accctgattg a                                          21

<210> SEQ ID NO 60
<211> LENGTH: 19
<212> TYPE: DNA
<213> ORGANISM: Artificial Sequence
<220> FEATURE:
<223> OTHER INFORMATION: primer ex14-R

<400> SEQUENCE: 60
```
atgagagact ggcggtgtg        19

<210> SEQ ID NO 61
<211> LENGTH: 20
<212> TYPE: DNA
<213> ORGANISM: Artificial Sequence
<220> FEATURE:
<223> OTHER INFORMATION: primer ex15-F

<400> SEQUENCE: 61
agtcctggag cagaggatga        20

<210> SEQ ID NO 62
<211> LENGTH: 20
<212> TYPE: DNA
<213> ORGANISM: Artificial Sequence
<220> FEATURE:
<223> OTHER INFORMATION: primer ex15-R

<400> SEQUENCE: 62
aaaccaaacc aaaccgacaa        20

<210> SEQ ID NO 63
<211> LENGTH: 20
<212> TYPE: DNA
<213> ORGANISM: Artificial Sequence
<220> FEATURE:
<223> OTHER INFORMATION: primer ex16-F

<400> SEQUENCE: 63
cgtagtcaag ccctctggaa        20

<210> SEQ ID NO 64
<211> LENGTH: 20
<212> TYPE: DNA
<213> ORGANISM: Artificial Sequence
<220> FEATURE:
<223> OTHER INFORMATION: primer ex16-R

<400> SEQUENCE: 64
tgagatgcca aggcctattt        20

<210> SEQ ID NO 65
<211> LENGTH: 27
<212> TYPE: DNA
<213> ORGANISM: Artificial Sequence
<220> FEATURE:
<223> OTHER INFORMATION: primer ex17-F

<400> SEQUENCE: 65
tttggagtta tacatcagag acaaaaa        27

<210> SEQ ID NO 66
<211> LENGTH: 20
<212> TYPE: DNA
<213> ORGANISM: Artificial Sequence
<220> FEATURE:
<223> OTHER INFORMATION: primer ex17-R

<400> SEQUENCE: 66
gtgggcgaga caccataagt        20

<210> SEQ ID NO 67
<211> LENGTH: 20
<212> TYPE: DNA
<213> ORGANISM: Artificial Sequence

```
<220> FEATURE:
<223> OTHER INFORMATION: primer ex18-F

<400> SEQUENCE: 67
ctcgggtttc ttctttggaa                                              20

<210> SEQ ID NO 68
<211> LENGTH: 21
<212> TYPE: DNA
<213> ORGANISM: Artificial Sequence
<220> FEATURE:
<223> OTHER INFORMATION: primer ex18-R

<400> SEQUENCE: 68
gctctgtgtc cctaacagga g                                            21

<210> SEQ ID NO 69
<211> LENGTH: 19
<212> TYPE: DNA
<213> ORGANISM: Artificial Sequence
<220> FEATURE:
<223> OTHER INFORMATION: primer ex19-F

<400> SEQUENCE: 69
ctcatcaggc cgcatacag                                               19

<210> SEQ ID NO 70
<211> LENGTH: 20
<212> TYPE: DNA
<213> ORGANISM: Artificial Sequence
<220> FEATURE:
<223> OTHER INFORMATION: primer ex19-R

<400> SEQUENCE: 70
gacctgagtg caggtgcttt                                              20

<210> SEQ ID NO 71
<211> LENGTH: 20
<212> TYPE: DNA
<213> ORGANISM: Artificial Sequence
<220> FEATURE:
<223> OTHER INFORMATION: primer ex20-F

<400> SEQUENCE: 71
tctggacacg aacacaaagg                                              20

<210> SEQ ID NO 72
<211> LENGTH: 20
<212> TYPE: DNA
<213> ORGANISM: Artificial Sequence
<220> FEATURE:
<223> OTHER INFORMATION: primer ex20-R

<400> SEQUENCE: 72
cgggcttcat ctgaacatta                                              20

<210> SEQ ID NO 73
<211> LENGTH: 20
<212> TYPE: DNA
<213> ORGANISM: Artificial Sequence
<220> FEATURE:
<223> OTHER INFORMATION: primer ex21-F

<400> SEQUENCE: 73
cctgcatctg tggttgtctc                                              20
```

<210> SEQ ID NO 74
<211> LENGTH: 20
<212> TYPE: DNA
<213> ORGANISM: Artificial Sequence
<220> FEATURE:
<223> OTHER INFORMATION: primer ex21-R

<400> SEQUENCE: 74
ggggatggat ttcaccttct                                           20

<210> SEQ ID NO 75
<211> LENGTH: 20
<212> TYPE: DNA
<213> ORGANISM: Artificial Sequence
<220> FEATURE:
<223> OTHER INFORMATION: primer ex22-F

<400> SEQUENCE: 75
gctaagagga atgcggaaca                                           20

<210> SEQ ID NO 76
<211> LENGTH: 20
<212> TYPE: DNA
<213> ORGANISM: Artificial Sequence
<220> FEATURE:
<223> OTHER INFORMATION: primer ex22-R

<400> SEQUENCE: 76
ggaggcctca gagtgtcttg                                           20

<210> SEQ ID NO 77
<211> LENGTH: 20
<212> TYPE: DNA
<213> ORGANISM: Artificial Sequence
<220> FEATURE:
<223> OTHER INFORMATION: primer ex23-F

<400> SEQUENCE: 77
gccagctgtg tgagatgaaa                                           20

<210> SEQ ID NO 78
<211> LENGTH: 20
<212> TYPE: DNA
<213> ORGANISM: Artificial Sequence
<220> FEATURE:
<223> OTHER INFORMATION: primer ex23-R

<400> SEQUENCE: 78
gtccccgctc acctagaaag                                           20

<210> SEQ ID NO 79
<211> LENGTH: 26
<212> TYPE: DNA
<213> ORGANISM: Artificial Sequence
<220> FEATURE:
<223> OTHER INFORMATION: primer ex24-F

<400> SEQUENCE: 79
tccagaacaa tcacaaccaa aggtga                                    26

<210> SEQ ID NO 80
<211> LENGTH: 25
<212> TYPE: DNA
<213> ORGANISM: Artificial Sequence
<220> FEATURE:
<223> OTHER INFORMATION: primer ex24-R

```
<400> SEQUENCE: 80
gggtgtttgg agaacctgaa ggatg                                          25

<210> SEQ ID NO 81
<211> LENGTH: 20
<212> TYPE: DNA
<213> ORGANISM: Artificial Sequence
<220> FEATURE:
<223> OTHER INFORMATION: primer ex25-F

<400> SEQUENCE: 81
ggaagtcgag gcgatcttta                                                20

<210> SEQ ID NO 82
<211> LENGTH: 20
<212> TYPE: DNA
<213> ORGANISM: Artificial Sequence
<220> FEATURE:
<223> OTHER INFORMATION: primer ex25-R

<400> SEQUENCE: 82
caaaggaaag cgtggaatgt                                                20

<210> SEQ ID NO 83
<211> LENGTH: 20
<212> TYPE: DNA
<213> ORGANISM: Artificial Sequence
<220> FEATURE:
<223> OTHER INFORMATION: primer ex26-F

<400> SEQUENCE: 83
cccagacgag ccagtaactc                                                20

<210> SEQ ID NO 84
<211> LENGTH: 20
<212> TYPE: DNA
<213> ORGANISM: Artificial Sequence
<220> FEATURE:
<223> OTHER INFORMATION: primer ex26-R

<400> SEQUENCE: 84
ttatcccacg catactgcaa                                                20

<210> SEQ ID NO 85
<211> LENGTH: 20
<212> TYPE: DNA
<213> ORGANISM: Artificial Sequence
<220> FEATURE:
<223> OTHER INFORMATION: primer ex27-F

<400> SEQUENCE: 85
taggattgct tgggctcatc                                                20

<210> SEQ ID NO 86
<211> LENGTH: 20
<212> TYPE: DNA
<213> ORGANISM: Artificial Sequence
<220> FEATURE:
<223> OTHER INFORMATION: primer ex27-R

<400> SEQUENCE: 86
tttgtgctga gatgctggac                                                20

<210> SEQ ID NO 87
```

```
<210> SEQ ID NO 87
<211> LENGTH: 20
<212> TYPE: DNA
<213> ORGANISM: Artificial Sequence
<220> FEATURE:
<223> OTHER INFORMATION: primer ex28-F

<400> SEQUENCE: 87
ttatcctcgt ggagcctgat                                               20

<210> SEQ ID NO 88
<211> LENGTH: 20
<212> TYPE: DNA
<213> ORGANISM: Artificial Sequence
<220> FEATURE:
<223> OTHER INFORMATION: primer ex28-R

<400> SEQUENCE: 88
ctcccaagga caaatgcaaa                                               20

<210> SEQ ID NO 89
<211> LENGTH: 21
<212> TYPE: DNA
<213> ORGANISM: Artificial Sequence
<220> FEATURE:
<223> OTHER INFORMATION: primer ex29-F

<400> SEQUENCE: 89
ccatgctaac ttgtggtttg g                                             21

<210> SEQ ID NO 90
<211> LENGTH: 19
<212> TYPE: DNA
<213> ORGANISM: Artificial Sequence
<220> FEATURE:
<223> OTHER INFORMATION: primer ex29-R

<400> SEQUENCE: 90
cactgtgcat ctgggatgg                                                19

<210> SEQ ID NO 91
<211> LENGTH: 20
<212> TYPE: DNA
<213> ORGANISM: Artificial Sequence
<220> FEATURE:
<223> OTHER INFORMATION: primer ex30-F

<400> SEQUENCE: 91
agtgtgtgga gggagatgct                                               20

<210> SEQ ID NO 92
<211> LENGTH: 20
<212> TYPE: DNA
<213> ORGANISM: Artificial Sequence
<220> FEATURE:
<223> OTHER INFORMATION: primer ex30-R

<400> SEQUENCE: 92
gtgaggaccc cactcgttta                                               20

<210> SEQ ID NO 93
<211> LENGTH: 20
<212> TYPE: DNA
<213> ORGANISM: Artificial Sequence
<220> FEATURE:
<223> OTHER INFORMATION: primer ex31-F
```

```
<400> SEQUENCE: 93
tgtttgtcca ccctgtttga                                               20

<210> SEQ ID NO 94
<211> LENGTH: 20
<212> TYPE: DNA
<213> ORGANISM: Artificial Sequence
<220> FEATURE:
<223> OTHER INFORMATION: primer ex31-R

<400> SEQUENCE: 94
ccagcagagc tgtctcaggt                                               20

<210> SEQ ID NO 95
<211> LENGTH: 20
<212> TYPE: DNA
<213> ORGANISM: Artificial Sequence
<220> FEATURE:
<223> OTHER INFORMATION: primer ex32-F

<400> SEQUENCE: 95
cgaaatgtta cggagacgtg                                               20

<210> SEQ ID NO 96
<211> LENGTH: 20
<212> TYPE: DNA
<213> ORGANISM: Artificial Sequence
<220> FEATURE:
<223> OTHER INFORMATION: primer ex32-R

<400> SEQUENCE: 96
tgccaccaag aaagggtaag                                               20

<210> SEQ ID NO 97
<211> LENGTH: 20
<212> TYPE: DNA
<213> ORGANISM: Artificial Sequence
<220> FEATURE:
<223> OTHER INFORMATION: primer ex33-F

<400> SEQUENCE: 97
caggccttca cctgtgttct                                               20

<210> SEQ ID NO 98
<211> LENGTH: 19
<212> TYPE: DNA
<213> ORGANISM: Artificial Sequence
<220> FEATURE:
<223> OTHER INFORMATION: primer ex33-R

<400> SEQUENCE: 98
gtctctgggg acggagaag                                                19

<210> SEQ ID NO 99
<211> LENGTH: 20
<212> TYPE: DNA
<213> ORGANISM: Artificial Sequence
<220> FEATURE:
<223> OTHER INFORMATION: primer ex34-F

<400> SEQUENCE: 99
cagcacgtag gacagcaaaa                                               20
```

```
<210> SEQ ID NO 100
<211> LENGTH: 20
<212> TYPE: DNA
<213> ORGANISM: Artificial Sequence
<220> FEATURE:
<223> OTHER INFORMATION: primer ex34-R

<400> SEQUENCE: 100
gctcacagaa caagggagt                                                    20

<210> SEQ ID NO 101
<211> LENGTH: 20
<212> TYPE: DNA
<213> ORGANISM: Artificial Sequence
<220> FEATURE:
<223> OTHER INFORMATION: primer ex35-F

<400> SEQUENCE: 101
acagctaagc aaaccgccta                                                   20

<210> SEQ ID NO 102
<211> LENGTH: 21
<212> TYPE: DNA
<213> ORGANISM: Artificial Sequence
<220> FEATURE:
<223> OTHER INFORMATION: primer ex35-R

<400> SEQUENCE: 102
tctgaattgt ggactccctg t                                                 21

<210> SEQ ID NO 103
<211> LENGTH: 20
<212> TYPE: DNA
<213> ORGANISM: Artificial Sequence
<220> FEATURE:
<223> OTHER INFORMATION: primer ex36-F

<400> SEQUENCE: 103
tcccagtgga aagtcctgtt                                                   20

<210> SEQ ID NO 104
<211> LENGTH: 20
<212> TYPE: DNA
<213> ORGANISM: Artificial Sequence
<220> FEATURE:
<223> OTHER INFORMATION: primer ex36-R

<400> SEQUENCE: 104
ttgatctgtt tggcaagtcg                                                   20

<210> SEQ ID NO 105
<211> LENGTH: 20
<212> TYPE: DNA
<213> ORGANISM: Artificial Sequence
<220> FEATURE:
<223> OTHER INFORMATION: primer ex37-F

<400> SEQUENCE: 105
gaaggagcag cagtgtggtt                                                   20

<210> SEQ ID NO 106
<211> LENGTH: 20
<212> TYPE: DNA
<213> ORGANISM: Artificial Sequence
<220> FEATURE:
<223> OTHER INFORMATION: primer ex37-R
```

-continued

```
<400> SEQUENCE: 106
aatgttgacc gcctttgttc                                              20

<210> SEQ ID NO 107
<211> LENGTH: 19
<212> TYPE: DNA
<213> ORGANISM: Artificial Sequence
<220> FEATURE:
<223> OTHER INFORMATION: primer ex38-F

<400> SEQUENCE: 107
ccaggacctc accacacag                                               19

<210> SEQ ID NO 108
<211> LENGTH: 20
<212> TYPE: DNA
<213> ORGANISM: Artificial Sequence
<220> FEATURE:
<223> OTHER INFORMATION: primer ex38-R

<400> SEQUENCE: 108
actctgggtc tgggtgacca                                              20

<210> SEQ ID NO 109
<211> LENGTH: 21
<212> TYPE: DNA
<213> ORGANISM: Artificial Sequence
<220> FEATURE:
<223> OTHER INFORMATION: primer ex39-F

<400> SEQUENCE: 109
gctgtcccac acatgaaata a                                            21

<210> SEQ ID NO 110
<211> LENGTH: 19
<212> TYPE: DNA
<213> ORGANISM: Artificial Sequence
<220> FEATURE:
<223> OTHER INFORMATION: primer ex39-R

<400> SEQUENCE: 110
acacctctgc gtgggactc                                               19

<210> SEQ ID NO 111
<211> LENGTH: 20
<212> TYPE: DNA
<213> ORGANISM: Artificial Sequence
<220> FEATURE:
<223> OTHER INFORMATION: primer ex40-F

<400> SEQUENCE: 111
gctgcctctg tttctttgct                                              20

<210> SEQ ID NO 112
<211> LENGTH: 20
<212> TYPE: DNA
<213> ORGANISM: Artificial Sequence
<220> FEATURE:
<223> OTHER INFORMATION: primer ex40-R

<400> SEQUENCE: 112
ctctgggtgg gttctggtta                                              20
```

<210> SEQ ID NO 113
<211> LENGTH: 20
<212> TYPE: DNA
<213> ORGANISM: Artificial Sequence
<220> FEATURE:
<223> OTHER INFORMATION: primer ex41-F

<400> SEQUENCE: 113
gcacctccca tcactgtctc                                            20

<210> SEQ ID NO 114
<211> LENGTH: 20
<212> TYPE: DNA
<213> ORGANISM: Artificial Sequence
<220> FEATURE:
<223> OTHER INFORMATION: primer ex41-R

<400> SEQUENCE: 114
ctacattaag cgggccattg                                            20

<210> SEQ ID NO 115
<211> LENGTH: 25
<212> TYPE: DNA
<213> ORGANISM: Artificial Sequence
<220> FEATURE:
<223> OTHER INFORMATION: primer ex42-F

<400> SEQUENCE: 115
agagactgtc gcctgaatgg gtgac                                      25

<210> SEQ ID NO 116
<211> LENGTH: 26
<212> TYPE: DNA
<213> ORGANISM: Artificial Sequence
<220> FEATURE:
<223> OTHER INFORMATION: primer ex42-R

<400> SEQUENCE: 116
gacgttaggg acacgaaagt ctgtgg                                     26

<210> SEQ ID NO 117
<211> LENGTH: 19
<212> TYPE: DNA
<213> ORGANISM: Artificial Sequence
<220> FEATURE:
<223> OTHER INFORMATION: primer ex43-F

<400> SEQUENCE: 117
ctggccacag tgagaggag                                             19

<210> SEQ ID NO 118
<211> LENGTH: 19
<212> TYPE: DNA
<213> ORGANISM: Artificial Sequence
<220> FEATURE:
<223> OTHER INFORMATION: primer ex43-R

<400> SEQUENCE: 118
gacccatgcc agagaggat                                             19

<210> SEQ ID NO 119
<211> LENGTH: 20
<212> TYPE: DNA
<213> ORGANISM: Artificial Sequence
<220> FEATURE:
<223> OTHER INFORMATION: primer ex44-F

```
<400> SEQUENCE: 119
actcggagca agagagtgga                                                    20

<210> SEQ ID NO 120
<211> LENGTH: 20
<212> TYPE: DNA
<213> ORGANISM: Artificial Sequence
<220> FEATURE:
<223> OTHER INFORMATION: primer ex44-R

<400> SEQUENCE: 120
gaacacaaga ggacgcaatg                                                    20

<210> SEQ ID NO 121
<211> LENGTH: 20
<212> TYPE: DNA
<213> ORGANISM: Artificial Sequence
<220> FEATURE:
<223> OTHER INFORMATION: primer ex45-F

<400> SEQUENCE: 121
cattgcgtcc tcttgtgttc                                                    20

<210> SEQ ID NO 122
<211> LENGTH: 20
<212> TYPE: DNA
<213> ORGANISM: Artificial Sequence
<220> FEATURE:
<223> OTHER INFORMATION: primer ex45-R

<400> SEQUENCE: 122
agcactagga cctgggaagg                                                    20

<210> SEQ ID NO 123
<211> LENGTH: 20
<212> TYPE: DNA
<213> ORGANISM: Artificial Sequence
<220> FEATURE:
<223> OTHER INFORMATION: primer ex46-F

<400> SEQUENCE: 123
gggctgctct ctctctcttt                                                    20

<210> SEQ ID NO 124
<211> LENGTH: 24
<212> TYPE: DNA
<213> ORGANISM: Artificial Sequence
<220> FEATURE:
<223> OTHER INFORMATION: primer ex46-R

<400> SEQUENCE: 124
aacttaccag ccgtggaggg tttg                                               24

<210> SEQ ID NO 125
<211> LENGTH: 25
<212> TYPE: DNA
<213> ORGANISM: Artificial Sequence
<220> FEATURE:
<223> OTHER INFORMATION: primer ex47-1-F

<400> SEQUENCE: 125
ggccctccag taggtggcta aactc                                              25
```

```
<210> SEQ ID NO 126
<211> LENGTH: 25
<212> TYPE: DNA
<213> ORGANISM: Artificial Sequence
<220> FEATURE:
<223> OTHER INFORMATION: primer ex47-1-R

<400> SEQUENCE: 126
ggctgatgta gggcttgatc tcgtc                                    25

<210> SEQ ID NO 127
<211> LENGTH: 25
<212> TYPE: DNA
<213> ORGANISM: Artificial Sequence
<220> FEATURE:
<223> OTHER INFORMATION: primer ex47-2-F

<400> SEQUENCE: 127
tcctgtactg caaccctggt gatgt                                    25

<210> SEQ ID NO 128
<211> LENGTH: 25
<212> TYPE: DNA
<213> ORGANISM: Artificial Sequence
<220> FEATURE:
<223> OTHER INFORMATION: primer ex47-2-R

<400> SEQUENCE: 128
caaaggcagc tgttcttgct gtgtc                                    25

<210> SEQ ID NO 129
<211> LENGTH: 25
<212> TYPE: DNA
<213> ORGANISM: Artificial Sequence
<220> FEATURE:
<223> OTHER INFORMATION: primer ex48-F

<400> SEQUENCE: 129
caggctgtga ttcctaaccc tgtcc                                    25

<210> SEQ ID NO 130
<211> LENGTH: 25
<212> TYPE: DNA
<213> ORGANISM: Artificial Sequence
<220> FEATURE:
<223> OTHER INFORMATION: primer ex48-R

<400> SEQUENCE: 130
gaataagcac caaaatggcc cttcc                                    25

<210> SEQ ID NO 131
<211> LENGTH: 25
<212> TYPE: PRT
<213> ORGANISM: Homo sapiens

<400> SEQUENCE: 131

Gly Val Gln Gly Pro Pro Gly Leu Lys Gly Gln Thr Gly Phe Pro Gly
1               5                   10                  15

Leu Thr Gly Pro Pro Gly Ser Gln Gly
            20                  25

<210> SEQ ID NO 132
<211> LENGTH: 26
<212> TYPE: PRT
<213> ORGANISM: Homo sapiens
```

```
<400> SEQUENCE: 132

Gly Leu Pro Gly Arg Pro Gly His Ile Lys Gly Val Lys Gly Asp Ile
1               5                   10                  15

Gly Val Pro Gly Ile Pro Gly Leu Pro Gly
            20                  25

<210> SEQ ID NO 133
<211> LENGTH: 25
<212> TYPE: PRT
<213> ORGANISM: Mus musculus

<400> SEQUENCE: 133

Gly Ala Gln Gly Ser Pro Gly Leu Lys Gly Gln Thr Gly Phe Pro Gly
1               5                   10                  15

Leu Thr Gly Leu Gln Gly Pro Gln Gly
            20                  25

<210> SEQ ID NO 134
<211> LENGTH: 26
<212> TYPE: PRT
<213> ORGANISM: Mus musculus

<400> SEQUENCE: 134

Gly Leu Pro Gly Arg Pro Gly Phe Ile Lys Gly Val Lys Gly Asp Ile
1               5                   10                  15

Gly Val Pro Gly Thr Pro Gly Leu Pro Gly
            20                  25

<210> SEQ ID NO 135
<211> LENGTH: 25
<212> TYPE: PRT
<213> ORGANISM: Gallus gallus

<400> SEQUENCE: 135

Gly Ile Gln Gly Val Pro Gly Ser Leu Gly Gln Lys Gly Leu Pro Gly
1               5                   10                  15

Leu Val Gly Pro Pro Gly Gln Gln Gly
            20                  25

<210> SEQ ID NO 136
<211> LENGTH: 26
<212> TYPE: PRT
<213> ORGANISM: Gallus gallus

<400> SEQUENCE: 136

Gly Ser Pro Gly His Pro Ser Tyr Val Pro Gly Val Lys Gly Asp Ile
1               5                   10                  15

Gly Ala Lys Gly Leu Thr Gly Leu Lys Gly
            20                  25

<210> SEQ ID NO 137
<211> LENGTH: 25
<212> TYPE: PRT
<213> ORGANISM: Xenopus tropicalis

<400> SEQUENCE: 137

Gly Glu His Gly Gln Thr Gly Glu Lys Gly Phe Pro Gly Gln Gln Gly
1               5                   10                  15

Leu Val Gly Phe Pro Gly Ser Gln Gly
            20                  25
```

-continued

<210> SEQ ID NO 138
<211> LENGTH: 26
<212> TYPE: PRT
<213> ORGANISM: Xenopus tropicalis

<400> SEQUENCE: 138

Gly Leu Pro Gly Leu Arg Ser Phe Glu Phe Gly Asp Lys Gly Glu Thr
1               5                   10                  15

Gly Thr Pro Gly Val Ile Gly Asn Gln Gly
            20                  25

<210> SEQ ID NO 139
<211> LENGTH: 25
<212> TYPE: PRT
<213> ORGANISM: Dania rerio

<400> SEQUENCE: 139

Gly Asp Gln Gly Ser Ile Gly Tyr Pro Gly Ser Pro Gly Lys Pro Gly
1               5                   10                  15

Glu Lys Gly Val Gly Gly Leu Pro Gly
            20                  25

<210> SEQ ID NO 140
<211> LENGTH: 25
<212> TYPE: PRT
<213> ORGANISM: Dania rerio

<400> SEQUENCE: 140

Gly Met Pro Gly Ser Pro Gly Gln Pro Gly Asp Lys Gly Asp Pro Gly
1               5                   10                  15

Ile Ile Gly Lys Pro Gly Ser Ile Gly
            20                  25

<210> SEQ ID NO 141
<211> LENGTH: 29
<212> TYPE: PRT
<213> ORGANISM: Drosophila melanogaster

<400> SEQUENCE: 141

Gly Glu Gln Gly Glu Gln Gly Glu Gln Gly Asp Glu Gly Glu Val Gly
1               5                   10                  15

Ile Pro Gly Arg Leu Glu Asn Leu Arg Asp Arg Ser Phe
            20                  25

<210> SEQ ID NO 142
<211> LENGTH: 27
<212> TYPE: PRT
<213> ORGANISM: Drosophila melanogaster

<400> SEQUENCE: 142

Gly Tyr Pro Gly Ala Pro Gly Val Lys Gly Gln Arg Gly Pro Val Gly
1               5                   10                  15

Asp Ser Gln Pro Ala Leu Asp Gly Val Ala Gly
            20                  25

<210> SEQ ID NO 143
<211> LENGTH: 25
<212> TYPE: PRT
<213> ORGANISM: Caenorhabditis elegans

```
<400> SEQUENCE: 143

Gly Met Asp Gly Tyr Pro Gly Gln Lys Gly Glu Asn Gly Tyr Pro Gly
1               5                   10                  15

Gln Pro Gly Leu Pro Gly Leu Gly Gly
            20              25

<210> SEQ ID NO 144
<211> LENGTH: 24
<212> TYPE: PRT
<213> ORGANISM: Caenorhabditis elegans

<400> SEQUENCE: 144

Gly Leu Pro Gly Tyr Gly Gln Pro Gly Gln Pro Gly Glu Lys Gly Leu
1               5                   10                  15

Pro Gly Ile Pro Gly Lys Ala Gly
            20
```

METHOD FOR PREDICTING RISK OF PORENCEPHALY OR CEREBRAL HEMORRHAGE

REFERENCE TO SEQUENCE LISTING SUBMITTED VIA EFS-WEB

This application includes an electronically submitted sequence listing in .txt format. The .txt file contains a sequence listing entitled "2016-10-14 0760-0440PUS1 ST25.txt" created on Oct. 14, 2016 and is 113,239 bytes in size. The sequence listing contained in this .txt file is part of the specification and is hereby incorporated by reference herein in its entirety.

TECHNICAL FIELD

The present invention relates to a method for predicting porencephaly and/or cerebral hemorrhage.

BACKGROUND ART

Porencephaly is a congenital disorder in which a cyst or cavity communicating with the cerebral ventricle is found in the cerebral hemisphere (Non-patent Document 1), and assumed to be caused by a disturbance of vascular supply such as infarction or hemorrhage during the fetal period (Non-patent Documents 2 and 3). Clinically, porencephaly causes hemiplegia (most often), quadriplegia, epilepsy, and intellectual disability (Non-patent Documents 4 and 5). Delivery of monozygous twins, cardiac arrest or abdominal trauma of the mother, a deficient protein C anticoagulant pathway, and cytomegalovirus infection are risk factors for sporadic porencephaly (Non-patent Documents 2 and 6).

In recent years, mutations in the gene encoding the α1 chain of type IV collagen (COL4A1, MIM 120130) were reported to be responsible for familial porencephaly (Non-patent Document 7). After that, de novo mutations in the COL4A1 gene were also reported in a sporadic case (Non-patent Documents 8 to 10), confirming involvement of abnormality of the COL4A1 gene in both sporadic and familial porencephalies. However, there still remain many cases in which no mutation in the COL4A1 gene can be identified.

PRIOR ART DOCUMENTS

Non-Patent Documents

Non-patent Document 1: Berg, R. A., Aleck, K. A., and Kaplan, A. M. (1983). Familial porencephaly. Arch. Neurol. 40, 567-569.
Non-patent Document 2: Govaert, P. (2009). Prenatal stroke. Semin Fetal Neonatal Med 14, 250-266.
Non-patent Document 3: Hunter, A. (2006). Porencephaly. In Human Malformations and related Anomalies, S. R E and H. J G, eds. (New York, Oxford University Press), pp 645-654.
Non-patent Document 4: Mancini, G. M., de Coo, I. F., Lequin, M. H., and Arts, W. F. (2004). Hereditary porencephaly: clinical and MRI findings in two Dutch families. Eur J Paediatr Neurol 8, 45-54.
Non-patent Document 5: Vilain, C., Van Regemorter, N., Verloes, A., David, P., and Van Bogaert, P. (2002). Neuroimaging fails to identify asymptomatic carriers of familial porencephaly. Am J Med Genet 112, 198-202.
Non-patent Document 6: Moinuddin, A., McKinstry, R. C., Martin, K. A., and Neil, J. J. (2003). Intracranial hemorrhage progressing to porencephaly as a result of congenitally acquired cytomegalovirus infection—an illustrative report. Prenat Diagn 23, 797-800.
Non-patent Document 7: Gould, D. B., Phalan, F. C., Breedveld, G. J., van Mil, S. E., Smith, R. S., Schimenti, J. C., Aguglia, U., van der Knaap, M. S., Heutink, P., and John, S. W. (2005). Mutations in Col4a1 cause perinatal cerebral hemorrhage and porencephaly. Science 308, 1167-1171.
Non-patent Document 8: Breedveld, G., de Coo, I. F., Lequin, M. H., Arts, W. F., Heutink, P., Gould, D. B., John, S. W., Oostra, B., and Mancini, G. M. (2006). Novel mutations in three families confirm a major role of COL4A1 in hereditary porencephaly. J Med Genet 43, 490-495.
Non-patent Document 9: Lanfranconi, S., and Markus, H. S. (2010). COL4A1 mutations as a monogenic cause of cerebral small vessel disease: a systematic review. Stroke 41, e513-518.
Non-patent Document 10: Meuwissen, M. E., de Vries, L. S., Verbeek, H. A., Lequin, M. H., Govaert, P. P., Schot, R., Cowan, F. M., Hennekam, R., Rizzu, P., Verheijen, F. W., et al. (2011). Sporadic COL4A1 mutations with extensive prenatal porencephaly resembling hydranencephaly. Neurology 76, 844-846.

SUMMARY OF THE INVENTION

Problems to be Solved by the Invention

The present invention aims to identify a novel causative gene for porencephaly and to provide a novel means that can be used for prevention of cerebral hemorrhage during the fetal period to perinatal period.

Means for Solving the Problems

The present inventors focused on COL4A2 protein, which forms a heterotrimer with COL4A1 protein, and intensively screened for COL4A2 mutations in 35 Japanese patients with porencephaly. As a result, the present inventors successfully identified heterozygous mutations in 2 patients. Two mutations were not found in populations of healthy Japanese individuals, and their pathogenicity was strongly suggested by evaluation using pathogenicity prediction tools. One of the 2 patients represented a sporadic case, and the other represented a familial case. That is, the present inventors discovered that the COL4A2 gene is a causative gene for both familial and sporadic porencephalies, thereby completing the present invention.

That is, the present invention provides a method for predicting risk of porencephaly and/or cerebral hemorrhage, which is carried out for a sample separated from a living body, said method comprising investigating whether or not at least one mutation is present in the COL4A2 gene in a subject living body, wherein, in the case where at least one mutation is present in at least one allele of the COL4A2 gene, high risk of porencephaly and/or cerebral hemorrhage is predicted.

EFFECT OF THE INVENTION

By the present invention, the COL4A2 gene was identified as a causative gene for porencephaly for the first time, and a novel method for predicting the risk of porencephaly and/or cerebral hemorrhage, especially porencephaly and/or cerebral hemorrhage during the fetal period to perinatal period, was provided. Since an identical heterozygous mutation of the COL4A2 gene was found in both a porencephaly patient and healthy individuals, this pathogenic mutation is considered to be dominantly inherited with incomplete penetrance. In cases where a COL4A2 mutation is found in at least one of the parents of a fetus, the COL4A2 mutation might be inherited to the fetus. It is also possible to investigate whether or not the COL4A2 mutation is present in the fetus itself by prenatal diagnosis. In cases where there is a concern about the risk of occurrence of porencephaly or cerebral hemorrhage during the fetal period to perinatal period, perinatal cerebral hemorrhage can be prevented by avoiding vaginal delivery, and positively selecting cesarean section, which is less likely to cause physical damages to the fetus. Further, since the COL4A2 gene is a gene associated with fragility of blood vessels, it is thought that healthy carriers have higher risk of hemorrhagic cerebrovascular diseases than healthy non-carriers. Therefore, healthy carriers should place emphasis on prevention of hemorrhagic cerebrovascular diseases. Thus, the present invention can also contribute to prevention of cerebral hemorrhage in adults.

BRIEF DESCRIPTION OF THE DRAWINGS

FIG. 1A Pedigree of patient 1 with porencephaly, in whom the c.3455G>A (p.G1152D) mutation was identified in the COL4A2 gene. The arrow indicates the patient 1. A maternal uncle (III-1) of the patient had congenital left hemiplegia. The patient's mother (III-2) and maternal grandfather (II-7) were both healthy. The elder granduncle (II-5) was also afflicted by congenital hemiplegia and died in his 60s. FIG. 1B Pedigree of patient 2 with porencephaly, in whom the c.3110G>A (p.G1037E) mutation was identified in the COL4A2 gene. The arrow indicates the patient 2. His parents did not have this mutation, indicating that the mutation occurred de novo. FIG. 1C Electropherogram of the genomic sequence of the mutation. The left panel shows data from the patient 1 and his parents, and the right panel shows data from the patient 2 and his parents. FIG. 1D Amino acid sequence alignments of the COL4A2 protein.

Figure 2:
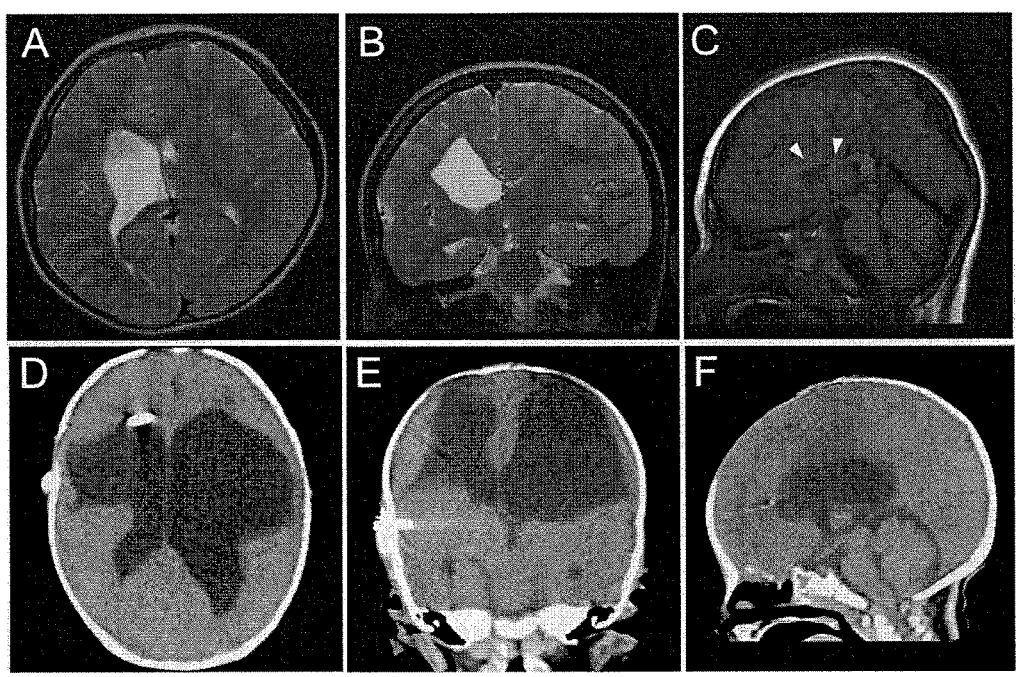

Evolutionarily conserved amino acids are highlighted with gray or black boxes in the figure. Each black box indicates a Gly residue that showed a mutation. The respective amino acid sequences were obtained from the NCBI protein database: NP_001837.2 (*Homo sapiens*)(SEQ ID NOS: 131 and 132), NP_034062.3 (*Mus musculus*) (SEQ ID NOS: 133 and 134), NP_001155862.1 (*Gallus gallus*), (SEQ ID NOS: 135 and 136), XP_002933063.1 (*Xenopus tropicalis*) (SEQ ID NOS: 137 and 138), XP_687811.5 (*Danio rerio*) (SEQ ID NOS: 139 and 140), AAB64082.1 (*Drosophila melanogaster*) (SEQ ID NOS: 141 and 142), and CAA80537.1 (*Caenorhabditis elegans*) (SEQ ID NOS: 143 and 144). The alignment was performed with CLUSTAL W as shown in the website of clustalw.ddbj.nig.ac.jp.

FIG. 2 (A-C) Brain MRIs of the patient 1 at 6 years old. (A) T2-weighted cross-sectional image. (B) Coronal image. The images in (A) and (B) show an enlarged right lateral ventricle and reduced volume of the right frontal white matter. (C) T1 weighted midline sagittal image showing atrophy of the body of corpus callosum (arrowheads). The lesion responsible for the left leg paresis is not evident in these images. (D-F) CT images of the patient 2 at two months of age. (D) Cross-sectional image. (E) Coronal image. (F) Sagittal image. The images in (D), (E) and (F) show bilateral enlargement of the lateral ventricle and extremely reduced volume of bilateral frontal white matter. The V-P shunt is also visible in the right lateral ventricle. The pontocerebellar structures seem to be normal.

FIG. 3 Amino acid sequence of the α2 chain of type IV collagen (SEQ ID NO: 2), which is encoded by the COL4A2 gene. The underlined portions are Gly-Xaa-Yaa repeat regions. Black boxes indicate the Gly residues involved in the 2 kinds of amino acid substitution mutations identified in Examples.

BEST MODE FOR CARRYING OUT THE INVENTION

The COL4A2 gene (MIM 120090), identified as a novel causative gene for porencephaly by the present inventors, encodes the α2 chain of type IV collagen. Type IV collagen is a basement membrane protein expressed in all tissues including the vasculature. Among type IV collagens, the most abundant collagens are COL4A1 (α1 chain) and COL4A2 (α2 chain), and these are known to form a heterotrimer (α1α1α2) at a ratio of 2:1 (Khoshnoodi, J., Pedchenko, V., and Hudson, B. G. (2008). Mammalian collagen IV. Microsc Res Tech 71, 357-370.). In the domain that forms the heterotrimer, there are Gly-Xaa-Yaa repeats (wherein Xaa and Yaa represent the same or different arbitrary amino acids), and a triple-helix structure is formed in this repeat region. The positions of the Gly-Xaa-Yaa repeats are indicated by underlines in FIG. 3. SEQ ID NOs: 1 and 2 in SEQUENCE LISTING are a sequence of the coding region in cDNA of the COL4A2 gene, and an amino acid sequence of COL4A2 protein, respectively. SEQ ID NO:3 is a mRNA sequence deposited in GenBank (accession number NM_001846). In SEQ ID NOs 4 to 38, sequences of exons and their proximal introns are shown as listed in Table 1.

TABLE 1

| SEQ ID NO: | | Exon |
|---|---|---|
| Ex1 | 4 | 101-345 nt (UTR 101-345 nt) |
| Ex2 | 4 | 677-764 nt (UTR 677-720 nt) |
| Ex3 | 4 | 886-940 nt |
| Ex4 | 5 | 301-381 nt |
| Ex5 | 6 | 301-435 nt |
| Ex6 | 6 | 520-564 nt |
| Ex7 | 7 | 301-417 nt |
| Ex8 | 8 | 301-372 nt |
| Ex9 | 8 | 817-852 nt |
| Ex10 | 8 | 961-1023 nt |
| Ex11 | 9 | 301-336 nt |
| Ex12 | 10 | 301-342 nt |
| Ex13 | 11 | 301-399 nt |
| Ex14 | 12 | 301-336 nt |
| Ex15 | 12 | 917-967 nt |
| Ex16 | 13 | 301-345 nt |
| Ex17 | 14 | 301-354 nt |
| Ex18 | 15 | 301-367 nt |
| Ex19 | 16 | 301-411 nt |
| Ex20 | 16 | 927-1076 nt |
| Ex21 | 17 | 301-393 nt |
| Ex22 | 18 | 301-464 nt |
| Ex23 | 19 | 301-373 nt |
| Ex24 | 19 | 465-571 nt |
| Ex25 | 20 | 301-502 nt |
| Ex26 | 20 | 899-958 nt |
| Ex27 | 21 | 301-357 nt |
| Ex28 | 22 | 301-408 nt |
| Ex29 | 23 | 301-522 nt |
| Ex30 | 24 | 301-462 nt |
| Ex31 | 25 | 301-471 nt |
| Ex32 | 26 | 301-444 nt |

TABLE 1-continued

| SEQ ID NO: | | Exon |
|---|---|---|
| Ex33 | 27 | 301-423 nt |
| Ex34 | 28 | 301-482 nt |
| Ex35 | 29 | 301-364 nt |
| Ex36 | 29 | 567-641 nt |
| Ex37 | 30 | 301-408 nt |
| Ex38 | 31 | 301-408 nt |
| Ex39 | 32 | 301-372 nt |
| Ex40 | 33 | 301-426 nt |
| Ex41 | 34 | 301-417 nt |
| Ex42 | 35 | 301-462 nt |
| Ex43 | 35 | 563-661 nt |
| Ex44 | 35 | 1027-1173 nt |
| Ex45 | 35 | 1328-1444 nt |
| Ex46 | 36 | 301-492 nt |
| Ex47 | 37 | 301-587 nt |
| Ex48 | 38 | 301-1163 nt (UTR 329-1163 nt) |

In the present invention, mutations in the COL4A2 gene are used as indices for predicting the risk of occurrence of porencephaly and/or cerebral hemorrhage in a subject living body. The subject living body is preferably a postnatal human (for example, human adult) or human fetus. The cerebral hemorrhage includes cerebral hemorrhage during the fetal period to perinatal period, and hemorrhagic cerebrovascular diseases that occur in adulthood (including old age). In cases where at least one mutation is present in at least one of the alleles of the COL4A2 gene, high risk of porencephaly and cerebral hemorrhage can be predicted. A heterozygous mutation has been found in both a porencephaly patient and healthy carriers, indicating that the mode of heredity is dominant inheritance with incomplete penetrance.

The mutations in the COL4A2 gene used as indices in the present invention include changes in the base sequence that cause changes in a very small number of amino acids in the α2 chain of type IV collagen, which is encoded by the COL4A2 gene, or those that cause deletion of at least a partial region in the α2 chain. The mutations also include mutations that cause deletion of all or part of the COL4A2 gene region. Specific examples of such mutations of the base sequence include missense mutations, nonsense mutations, frameshift mutations, in-frame deletion or insertion mutations (which causes deletion or insertion of one or more amino acids) due to substitution, deletion, insertion, duplication and/or the like of a base(s) in an exon and/or intron region(s); mutations that cause abnormal splicing; and microdeletions of the chromosomal region containing the COL4A2 gene.

Mutations in the COL4A2 gene can be detected by analyzing the base sequence using a nucleic acid sample such as genomic DNA or RNA. In particular, analysis of a genomic sequence using a genomic DNA sample is desirable since such analysis is most accurate. The nucleic acid sample such as genomic DNA can be easily prepared from peripheral blood, a swab of oral mucosa or the like by a conventional method. Various prenatal genetic testing methods are known, and it is also possible to investigate whether a fetus has a mutation in the COL4A2 gene or not. Examples of the various known methods include a method in which cells are collected from the fetus (using amniotic fluid, villi or cord blood), a noninvasive test method in which a genetic mutation of the fetus is tested using fetal cells present in maternal blood, and a method in which a single cell of the fertilized egg obtained by external fertilization is used (preimplantation diagnosis). In the noninvasive test method, the maternal blood sample containing fetal cells corresponds to the "sample separated from a living body", and the fetus corresponds to the "subject living body".

Although the amino acid sequence of a protein may be influenced by mutations in not only exon regions but also intron regions, each exonic sequences and its adjacent ten to several hundred bases such as about 30 to 50 bases of the intron region are commonly tested in usual genetic testing. Also in the present invention, each exon and its adjacent intron may be sequenced. When detection of mutations is carried out by analysis of a genomic sequence, sequencing may be carried out by a normal method using a genomic DNA sample with primers designed as appropriate by reference to SEQ ID NOs:4 to 38 of the present application or genomic sequence of the COL4A2 gene available from known databases. By determining the base sequence of the COL4A2 gene on the genomic DNA of the subject living body and comparing the determined sequence with a wild-type sequence, a mutation(s) can be identified in detail. Detection of the mutation(s) and profiling of the determined base sequence can be easily carried out by analysis using known software such as SeqScape (registered trademark).

Whether a mutation is homozygous or heterozygous can be confirmed with the waveform data obtained by sequencing. In the case where a heterozygous mutation is present, 2 types of signals overlap with each other at the same position.

Since COL4A2 gene mutation(s) to be detected in the present invention is/are mainly heterozygous, the screening of COL4A2 gene mutations can be effectively carried out by detection of heteroduplexes. If a heterozygous mutation is present, heat denaturation of the genomic DNA sample followed by reassociation produces heteroduplexes by hybridization between the normal-type DNA and the mutant-type DNA. The heteroduplexes have properties including the followings: (1) heteroduplexes show a different mobility in nondenaturing polyacrylamide gel; (2) mismatched bases are more susceptible to cleavage by chemical substances and enzymes; (3) heteroduplexes show a different melting temperature upon denaturation. Methods for detecting heteroduplexes utilizing these properties are known in the art, and practically used as test methods for mutations. More specifically, examples of the known methods include a method in which heteroduplexes are detected by denaturing high-performance liquid chromatography (dHPLC), and the High Resolution Melt method.

The High Resolution Melt method is a method in which the process of melting of double-stranded DNA (heat denaturation) is detected as a change in the fluorescence intensity using a fluorescent dye that binds to double-stranded DNA at high density (e.g., SYTO (registered trademark) 9, LC Green (registered trademark), or EvaGreen (registered trademark)), thereby detecting heteroduplexes. That is, when double-stranded DNA stained with a fluorescent dye that binds to double-stranded DNA at high density is melted (heat-denatured), the fluorescent dye drops from the portion where dissociation of the double strand occurred, which results in a decrease in the fluorescence signal from the double-stranded DNA. Therefore, by using such a fluorescent dye, the process of heat denaturation of double-stranded DNA can be visually detected as a change in the fluorescence intensity. By obtaining and analyzing temperature-fluorescence data at high density, detection of heteroduplexes can be carried out rapidly and highly sensitively. This can be easily carried out using a commercially available device and kit and the like. The primers used can be designed as appropriate based on the sequence of each exon+adjacent intron region in the COL4A2 gene described in SEQUENCE LISTING of the present application. In the Examples below, examples of primers and reaction conditions that can be used for screening of COL4A2 gene mutations by the High Resolution Melt method are shown.

In the present invention, the presence/absence of a mutation may be determined by sequencing all the exon+adjacent intron regions in the COL4A2 gene. Alternatively, for example, detection of heteroduplexes may be carried out to narrow down the regions to be sequenced, and thereafter the target regions may be sequenced, thereby carrying out the testing more effectively.

The cDNA sequence and genomic sequence of the COL4A2 gene and the amino acid sequence of the COL4A2 protein encoded thereby shown in SEQUENCE LISTING are typical examples of normal COL4A2 sequences. In the present invention, the presence/absence of a mutation can be judged by using the COL4A2 gene sequence shown in SEQUENCE LISTING as a reference and performing comparison with this reference sequence. A mutation of the COL4A2 gene that causes alteration of the amino acid sequence can be regarded as a pathogenic mutation for porencephaly and cerebral hemorrhage. In particular, a gene mutation that alters an amino acid that is evolutionarily highly conserved is highly likely to produce a COL4A2 protein whose normal function is deteriorated, for example, a COL4A2 protein that cannot qualitatively or quantitatively form the normal α1α1α2 heterotrimer, and such a gene mutation is therefore a typical example of the pathogenic mutation for porencephaly and cerebral hemorrhage. Sequences of COL4A2 protein (type IV collagen α2 chain) of various animals are known, and deposited in databases such as GenBank. Therefore, those skilled in the art can easily obtain the sequence information, and investigate evolutionary conservation of each amino acid by a conventional method. Representative examples of the mutation of an evolutionarily conserved amino acid residue include mutations that substitute Gly in the Gly-Xaa-Yaa repeats (wherein Xaa and Yaa represent the same or different arbitrary amino acids), which are the triple helix domain of the heterotrimer. Further, also in cases where the detected base mutation is a mutation that is not found in populations of many healthy individuals or a mutation that has not been deposited in well-known databases related to diversity of base sequences such as dbSNP by NCBI or 1000 Genomes Project, the mutation can be regarded as a pathogenic mutation that can be used as an index in the present invention.

Various prediction tools with which whether a mutation in a gene is a pathogenic mutation or not can be investigated are known. Examples of such tools include SIFT (http://sift.jcvi.org/), PolyPhen (http://genetics.bwh.harvard.edu/pph/), PolyPhen-2 (http://genetics.bwh.harvard.edu/pph2/), Mutation Taster (http://neurocore.charite.de/MutationTaster/index.html) and Align GVGD (http://agvgd.iarc.fr/agvgd_input.php). In cases where a mutation of the COL4A2 gene has been detected by carrying out the method of the present invention and whether the mutation is pathogenic or not is uncertain, such a prediction tool may be used to judge whether the mutation is pathogenic or not. In SIFT, a substitution is predicted to be intolerant (having influence on a protein functional change) when the score is less than 0.05. In PolyPhen, pathogenicity is predicted when the score exceeds 2.0. In PolyPhen-2, the score ranges from 0.000 (most probably benign) to 0.999 (most probably damaging), and when the judgment based on the score is possibly or probably damaging, the mutation is strongly suggested to be pathogenic. In Align GVGD, the class score is evaluated within the range of Class C0 (less likely) to Class C65 (most likely), and a COL4A2 mutation with a class score of C55 or higher is suggested to be a pathogenic mutation.

The mutations shown in Table 2 are two kinds of pathogenic mutations for porencephaly and cerebral hemorrhage, which were identified in two unrelated pedigrees in Examples. All of these mutations are substitution mutations in evolutionarily conserved Gly residues in the Gly-Xaa-Yaa repeats, and not found in the population of many Japanese healthy individuals. These mutations were strongly suggested to be pathogenic based on evaluation using the above-described prediction tools. However, these two kinds of mutations are mere examples of COL4A2 gene mutations that can be used as indices in the present invention, and, of course, pedigrees other than these two pedigrees may have different pathogenic mutations. Therefore, the scope of the present invention is not limited to these specific examples.

TABLE 2

| COL4A2 Gene Mutations | | | |
|---|---|---|---|
| DNA mutation | Amino acid mutation | Exon | Specification of mutation site in SEQUENCE LISTING |
| c.3455G > A | G→D at position 1152 | 38 | Position 3455 in SEQ ID NO: 1<br>Position 301 in SEQ ID NO: 31 |
| c.3110G > A | G→E at position 1037 | 34 | Position 3110 in SEQ ID NO: 1<br>Position 385 in SEQ ID NO: 28 |

In cases where one or more COL4A2 gene mutations are found in at least one of the parents, the mutation might be inherited to the fetus. Therefore, the risk of occurrence of porencephaly and/or cerebral hemorrhage during the fetal period to perinatal period in the fetus can be predicted to be higher than usual. Since a method of prenatal diagnosis in which a gene of a fetus is investigated is known and already being practically used, whether or not the fetus itself actually has a COL4A2 gene mutation that has been inherited from a parent or occurred de novo may be investigated, if desired. In cases where there is a concern about the risk of occurrence of porencephaly and/or cerebral hemorrhage during the fetal period to perinatal period, vaginal delivery may give physical damage to the fetus to cause cerebral hemorrhage. Therefore, positive selection of cesarean section is effective for avoiding cerebral hemorrhage during the perinatal period. Thus, the present invention can be utilized for selecting a safe delivery method.

In cases where a COL4A2 gene mutation was found in a postnatal healthy subject living body, the subject living body is considered to have higher risk of cerebral hemorrhage than a healthy individual who does not have the COL4A2 gene mutation, since the COL4A2 gene is a gene associated with fragility of blood vessels. In such cases, emphasis should be placed on prevention of hemorrhagic cerebrovascular diseases by, for example, paying sufficient attention to the lifestyle and the dietary life. The present invention can also be utilized for prevention of cerebral hemorrhage in adults.

EXAMPLES

The present invention is described below in more detail by way of Examples. However, the present invention is not limited to the Examples below.

As a result of screening of COL4A2 gene mutations in 35 Japanese patients with porencephaly, substitution of a Gly residue in the Gly-Xaa-Yaa repeat was identified in two patients (patients 1 and 2). Clinical information and peripheral blood samples were obtained from their family members after obtaining written informed consent. Experimental protocols were approved by the Institutional Review Board of Yokohama City University School of Medicine.

Patient 1 is seven years old and was born to non-consanguineous healthy parents (FIG. 1A, arrow). He was born at 36 weeks' gestation with a planned Caesarean section because, at 31 weeks' gestation, an antenatal ultrasound scan revealed an enlarged right lateral ventricle. Apgar scores were 9 at 1 minute and 10 at 5 minutes. He weighed 2,900 g (+1.09 SD) and had a head circumference of 32.5 cm (+0.05 SD). His early development was delayed with poor left hand use and abnormal leg movement. Brain MRI at 6 months showed an enlarged right lateral ventricle. Abrupt vomiting and nausea followed by motionless arrest developed at the age of 10 months. An electroencephalogram (EEG) showed focal spikes in the right frontal region, and carbamazepine treatment was initiated at the age of 12 months. Rehabilitation was started at 10 months of age. The patient started rolling at 12 months, crawling at 18 months, and walking alone at 3 years of age. He had spastic triplegia (diplegia and left hemiplegia) showing hemiplegic and diplegic gait with fluent speech and normal word comprehension. At the age of 5 years, he underwent orthopedic surgery for foot deformity due to spastic paresis. An EEG showed spikes in the right occipital to posterior temporal region and mid central region. Brain MRI at 6 years showed enlarged right lateral ventricle, reduced volume of the right frontal white matter and atrophic right cerebral peduncle and body of corpus callosum (FIG. 2A-C). His IQ score, evaluated at 6 years with WISC-III, was 74 (performance IQ: 69 and verbal IQ: 82). The patient 1 is now 7 years old and attending a local school. He can walk with ankle foot orthosis and hand assist. The epilepsy is well controlled with carbamazepine and clobazam. Of note, his maternal elder uncle showed congenital left hemiplegia with assisted walk, and his maternal granduncle had also been afflicted by congenital hemiplegia, suggesting a genetic predisposition in the family (FIG. 1A).

Patient 2 is one year and four months old and was born to non-consanguineous healthy parents (FIG. 1B, arrow). He was born at 35 weeks' gestation. His birth weight was 1,694 g (~2.36 SD) and his head circumference was 29 cm (−1.77 SD). Mild asphyxia was observed with Apgar scores of 3 at 1 minute and 7 at 5 minutes. An ultrasound scan at 6 hours after birth revealed parenchymal hemorrhage of the right cerebral hemisphere with an enlarged left lateral ventricle. Because a blood test revealed no increase in D-dimer but revealed significant increases in prothrombin time (29.3 sec) and activated partial thromboplastin time (104.3 sec), he was treated with a daily infusion of fresh frozen plasma for 12 days. At 37 days after birth, he underwent a ventricular-peritoneal shunt (V-P shunt) operation because of progressive enlargement of the lateral ventricle. CT at two months of age showed an enlarged bilateral lateral ventricle and an extremely reduced volume of bilateral frontal white matter (FIG. 2D-F). Blood coagulation was normalized at 7 months of age. At the age of 7 months, the patient did not show any head control or rolling, and presented with abnormal posturing and spastic quadriplegia dominant on the left side of his body. With rehabilitation, he had full-range visual pursuit, social smile and incomplete head control. Although his spasticity improved, exaggerated deep tendon reflexes with synergic voluntary movement of the distal part of extremities were recognized. An EEG at one year of age showed no epileptic discharges. His present developmental quotient is below 20. The elder sister of patient 2 was found to have intraventricular hemorrhage two days after birth and underwent a V-P shunt. Her development was almost normal, and internal strabismus was noted. Unfortunately, she died in an accident at the age of four, and so her DNA sample was unavailable (FIG. 1B).

Genomic DNA was isolated from peripheral blood leukocytes according to standard methods. DNA for mutation screening was amplified with illustra GenomiPhi V2 DNA Amplification Kit (GE Healthcare, Buckinghamshire, UK). DNA of familial members of patient 1 was isolated from saliva samples using Oragene (DNA Genotek Inc., Ontario, Canada).

Exons 2 to 48 covering the entire COL4A2 gene coding region (GenBank accession number NM_001846.2) were examined by high-resolution melting curve (HRM) analysis or direct sequencing (for exon 46). Real-time PCR and subsequent High resolution melting analysis were carried out in a 12-μl reaction system using RoterGene-6000 (Corbett Life Science). The composition of the reaction liquid was as follows: for exons 2/3/7/13/24/42/46/47/48, 30 ng of DNA, 0.3 μM each primer, 0.4 mM each dNTP, 1.5 μM SYTO9, 1×PCR Buffer for KOD FX, and 0.3 U KOD FX polymerase; and for the other exons, 30 ng of DNA, 0.25 μM each primer, 1.5 μM SYTO9, and 1×HotStarTaq-plus mastermix. The PCR primers and reaction conditions used for the HRM and sequencing are shown in Table 3.

TABLE 3

| Exon | Primer sequence (5' > 3') Upper line, forward; lower line, reverse | SEQ ID NO: | Amplification size (bp) | PCR conditions** |
|---|---|---|---|---|
| Ext | ATGGGCTGCCTCCCTCATCCT | 39 | 202 | KOD-FX |
|  | GAGAGTTACACCGAAGGGTCCATGC | 40 |  | 2 step |
| Ex3 | GCATGGACCCTTCGGTGTAACTCTC | 41 | 198 | KOD-FX |
|  | CCACTCAAACGTCCCAACCACTCTC | 42 |  | 2 step |
| Ex4 | TTGGAAGGATTCTCAACAGATG | 43 | 230 | HotStar |
|  | AGCGAGGCATGACTGTATGA | 44 |  |  |
| Ex5 & 6 | TCGTGGAAATTGAACCTTTG | 45 | 344 | HotStar |
|  | CCTAGGATGCACGCAATGTT | 46 |  |  |
| Ex7 | GCCGGGAACATGGCTTATGAGAATA | 47 | 332 | KOD-FX |
|  | GTTATGCTTCCGTTCTGGCCACAGT | 48 |  | 2 step |

TABLE 3-continued

| Exon | Primer sequence (5' > 3') Upper line, forward; lower line, reverse | SEQ ID NO: | Amplification size (bp) | PCR conditions** |
|---|---|---|---|---|
| Ex8 | CTGCACCGAATGTTAATGGA<br>GATTATGCCGCCATTCTAGG | 49<br>50 | 269 | HotStar |
| Ex9 & 10 | GGGCTGATCTGTTTGATATGC<br>CCAGAGTGGGCACCTGTGT | 51<br>52 | 343 | HotStar |
| Ex11 | CAGAAACCTCCATGCATCCT<br>CAAACAAACCCACAAACACCT | 53<br>54 | 230 | HotStar |
| Ex12 | TTGCCGATAAATAGGCCTTG<br>TTTCCTGGCTGAGAAATGCT | 55<br>56 | 201 | HotStar |
| Ex13 | TTTCCTTTCGATTTAAAGACAACTGC<br>TGGAATGTGGTTGAATACAATTGAAGA | 57<br>58 | 233 | KOD-FX 3 step |
| Ex14 | CATGTCATGAACCCTGATTGA<br>ATGAGAGACTGGCGGTGTG | 59<br>60 | 231 | HotStar |
| Ex15 | AGTCCTGGAGCAGAGGATGA<br>AAACCAAACCAAACCGACAA | 61<br>62 | 186 | HotStar |
| Ex16 | CGTAGTCAAGCCCTCTGGAA<br>TGAGATGCCAAGGCCTATTT | 63<br>64 | 197 | HotStar |
| Ex17 | TTTGGAGTTATACATCAGAGACAAAAA<br>GTGGGCGAGACACCATAAGT | 65<br>66 | 192 | Hot Star |
| Ex18 | CTCGGGTTTCTTCTTTGGAA<br>GCTCTGTGTCCCTAACAG GAG | 67<br>68 | 223 | HotStar |
| Ex19 | CTCATCAGGCCGCATACAG<br>GACCTGAGTGCAGGTGCTTT | 69<br>70 | 288 | HotStar |
| Ex20 | TCTGGACACGAACACAAAGG<br>CGGGCTTCATCTGAACATTA | 71<br>72 | 277 | HotStar |
| Ex21 | CCTGCATCTGTGGTTGTCTC<br>GGGGATGGATTTCACCTTCT | 73<br>74 | 199 | HotStar |
| Ex22 | GCTAAGAGGAATGCGGAACA<br>GGAGGCCTCAGAGTGTCTTG | 75<br>76 | 260 | HotStar |
| Ex23 | GCCAGCTGTGTGAGATGAAA<br>GTCCCCGCTCACCTAGAAAG | 77<br>78 | 270 | HotStar |
| Ex24 | TCCAGAACAATCACAACCAAAGGTGA<br>GGGTGTTTGGAGAACCTGAAGGATG | 79<br>80 | 286 | KOD-FX 2 step |
| Ex25 | GGAAGTCGAGGCGATCTTTA<br>CAAAGGAAAGCGTGGAATGT | 81<br>82 | 325 | HotStar |
| Ex26 | CCCAGACGAGCCAGTAACTC<br>TTATCCCACGCATACTGCAA | 83<br>84 | 215 | HotStar |
| Ex27 | TAGGATTGCTTGGGCTCATC<br>TTTGTGCTGAGATGCTGGAC | 85<br>86 | 235 | HotStar |
| Ex28 | TTATCCTCGTGGAGCCTGAT<br>CTCCCAAGGACAAATGCAAA | 87<br>88 | 300 | HotStar |
| Ex29 | CCATGCTAACTTGTGGTTTGG<br>CACTGTGCATCTGGGATGG | 89<br>90 | 314 | HotStar |
| Ex30 | AGTGTGTGGAGGGAGATGCT<br>GTGAGGACCCCACTCGTTTA | 91<br>92 | 279 | HotStar |
| Ex31 | TGTTTGTCCACCCTGTTTGA<br>CCAGCAGAGCTGTCTCAGGT | 93<br>94 | 291 | HotStar |
| Ex32 | CGAAATGTTACGGAGACGTG<br>TGCCACCAAGAAAGGGTAAG | 95<br>96 | 297 | HotStar |
| Ex33 | CAGGCCTTCACCTGTGTTCT<br>GTCTCTGGGGACGGAGAAG | 97<br>98 | 280 | HotStar Step down |

TABLE 3-continued

| Exon | Primer sequence (5' > 3') Upper line, forward; lower line, reverse | SEQ ID NO: | Amplification size (bp) | PCR conditions** |
|---|---|---|---|---|
| Ex34 | CAGCACGTAGGACAGCAAAA<br>GCTCACAGAACAAGGGGAGT | 99<br>100 | 321 | HotStar |
| Ex35 | ACAGCTAAGCAAACCGCCTA<br>TCTGAATTGTGGACTCCCTGT | 101<br>102 | 287 | HotStar |
| Ex36 | TCCCAGTGGAAAGTCCTGTT<br>TTGATCTGTTTGGCAAGTCG | 103<br>104 | 205 | HotStar |
| Ex37 | GAAGGAGCAGCAGTGTGGTT<br>AATGTTGACCGCCTTTGTTC | 105<br>106 | 285 | HotStar |
| Ex38 | CCAGGACCTCACCACACAG<br>ACTCTGGGTCTGGGTGACCA | 107<br>108 | 216 | HotStar |
| Ex39 | GCTGTCCCACACATGAAATAA<br>ACACCTCTGCGTGGGACTC | 109<br>110 | 314 | HotStar |
| Ex40 | GCTGCCTCTGTTTCTTTGCT<br>CTCTGGGTGGGTTCTGGTTA | 111<br>112 | 295 | HotStar |
| Ex41 | GCACCTCCCATCACTGTCTC<br>CTACATTAAGCGGGCCATTG | 113<br>114 | 316 | HotStar |
| Ex42 | AGAGACTGTCGCCTGAATGGGTGAC<br>GACGTTAGGGACACGAAAGTCTGTGG | 115<br>116 | 343 | KOD-FX<br>2 step |
| Ex43 | CTGGCCACAGTGAGAGGAG<br>GACCCATGCCAGAGAGGAT | 117<br>118 | 272 | HotStar<br>Step down |
| Ex44 | ACTCGGAGCAAGAGAGTGGA<br>GAACACAAGAGGACGCAATG | 119<br>120 | 293 | HotStar |
| Ex45 | CATTGCGTCCTCTTGTGTTC<br>AGCACTAGGACCTGGGAAGG | 121<br>122 | 248 | HotStar |
| Ex46 | GGGCTGCTCTCTCTCTCTTT<br>AACTTACCAGCCGTGGAGGGTTTG | 123<br>124 | 586 | KOD-FX<br>2 step |
| Ex47-1* | GGCCCTCCAGTAGGTGGCTAAACTC<br>GGCTGATGTAGGGCTTGATCTCGTC | 125<br>126 | 310 | KOD-FX<br>2 step |
| Ex47-2* | TCCTGTACTGCAACCCTGGTGATGT<br>CAAAGGCAGCTGTTCTTGCTGTGTC | 127<br>128 | 317 | KOD-FX<br>2 step |
| Ex48 | CAGGCTGTGATTCCTAACCCTGTCC<br>GAATAAGCACCAAAATGGCCCTTC | 129<br>130 | 341 | KOD-FX<br>Step down |

*HRM and sequencing of exon 47 were carried out for 2 separate regions.
**The number of cycles of PCR was 35, and the reaction was carried out under the following conditions:
HotStar: 94° C. for 30 seconds-55 or 57° C. (exon 38) for 30 seconds-72° C. for 60 seconds
HotStar Step down: the annealing temperature was decreased by 1° C./cycle in the first 5 cycles (58° C.→54° C.)
KOD-FX 2 step: 98° C. for 10 seconds-68° C. for 30 seconds
KOD-FX 3 step: 98° C. for 10 seconds-64° C. for 30 seconds-68° C. for 30 seconds
KOD-FX Step down: the annealing temperature was decreased by 2° C. every 5 steps (72° C.→68° C.)
Enzyme used for PCR amplification: "KOD-FX" indicates use of KOD-Fx DNA polymerase (Toyobo Co., Ltd., Osaka, Japan), and "HotStar" indicates use of HotStarTaq (Qiagen).

Samples showing aberrant melting curve patterns in the HRM analysis were sequenced. The PCR products were purified with ExoSAP-IT (GE healthcare), and cycle sequencing reaction was carried out using BigDye Terminator chemistry version 3 (Applied Biosystems). The reaction products were purified by gel filtration using Sephadex G-50 (GE healthcare) and Multiscreen-96 (Millipore), and sequences were obtained with ABI Genetic Analyzer 3100 (Applied Biosystems). The obtained sequences were subjected to analysis of the presence/absence of a mutation using SeqScape version 2.1.1 software (Applied Biosystems). The sequences of samples in which a mutation was found were subjected to sequence analysis again using the genomic DNA as a template to confirm the mutation in the genomic DNA.

As a result, two heterozygous mutations, c.3455G>A (p.G1152D) in the patient 1 and c.3110G>A (p.G1037E) in the patients 2, were identified. Both mutations were found at evolutionarily conserved Gly residues in the Gly-X-Y repeats (FIG. 1D), suggesting that the two mutations might alter the collagen IV α1α1α2 heterotrimers. These mutations were absent in 200 Japanese normal controls, and evaluation using web-based prediction tools strongly suggested that these substitutions are pathogenic (Table 4).

TABLE 4

| Patient | Mutation | SIFT | PolyPhen | PolyPhen-2 | Mutation taster | Align GVGD |
|---|---|---|---|---|---|---|
| 1 | c.3455G > A p.G1152D | 0.00 | probably damaging 2.142 | probably damaging 1.00 | Disease causing | C65 |
| 2 | c.3110G > A p.G1037E | 0.00 | probably damaging 2.367 | probably damaging 1.00 | Disease causing | C65 |

The following tools were used for the prediction.
(1) SIFT (http://sift.jcvi.org/)
Scores less than 0.05 indicate substitutions are considered to be intolerant (a protein functional change is affected).
(2) PolyPhen (http://genetics.bwh.harvard.edu/pph/)
Scores more than 2.0 are considered to be pathogenic.
(3) PolyPhen-2 (http://genetics.bwh.harvard.edu/pph2/)
The score ranges from 0.000 (most probably benign) to 0.999 (most probably damaging).
(4) Mutation Taster (http://neurocore.charite.de/Mutation-Taster/index.html)
(5) Align GVGD (http://agvgd.iarc.fr/agvgd_input.php)
From Class C0 (less likely) to Class C65 (most likely).

The c.3455G>A mutation of the patient 1 was also found in the patient's mother and maternal grandfather, both of whom are asymptomatic, and in his maternal uncle who showed congenital left hemiplegia (FIGS. 1A and B). Therefore, the c.3455G>A mutation can be considered to be a dominant pathogenic mutation with incomplete penetrance. The c.3110G>A mutation in the patient 2 was not found in his parents, indicating that this mutation occurred de novo (FIG. 1C).

The invention claimed is:

1. A method for diagnosing a risk of porencephaly and/or cerebral hemorrhage and treating porencephaly and/or cerebral hemorrhage, said method comprising:
   (a) obtaining a sample from a in utero human fetus;
   (b) detecting at least one mutation present in at least one allele of a COL4A2 gene in the sample;
   (c) diagnosing the human fetus as having a high risk of porencephaly and/or cerebral hemorrhage after detecting the presence of at least one mutation in at least one allele of the COL4A2 gene; and
   (d) administering cesarean section to the woman carrying the in utero human fetus diagnosed with a high risk of porencephaly and/or cerebral hemorrhage,
   wherein said at least one mutation comprises at least one selected from the group consisting of (1) and (2) below:
   (1) mutation of G at position 3455 of the COL4A2 gene coding region (position 301 of SEQ ID NO:31) to A; and
   (2) mutation of G at position 3110 of the COL4A2 gene coding region (position 385 of SEQ ID NO:28) to A.

2. The method according to claim 1, wherein the detecting step is in a genomic sequence using a genomic DNA sample.

3. The method according to claim 1, wherein DNA in said sample is amplified prior to said detecting.

4. The method according to claim 3, wherein said DNA is amplified by PCR.

5. The method according to claim 3, wherein said DNA is amplified by PCR using at least one primer pair selected from the group consisting of primer pair SEQ ID NO: 99 and SEQ ID NO: 100 and primer pair SEQ ID NO: 107 and SEQ ID NO: 108.

6. A method for diagnosing a risk of porencephaly and/or cerebral hemorrhage, said method comprising:
   (a) obtaining a sample separated from a subject;
   (b) amplifying DNA using primer pairs;
   (c) detecting the amplified sample of at least one mutation present in at least one allele of a COL4A2 gene in the sample; and
   (d) diagnosing the subject as having a high risk of porencephaly and/or cerebral hemorrhage after detecting the presence of at least one mutation in at least one allele of the COL4A2 gene is detected,
   wherein said at least one mutation comprises at least one selected from the group consisting of (1) and (2) below:
   (1) mutation of G at position 3455 of the COL4A2 gene coding region (position 301 of SEQ ID NO:31) to A; and
   (2) mutation of G at position 3110 of the COL4A2 gene coding region (position 385 of SEQ ID NO:28) to A,
   wherein said primer pair is at least one selected from the group consisting of primer pair SEQ ID NO: 99 and SEQ ID NO: 100 and primer pair SEQ ID NO: 107 and SEQ ID NO: 108.

7. The method according to claim 6, wherein said detecting is by high-resolution melting curve (HRM) analysis or direct sequencing.

8. The method according to claim 6, wherein said subject is a postnatal human or human fetus.

9. The method according to claim 6, wherein the diagnosing the risk of porencephaly and/or cerebral hemorrhage occurs during the fetal period to perinatal period in a human fetus.

10. The method according to claim 6, wherein the detecting step is in a genomic sequence using a genomic DNA sample.

11. The method according to claim 6, wherein said DNA is amplified by PCR.

12. A method for detecting at least one mutation in at least one allele of a COL4A2 gene in a human subject, comprising:
   (a) obtaining a sample separated from the subject; and
   (b) detecting at least one mutation present in at least one allele of a COL4A2 gene in the sample by high-resolution melting curve (HRM) analysis or direct sequencing, wherein said at least one mutation comprises at least one selected from the group consisting of (1) and (2) below:
   (1) mutation of G at position 3455 of the COL4A2 gene coding region (position 301 of SEQ ID NO:31) to A; and
   (2) mutation of G at position 3110 of the COL4A2 gene coding region (position 385 of SEQ ID NO:28) to A.

* * * * *